US010424407B2

(12) United States Patent
Hyde et al.

(10) Patent No.: US 10,424,407 B2
(45) Date of Patent: *Sep. 24, 2019

(54) SYSTEMS AND METHODS FOR INDIVIDUAL IDENTIFICATION AND AUTHORIZATION UTILIZING CONFORMABLE ELECTRONICS

(71) Applicant: ELWHA LLC, Bellevue, WA (US)

(72) Inventors: Roderick A. Hyde, Redmond, WA (US); Jordin T. Kare, San Jose, CA (US); Gary L. McKnight, Bothell, WA (US); Robert C. Petroski, Issaquah, WA (US); Elizabeth A. Sweeney, Seattle, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/029,056

(22) Filed: Jul. 6, 2018

(65) Prior Publication Data

US 2019/0006031 A1 Jan. 3, 2019

Related U.S. Application Data

(63) Continuation-in-part of application No. 15/416,504, filed on Jan. 26, 2017, now Pat. No. 10,037,641,
(Continued)

(51) Int. Cl.
*G06F 19/00* (2018.01)
*G16H 10/65* (2018.01)
(Continued)

(52) U.S. Cl.
CPC ............. *G16H 10/65* (2018.01); *G06F 21/32* (2013.01); *G07C 9/00563* (2013.01);
(Continued)

(58) Field of Classification Search
CPC ............ G07C 9/00158; G07C 9/00134; G07C 9/00071; G07C 9/00563;
(Continued)

(56) References Cited

U.S. PATENT DOCUMENTS 4,783,823 A 11/1988 Tasaki
6,317,834 B1 11/2001 Gennaro
(Continued)

FOREIGN PATENT DOCUMENTS

JP 2006346221 A 12/2006
WO 2015167926 A1 11/2015

OTHER PUBLICATIONS http://alicebonasio.com/virtual-reality/training-the-next-generation-of-su-rgeons-with-augmented-reality/, Jul. 2016.
(Continued)

*Primary Examiner* — Dionne Pendleton
(74) *Attorney, Agent, or Firm* — Daniel J. Honz; Advent, LLP

(57) ABSTRACT

An identification device includes, but is not limited to, a deformable substrate configured to conform to a skin surface of a body portion of a healthcare provider; a sensor assembly coupled to the deformable substrate, the sensor assembly including one or more identity sensors configured to generate one or more identity sense signals associated with at least one physical characteristic of an individual subject other than the healthcare provider; circuitry configured to compare the one or more identity sense signals generated by the sensor assembly to reference data indicative of one or more physical characteristics associated with an identity; and a reporter configured to generate one or more communication signals associated with a comparison of the one or more identity sense signals generated by the sensor assembly to
(Continued)

reference data indicative of one or more physical characteristics associated with an identity of at least one individual.

20 Claims, 34 Drawing Sheets

Related U.S. Application Data which is a continuation-in-part of application No. 15/232,884, filed on Aug. 10, 2016, now Pat. No. 10,013,832, and a continuation-in-part of application No. 15/232,894, filed on Aug. 10, 2016, now Pat. No. 9,779,352, and a continuation-in-part of application No. 15/232,888, filed on Aug. 10, 2016, now Pat. No. 10,032,109.

(51) Int. Cl.
| | |
|---|---|
| *G16H 40/67* | (2018.01) |
| *G16H 40/20* | (2018.01) |
| *G16H 80/00* | (2018.01) |
| *G16H 10/60* | (2018.01) |
| *G07C 9/00* | (2006.01) |
| *G06F 21/32* | (2013.01) |

(52) U.S. Cl.
CPC ............. *G16H 10/60* (2018.01); *G16H 40/20* (2018.01); *G16H 40/67* (2018.01); *G16H 80/00* (2018.01)

(58) Field of Classification Search
CPC ...... G07C 2009/00095; G07C 9/00087; A61B 2562/0214; A61B 2562/164; A61B 5/0059; A61B 5/053; A61B 5/1171; A61B 5/6825; A61B 5/6833; A61B 5/7246; A61B 5/742; G06F 21/32; G16H 10/60
See application file for complete search history.

(56) References Cited

U.S. PATENT DOCUMENTS

| | | | |
|---|---|---|---|
| 8,010,798 B1* | 8/2011 | Lemke | G06F 21/32 340/5.53 |
| 10,037,641 B2* | 7/2018 | Hyde | G07C 9/00563 |
| 2004/0236701 A1 | 11/2004 | Beenau | |
| 2006/0000902 A1 | 1/2006 | Strawn | |
| 2010/0130875 A1 | 5/2010 | Banet | |
| 2010/0134609 A1* | 6/2010 | Johnson | G06F 19/3418 348/77 |
| 2011/0213625 A1* | 9/2011 | Joao | G06F 19/328 705/3 |
| 2011/0254682 A1 | 10/2011 | Sigrist Christensen | |
| 2012/0165759 A1 | 6/2012 | Rogers | |
| 2012/0320581 A1 | 12/2012 | Rogers | |
| 2013/0041235 A1 | 2/2013 | Rogers | |
| 2013/0294617 A1 | 11/2013 | Alberth, Jr. | |
| 2013/0297301 A1 | 11/2013 | Alberth, Jr. | |
| 2014/0081665 A1 | 3/2014 | Holmes | |
| 2014/0245786 A1 | 9/2014 | Proud | |
| 2015/0210042 A1 | 7/2015 | Tapio | |
| 2015/0292856 A1 | 10/2015 | Ganton | |
| 2015/0363563 A1 | 12/2015 | Hallwachs | |
| 2016/0051156 A1 | 2/2016 | Kim | |
| 2016/0136356 A1* | 5/2016 | Ribble | G06F 19/3418 604/111 |
| 2016/0189528 A1 | 6/2016 | Lee | |
| 2016/0247161 A1 | 8/2016 | Wang | |
| 2017/0014049 A1 | 1/2017 | Dumanyan | |
| 2017/0021172 A1 | 1/2017 | Perez | |
| 2017/0032168 A1 | 2/2017 | Kim | |
| 2017/0036066 A1 | 2/2017 | Chahine | |
| 2017/0039358 A1 | 2/2017 | Yuen | |
| 2017/0100035 A1 | 4/2017 | Heikenfeld | |
| 2017/0102334 A1 | 4/2017 | Zaretski | |
| 2017/0112434 A1 | 4/2017 | Lane | |
| 2017/0112453 A1* | 4/2017 | Quinn | A61B 5/0002 |
| 2017/0164876 A1 | 6/2017 | Hyde | |
| 2017/0169185 A1 | 6/2017 | Weng | |
| 2017/0273560 A1 | 9/2017 | Ballam | |
| 2017/0293749 A1 | 10/2017 | Baek | |
| 2017/0364732 A1 | 12/2017 | Komogortsev | |
| 2019/0104919 A1* | 4/2019 | Shelton, IV | A61B 1/00006 |

OTHER PUBLICATIONS http://medcitynews.com/2014//06/virtual-reality-surgical-device-inspired-fl-ight-simulator-gets-fda-clearance/ , Jun. 2014.
PCT International Search Report; International App. No. PCT/US2017/046106; dated Nov. 17, 2017; pp. 1-4.
PCT International Search Report; International App. No. PCT/US2017/046114; dated Nov. 22, 2017; pp. 1-6.
Ultraflexible organic photonic skin, Yokota et al., Sci. Adv. (2016); 2 : e1501856.
https://www.patentlyapple.com/patently-apple/2014/01/motorola-skin-tattoo-patent-contains-bizanre-big-broter-twist.html (2014).
https://www.technologyreview.com/s/602000/how-to-operate-your-smart-watch-with-the-same-hand-that-wears-it/?utm.sub. --campaign= newsletters&utm.sub --source=newsletter-weekly-mobile&utm.sub —medium=email&utm.sub — content=20160801&goal=0.sub. --997ed6f472-a395fccd6e-153689181&mc_cid=a395Fccd6e&mc_eid=33ecfcf2ad (2016).
Recent advances in gecko adhesion and friction mechanisms and development of gecko-inspired dry adhesive surfaces, Zhou et al., Friction 1(2): 114-129 (2013).
Magnetically Actuated Patterns for Bioinspired Reversible Adhesion (Dry and Wet), Drotlef et al., Adv. Mater. (2013).
Reverse Adhesion of a Gecko-Inspired Synthetic Adhesive Switched by an Ion-Exchange Polymer-Metal Composite Actuator, Guo et al., ACS Appl. Mater. Interfaces, 7, 5480-5487 (2015).
Switching adhesion and friction by light using photosensitive guest-host interactions, Blass et al., Chem. Commun., 51, 1830 (2015).
Miniaturized Flexible Electronic Systems with Wireless Power and Near-Field Communication Capabilities, Kim et al., Adv. Fund. Mater. 25, 4761-4767 (2015).
Epidermal Differential Impedance Sensor for Conformal Skin Hydration Monitoring, Huang et al., Biointerphases 7:52 (2012).
Epidermal Electronics, Kim et al., Science 333, 838 (2011).
http://www.mhealthtalk.com/smart-skin/ (2011).
Multifunctional Epidermal Electronics Printed Directly Onto the Skin, Yeo et al., Adv. Mater. (2013).
http://www.mc10inc.com/our-story/#content-17 (Accessed Nov. 16, 2016).
https://www.technologyreview.com/s/428944/making-stretchable-electronics/ (2012).
Breaking free, WTIN (publisher), Future Materials (2012).
http://forwardthinking.pcmag.com/show-reports/312046-d11-is-phone-authentication-possible-by-taking-a-pill-motorola-says-yes (2013).

\* cited by examiner

1600

1602 GENERATE ONE OR MORE IDENTITY SENSE SIGNALS CORRESPONDING TO AN INDIVIDUAL SUBJECT VIA AN IDENTIFICATION DEVICE HAVING A DEFORMABLE SUBSTRATE AND AT LEAST ONE SENSOR COUPLED TO THE DEFORMABLE SUBSTRATE

1604 COMPARE THE ONE OR MORE IDENTITY SENSE SIGNALS TO REFERENCE DATA INDICATIVE OF ONE OR MORE PHYSICAL CHARACTERISTICS ASSOCIATED WITH AN IDENTITY OF AT LEAST ONE INDIVIDUAL

1606 REPORT ONE OR MORE COMMUNICATION SIGNALS RELATED TO THE IDENTITY SENSE SIGNALS OR THE COMPARISON TO REFERENCE DATA

1702 GENERATE ONE OR MORE IDENTITY SENSE SIGNALS CORRESPONDING TO AN INDIVIDUAL SUBJECT VIA AN IDENTIFICATION DEVICE HAVING A DEFORMABLE SUBSTRATE AND AT LEAST ONE SENSOR COUPLED TO THE DEFORMABLE SUBSTRATE

1704 COMPARE THE ONE OR MORE IDENTITY SENSE SIGNALS TO REFERENCE DATA INDICATIVE OF ONE OR MORE PHYSICAL CHARACTERISTICS ASSOCIATED WITH AN IDENTITY OF AT LEAST ONE INDIVIDUAL

1706 COMPARE THE ONE OR MORE IDENTITY SENSE SIGNALS OR A DETERMINED IDENTITY WITH ONE OR MORE AUTHORIZATION PARAMETERS

1708 REPORT TO AN ASSOCIATED EXTERNAL DEVICE ONE OR MORE COMMUNICATION SIGNALS RELATED TO THE COMPARISON WITH AUTHORIZATION PARAMETERS

1802 GENERATE ONE OR MORE IDENTITY SENSE SIGNALS CORRESPONDING TO AN INDIVIDUAL SUBJECT VIA AN IDENTIFICATION DEVICE HAVING A DEFORMABLE SUBSTRATE AND AT LEAST ONE IDENTITY SENSOR COUPLED TO THE DEFORMABLE SUBSTRATE

1804 COMPARE THE ONE OR MORE IDENTITY SENSE SIGNALS TO REFERENCE DATA INDICATIVE OF ONE OR MORE PHYSICAL CHARACTERISTICS ASSOCIATED WITH AN IDENTITY OF AT LEAST ONE INDIVIDUAL

1806 TRANSITION AN ADHESIVE FROM AN ADHESIVE STATE TO A NON-ADHESIVE STATE UPON DETERMINATION THAT THE IDENTITY SENSE SIGNALS DO NOT PROVIDE A THRESHOLD CORRESPONDENCE TO THE PHYSICAL CHARACTERISTICS

1902 GENERATE ONE OR MORE IDENTITY SENSE SIGNALS CORRESPONDING TO AN INDIVIDUAL SUBJECT VIA AN IDENTIFICATION DEVICE HAVING A DEFORMABLE SUBSTRATE AND AT LEAST ONE IDENTITY SENSOR COUPLED TO THE DEFORMABLE SUBSTRATE

1904 COMPARE THE ONE OR MORE IDENTITY SENSE SIGNALS TO REFERENCE DATA INDICATIVE OF ONE OR MORE PHYSICAL CHARACTERISTICS ASSOCIATED WITH AN IDENTITY OF AT LEAST ONE INDIVIDUAL

1906 TRANSITION AN ADHESIVE FROM A NON-ADHESIVE STATE TO AN ADHESIVE STATE UPON DETERMINATION THAT THE IDENTITY SENSE SIGNALS PROVIDE A THRESHOLD CORRESPONDENCE TO THE PHYSICAL CHARACTERISTICS

FIG. 19

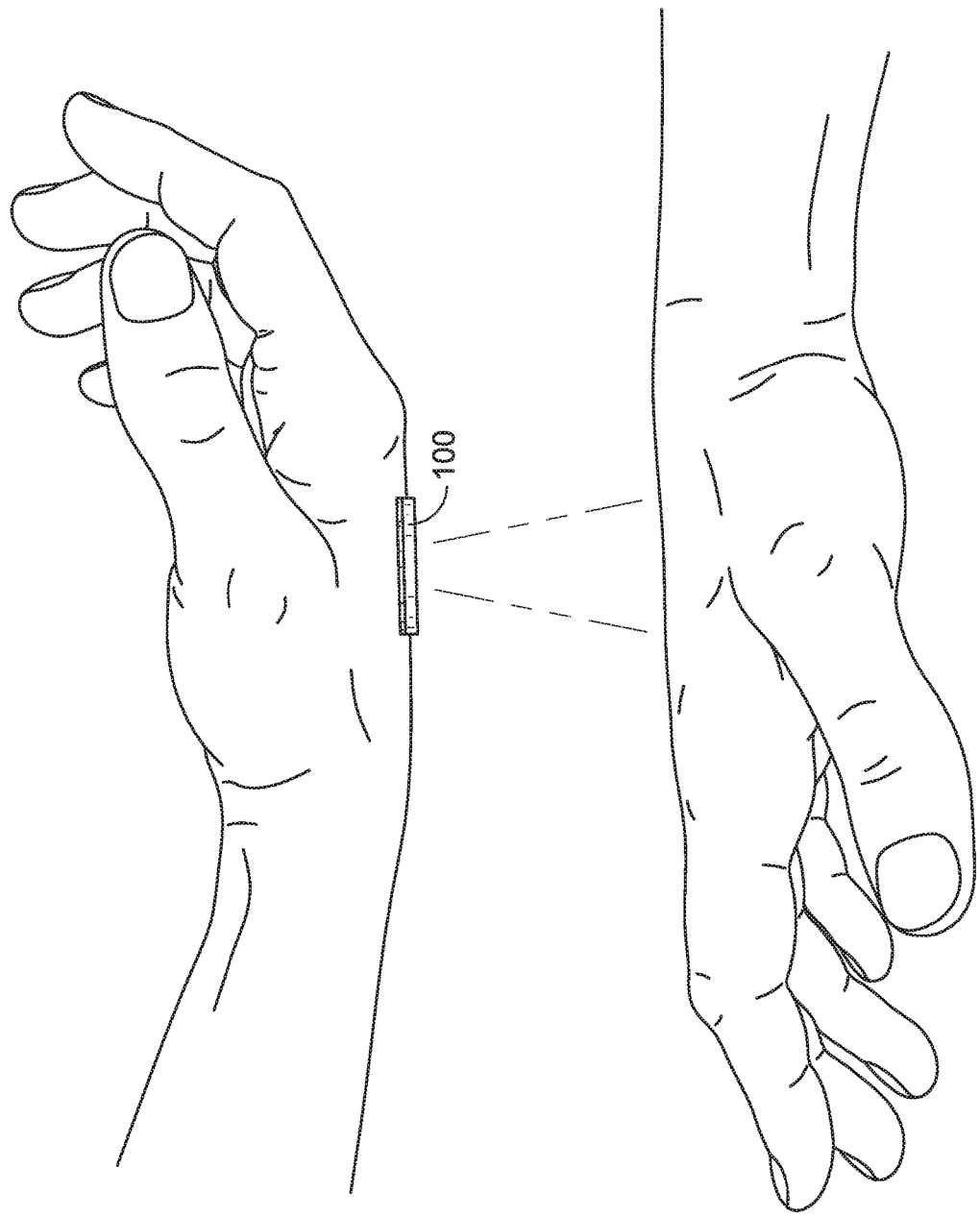

2300 EXTERNAL DEVICE

2400 MEDICAL DEVICE

2402 SURGICAL DEVICE

2404 IMAGING DEVICE

2406 THERAPEUTIC DEVICE

2408 DRUG DELIVERY TOOL

2410 ASSISTIVE DEVICE

2412 REHABILITATIVE DEVICE

2414 VENDING MACHINE

2416 DISPLAY DEVICE

2418 LIQUID CRYSTAL DISPLAY

2420 LIGHT-EMITTING DIODE DISPLAY

2422 ORGANIC LIGHT-EMITTING DIODE DISPLAY

2424 TOUCHSCREEN ASSEMBLY

2426 PROJECTION-BASED DISPLAY

2428 INTERACTIVE DRAPE

3402 GENERATE ONE OR MORE IDENTITY SENSE SIGNALS CORRESPONDING TO AN INDIVIDUAL SUBJECT VIA AN IDENTIFICATION DEVICE CONFORMING TO A SKIN SURFACE OF A BODY PORTION OF A HEALTHCARE PROVIDER, THE IDENTIFICATION DEVICE HAVING A DEFORMABLE SUBSTRATE AND ONE OR MORE IDENTITY SENSORS COUPLED TO THE DEFORMABLE SUBSTRATE

3404 COMPARE THE ONE OR MORE IDENTITY SENSE SIGNALS TO REFERENCE DATA INDICATIVE OF ONE OR MORE PHYSICAL CHARACTERISTICS ASSOCIATED WITH AN IDENTITY OF AT LEAST ONE INDIVIDUAL

3406 REPORT ONE OR MORE COMMUNICATION SIGNALS ASSOCIATED WITH THE IDENTITY SENSE SIGNALS OR THE COMPARISON TO REFERENCE DATA

3408 AUTHORIZE THE HEALTHCARE PROVIDER TO PERFORM A HEALTH SERVICE ACTION WITH RESPECT TO THE INDIVIDUAL SUBJECT

3502 GENERATE ONE OR MORE IDENTITY SENSE SIGNALS CORRESPONDING TO AN INDIVIDUAL SUBJECT VIA AN IDENTIFICATION DEVICE CONFORMING TO A SKIN SURFACE OF A BODY PORTION OF THE INDIVIDUAL SUBJECT, THE IDENTIFICATION DEVICE HAVING A DEFORMABLE SUBSTRATE AND ONE OR MORE IDENTITY SENSORS COUPLED TO THE DEFORMABLE SUBSTRATE

3504 COMPARE THE ONE OR MORE IDENTITY SENSE SIGNALS TO REFERENCE DATA INDICATIVE OF ONE OR MORE PHYSICAL CHARACTERISTICS ASSOCIATED WITH AN IDENTITY OF AT LEAST ONE INDIVIDUAL

3506 COMPARE THE ONE OR MORE IDENTITY SENSE SIGNALS OR THE IDENTITY OF THE AT LEAST ONE INDIVIDUAL WITH ONE OR MORE AUTHORIZATION PARAMETERS INCLUDING AT LEAST ONE SCHEDULED PARAMETER

3508 REPORT ONE OR MORE COMMUNICATION SIGNALS ASSOCIATED WITH THE COMPARISON OF THE ONE OR MORE IDENTITY SENSE SIGNALS OR THE IDENTITY OF THE AT LEAST ONE INDIVIDUAL WITH THE ONE OR MORE AUTHORIZATION PARAMETERS

FIG. 35

SYSTEMS AND METHODS FOR INDIVIDUAL IDENTIFICATION AND AUTHORIZATION UTILIZING CONFORMABLE ELECTRONICS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

The present application constitutes a continuation-in-part of U.S. patent application Ser. No. 15/232,884, entitled SYSTEMS AND METHODS FOR INDIVIDUAL IDENTIFICATION AND AUTHORIZATION UTILIZING CONFORMABLE ELECTRONICS, naming RODERICK A. HYDE, JORDIN T. KARE, GARY L. MCKNIGHT, ROBERT C. PETROSKI, and ELIZABETH A. SWEENEY as inventors, filed 10 Aug. 2016, which is currently co-pending or is an application of which a currently co-pending application is entitled to the benefit of the filing date.

The present application constitutes a continuation-in-part of U.S. patent application Ser. No. 15/232,888, entitled SYSTEMS AND METHODS FOR INDIVIDUAL IDENTIFICATION AND AUTHORIZATION UTILIZING CONFORMABLE ELECTRONICS, naming RODERICK A. HYDE, JORDIN T. KARE, GARY L. MCKNIGHT, ROBERT C. PETROSKI, and ELIZABETH A. SWEENEY as inventors, filed 10 Aug. 2016, which is currently co-pending or is an application of which a currently co-pending application is entitled to the benefit of the filing date.

The present application constitutes a continuation-in-part of U.S. patent application Ser. No. 15/232,894, entitled SYSTEMS AND METHODS FOR INDIVIDUAL IDENTIFICATION AND AUTHORIZATION UTILIZING CONFORMABLE ELECTRONICS, naming RODERICK A. HYDE, JORDIN T. KARE, GARY L. MCKNIGHT, ROBERT C. PETROSKI, and ELIZABETH A. SWEENEY as inventors, filed 10 Aug. 2016, which is currently co-pending or is an application of which a currently co-pending application is entitled to the benefit of the filing date.

The present application constitutes a continuation-in-part of U.S. patent application Ser. No. 15/416,504, entitled SYSTEMS AND METHODS FOR INDIVIDUAL IDENTIFICATION AND AUTHORIZATION UTILIZING CONFORMABLE ELECTRONICS, naming RODERICK A. HYDE, JORDIN T. KARE, GARY L. MCKNIGHT, ROBERT C. PETROSKI, AND ELIZABETH A. SWEENEY as inventors, filed 26 Jan. 2017, which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, an identification device includes, but is not limited to, a deformable substrate configured to conform to a skin surface of a body portion of a healthcare provider; a sensor assembly coupled to the deformable substrate, the sensor assembly including one or more identity sensors configured to generate one or more identity sense signals associated with at least one physical characteristic of an individual subject other than the healthcare provider; circuitry operably coupled to the sensor assembly and configured to receive the one or more identity sense signals associated with the at least one physical characteristic of the individual subject, the circuitry including an identity comparison module configured to compare the one or more identity sense signals generated by the sensor assembly to reference data indicative of one or more physical characteristics associated with an identity of at least one individual to determine whether the one or more identity sense signals correspond to the identity of the at least one individual; and a reporter operably coupled to the circuitry and configured to generate one or more communication signals responsive to instruction by the circuitry prior to or in conjunction with authorization of the healthcare provider to perform a health service action with respect to the individual subject, the one or more communication signals associated with a comparison of the one or more identity sense signals generated by the sensor assembly to reference data indicative of one or more physical characteristics associated with an identity of at least one individual.

In an aspect, a method includes, but is not limited to, generating one or more identity sense signals corresponding to an individual subject via an identification device having a deformable substrate configured to conform to a skin surface of a body portion of a healthcare provider and having one or more identity sensors coupled to the deformable substrate, the one or more identity sense signals associated with at least one physical characteristic of the individual subject; comparing via circuitry the one or more identity sense signals to reference data indicative of one or more physical characteristics associated with an identity of at least one individual to determine whether the one or more identity sense signals correspond to the identity of the at least one individual; and prior to or in conjunction with authorization of the healthcare provider to perform a health service action with respect to the individual subject, reporting to an external device one or more communication signals associated with a comparison of the one or more identity sense signals to reference data indicative of one or more physical characteristics associated with an identity of at least one individual.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 16 is a flowchart of a method of identifying an individual using conformable electronics positioned on the individual.

FIG. 17 is a flowchart of a method of identifying and authorizing an individual using conformable electronics positioned on the individual.

FIG. 18 is a flowchart of a method of adjusting an adhesive state of an adhesive responsive to identification of an individual using conformable electronics.

FIG. 19 is a flowchart of a method of adjusting an adhesive state of an adhesive responsive to identification of an individual using conformable electronics.

FIG. 22B is a schematic of an embodiment of a healthcare provider identification device such as shown in FIG. 20.

FIG. 24 is a schematic of an embodiment of an external device such as shown in FIG. 23.

FIG. 34 is a flowchart of a method of identifying an individual subject using conformable electronics positioned on a healthcare provider.

FIG. 35 is a flowchart of a method of identifying an individual subject using conformable electronics positioned on the individual subject and comparing identity sense signals or an identity of the individual subject with one or more authorization parameters including at least one scheduled parameter.

DETAILED DESCRIPTION

Figure 1:
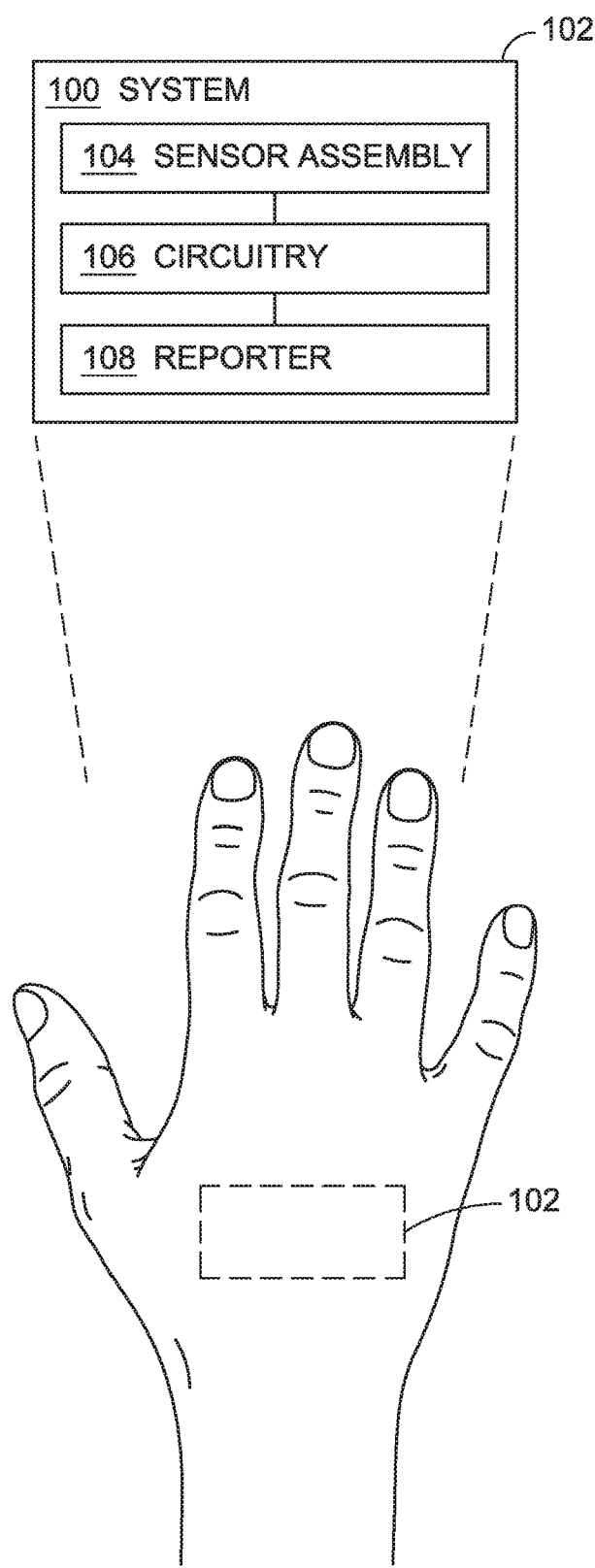
FIG. 1 is a schematic of a system for identification of an individual using conformable electronics.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Systems, devices, and methods are described for identification and authorization of individuals using conformable electronics for aspects of the identification and authorization processes. Such systems can be applied to, maintained against, or otherwise be in contact with, a skin surface of a body portion of an individual to evaluate one or more physical characteristics of the individual, including but not limited to, skin topography features (e.g., pattern of skin surface, follicle pattern, pore pattern, pigmentation, etc.), vascular properties or layouts, electric current pattern (e.g., photovoltaic current pattern), or skin resistivity measurement. The physical characteristics can be compared against reference data that include physical characteristics of known identities to determine whether the measured physical characteristics correspond to the reference physical characteristics, whereby the particular identity can be determined or inferred. In an embodiment, the identification can disable or enable operation or functionality of one or more components of the system. For example, where an individual does not match an identity that corresponds to any reference identity, is identified but is not in a state suitable for operation of a device (e.g., intoxicated, stressed, etc.), or is identified but not authorized to use a particular device or system, the system can disable a power connection to one or more components of the system, thereby preventing their use. Where an individual is identified, the system can enable a power connection to one or more components of the system (e.g., sensors, reporters, etc.), thereby enabling or activating their use. In an embodiment, the identification can lead to subsequent authorization, such as authorization reported to or processed by an external device. Such authorization can permit operation of the external device or associated device or system by the identified and authorized individual, or can permit an external device or associated device or system to be aware of the identity of a particular user.

In an embodiment, the systems described herein can be configured to adhere to a skin surface of a body portion of the individual, which can facilitate ease of use and avoid unintentional misplacement of the identification and/or authorization system. In an embodiment, such systems can be configured to disable the functionality of one or more components when removed from the skin surface, or otherwise become difficult to remove intact, such as to avoid transfer of the system to another user. In an embodiment, the systems described herein can be removable and reusable.

In an embodiment, the systems described herein can sense a combination of skin properties to confirm that the host body portion is associated with an individual that is present and in good health, which can avoid security issues associated with identification and/or authorization systems that utilize biometric or other identification/authorization protocols that can be circumvented by removal of a body portion or embedded tag used for identification/authorization.

In an embodiment, the systems described herein employ one or more identity sensors configured to monitor or sense at least one physical characteristic of the individual. The identity sensor can include, but is not limited to, an optical sensor, an electromagnetic sensor, an impedance sensor, a capacitive sensor, an electrophysiological sensor, a plethysmographic sensor, a resistive sensor, a biosensor, or a chemical sensor. The identity sensors are coupled to circuitry configured to compare the output of the identity sensors to reference data to determine whether the output of the identity sensors corresponds to an identity of a known individual. The systems can also include one or more of physiological sensors, proximity sensors, contact sensors, pressure sensors, or temperature sensors to facilitate operation of the system, to provide contextual data in combination with the output from the identity sensors, to toggle activation/deactivation of one or more components of the system, or the like.

In an embodiment, the systems described herein employ a reporter configured to generate one or more communication signals responsive to instruction by the circuitry. For example, the reporter can convey information via the one or more communication signals directed to the output of the sensors, a comparison of the output of the sensors with reference data (e.g., reference identity data or reference physical characteristics), identity information of the individual on which the system is positioned, authorization information (e.g., whether or not an identified individual is authorized, such as authorized to operate a particular device, machine, electronic device, etc.), or the like.

In an embodiment, shown in FIG. 1, a system (or device) 100 is configured to evaluate one or more physical characteristics of an individual on which the system 100 is positioned to facilitate identification of the individual. The system 100 includes a deformable substrate 102, a sensor assembly 104, circuitry 106, and a reporter 108. The deformable substrate 102 is configured to conform to a contour of a body portion of an individual subject (e.g., the curvature of a limb). For example, the deformable substrate 102 can comprise a deformable (e.g., conformable, flexible, stretchable, etc.) material configured to interface with, and conform to, the body portion. The body portion is shown in FIG. 1 as a hand, however the system 100 can be positioned on the skin surface of any body portion, including but not limited to, an arm, an elbow, a wrist, a hand, a finger, a leg, a knee, an ankle, a foot, a toe, a facial region, a neck region, a torso region, or the like. The pliable nature of the deformable substrate 102 (e.g., flexibility and stretchability) facilitates interaction/interfacing with the body portion, which includes a generally low-modulus and deformable natural skin surface. In an embodiment, the deformable substrate 102 can include one or more of a stretchable/flexible fabric, paper, or polymer (e.g., a natural or synthetic elastomeric polymer, polyimide, polyvinyl, an organic polymer such as PDMS, xylylene, parylene, an inorganic polymer, a biopolymer, a composite material, or any combination thereof), a film (e.g., a hydrocolloid film), a membrane (e.g., a nanomembrane, such as a silicon nanomembrane), a gas-permeable elastomeric sheet, or other deformable (e.g., stretchable, flexible, pliable) material. The deformable substrate 102 can be positioned in proximity with the skin surface according to various mechanisms including, but not limited to, affixed to the skin via an adhesive material, held in place by an external pressure, such as pressure provided by a material wrapped around or about a body portion (e.g., a fabric, a garment, a glove, a bandage, etc.), affixed in a textile, fabric, garment, accessory (e.g., a glove, a sock, a finger cot, etc.), or so forth.

In embodiments, the system 100 includes at least one flexible or stretchable electronic component. For example, at least one of the sensor assembly 104 (e.g., identity sensors as described herein), the circuitry 106, or the reporter 108 can include or be formed of flexible or stretchable electronics coupled to the deformable substrate 102. For example, interconnects (not illustrated) between these components or within the circuitry can include or be formed of flexible or stretchable electronics (e.g., serpentine conducting tracings allowing for stretchable interconnects) and coupled to the deformable substrate 102. For example, a power source (e.g., power supply 600 described herein), can include or be formed of flexible or stretchable electronics and be coupled to the deformable substrate 102. In embodiments, the at least one flexible or stretchable electronic component includes at least one of a wavy, bent, mesh (e.g., open mesh), buckled, or serpentine geometry. In embodiments, the at least one flexible or stretchable electronic component includes at least one nanowire, at least one nanoribbon, or at least one nanomembrane. For example, the system 100 can include one or more multifunctional electronic units comprising a stretchable/flexible system including a sensor assembly (e.g., sensor assembly 104), reporter (e.g., reporter 108), and power source (e.g., power supply 600) in communication via associated circuitry (e.g., circuitry 106), including interconnects, residing in or on a deformable substrate (e.g., deformable substrate 102).

In embodiments, the system 100 can include at least one ultrathin electronic component. For example, an ultrathin (e.g., less than 20 micrometers) electronic component can include a thinned wafer (e.g., thinned silicon wafer bonded to a polymer substrate), an ultrathin chip, or the like. For example, ultrathin circuitry can include conductive layers formed on a deformable substrate (e.g., deformable substrate 102) such as parylene by evaporation deposition with UV lithography and etching. For example, at least one of the sensory assembly 104, the circuitry 106, or the reporter 108 can include ultrathin electronics.

In embodiments, the system 100 can include at least one electrically conductive thread, yarn, or textile. For example, the sensory assembly 104, the circuitry 106, or the reporter 108 can include at least one electrically conductive thread or yarn. Electrically conductive threads, yarns, or textiles can be configured to provide sufficient current to induce at least one of a wired or wireless coupling, e.g., between electronic components. For example, electronically conductive threads, yarns, or textiles may form circuitry 106 configured to function in communication between one or more sensor assemblies 106, one or more reporters 108, or other circuitry 106. For example, electronically conductive threads, yarns, or textiles may form at least a portion of circuitry 106 configured to function in communication between a plurality of multifunctional electronic units each comprising one or more sensor assemblies 106, one or more reporters 108, and circuitry 106. Electrically conductive fibers, threads, and yarns can include a metallic material, semi-metallic material, semi-insulative material, semi-conductive material (e.g., silicon and a gallium arsenide), or transparent conductive material (e.g., an indium-tin-oxide (ITO) material). Electrical threads or yarns can be embedded in textiles using weaving, knitting or embroidery, for example, or can be attached using nonwoven production techniques such as adhesion. For example, electrically conductive yarns having curved configuration can be attached to an elastic textile (e.g., by sewing or by adhesion) and can form all or part of a sensor assembly 104 that measures one or more physical characteristics of an individual, e.g., as the curved configuration is altered, such as due to particular skin topography or the like.

The sensor assembly 104 is coupled to the deformable substrate 102 and is positioned to generate one or more sense signals associated with a physical characteristic of the individual subject on whom the system 100 is positioned.

Figure 2:
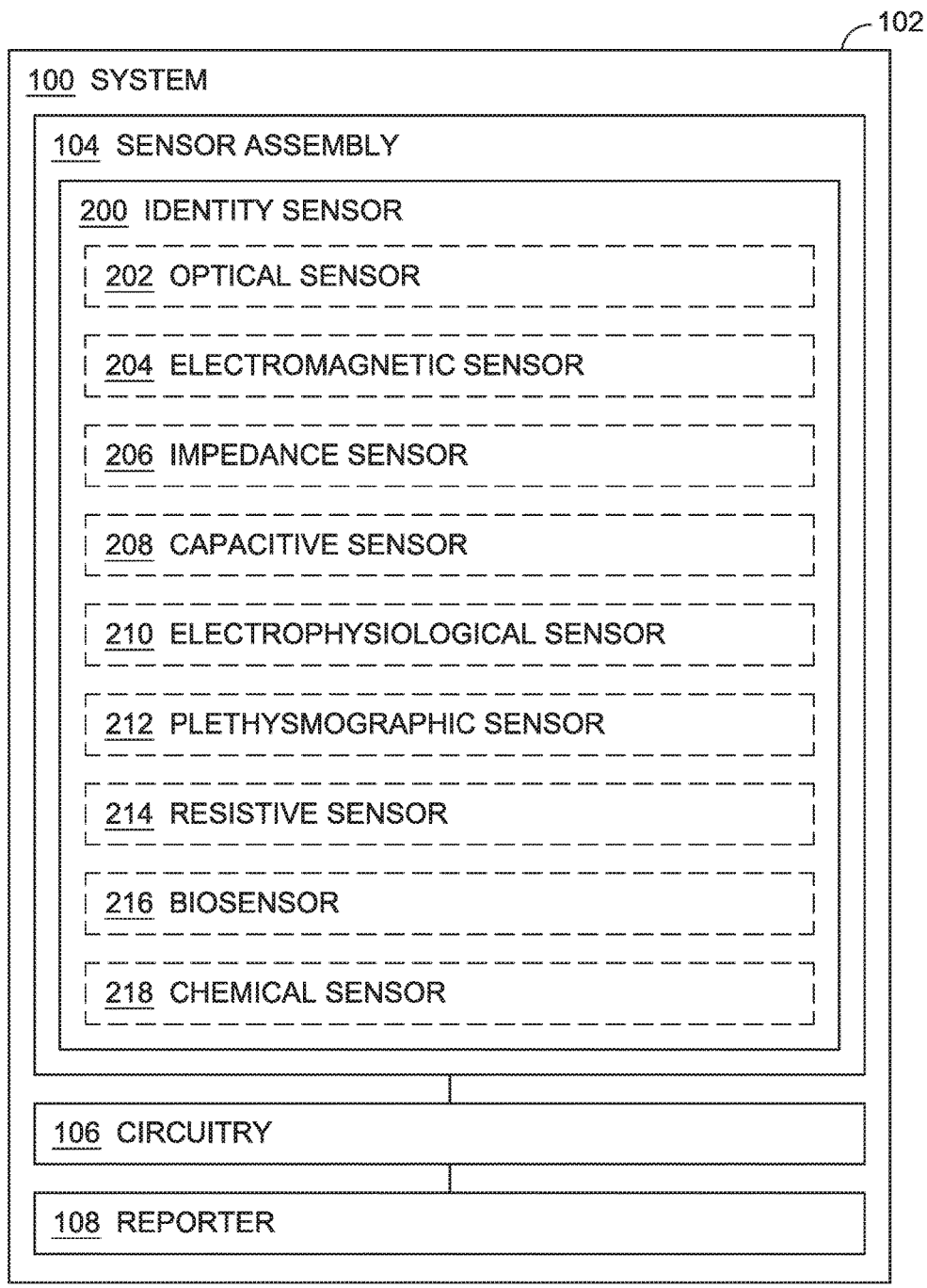
FIG. 2 is a schematic of an embodiment of a system such as shown in FIG. 1.
Figure 3:
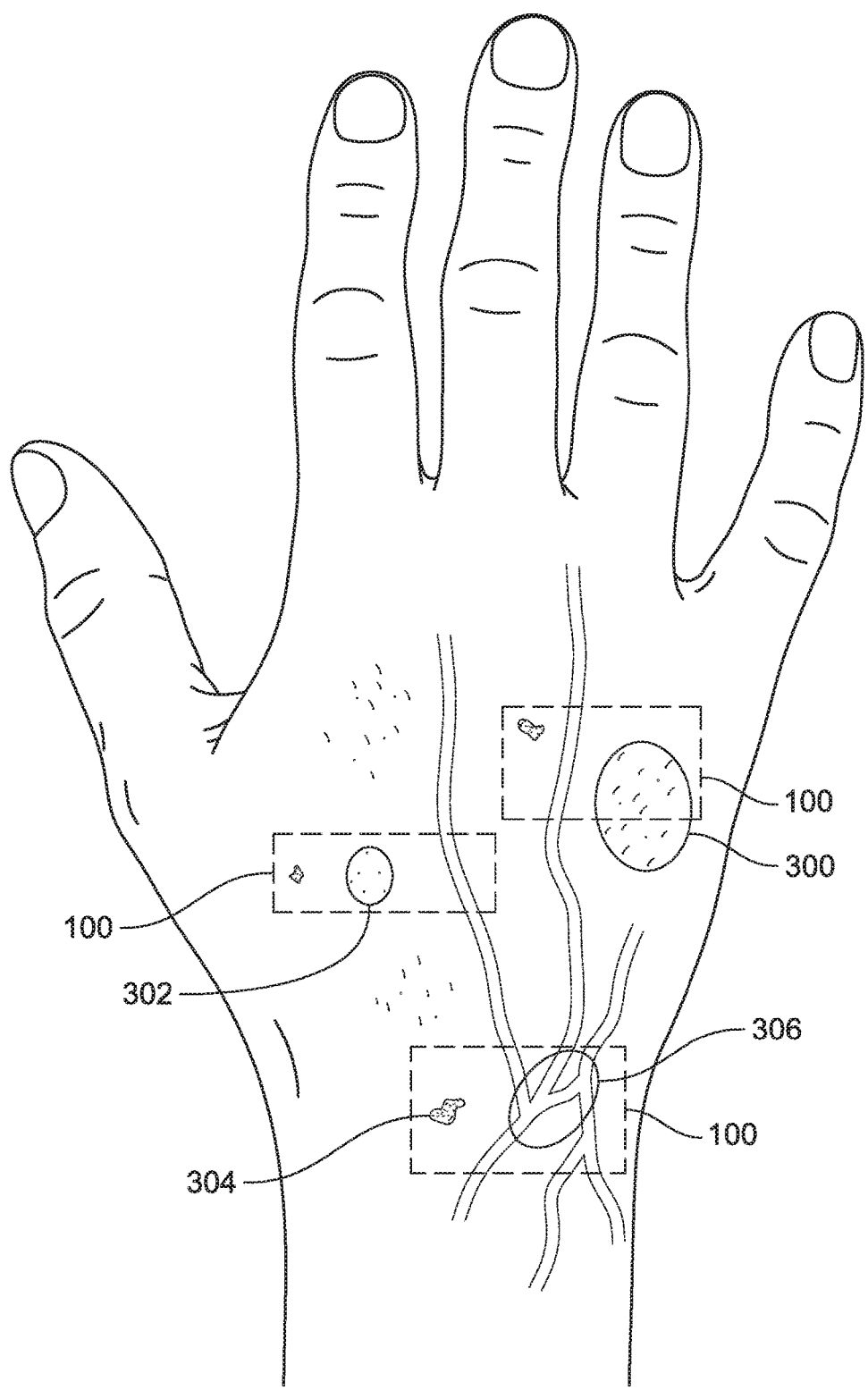
FIG. 3 is a schematic of an embodiment of a system such as shown in FIG. 1.

For example, as shown in FIG. 2, the sensor assembly 104 includes one or more identity sensors 200 configured to generate one or more identity sense signals associated with at least one physical characteristic of the individual subject. The identity sensor 200 can sense the physical characteristic to provide a basis for identification of the individual subject, or to provide an indication that the individual subject cannot be readily identified based on the observed physical characteristics. The identity sensor 200 can include, but is not limited to, one or more of an optical sensor 202, an electromagnetic sensor 204, an impedance sensor 206, a capacitive sensor 208, an electrophysiological sensor 210, a plethysmographic sensor 212, a resistive sensor 214, a biosensor 216, or a chemical sensor 218. The identity sensor 200 can generate the one or more identity sense signals based on measurement or sensing of one more physical characteristics of the individual subject, where the one or physical characteristics can include but are not limited to, skin topography features (e.g., pattern of skin surface, follicle pattern, pore pattern, pigmentation, etc.), vascular properties or layouts (e.g., arterial patterns, properties, or layouts; vein patterns, properties, or layouts; etc.), electric current pattern (e.g., photovoltaic current pattern), or skin resistivity measurement. For example, as shown in FIG. 3, the system 100 can be positioned on a skin surface of a body portion (shown as a top surface of a hand in FIG. 3), where the system 100 can detect via the identity sensor 200 one or more of a follicle pattern 300, a pore pattern 302, a skin pigmentation or distinctive skin mark 304, or a vascular pattern or layout 306. The identity sensor 200 can then generate one or more identity sense signals based on the structure of the particular sensor(s) of the sensor assembly 104 (e.g., optical sensor 202, electromagnetic sensor 204, impedance sensor 206, etc.), where such signals will correspond to the measured or sensed physical characteristics to facilitate in analysis of whether the identity of the individual subject can be determined. In an embodiment, the optical sensor 202 includes one or more optoelectronics generate the one or more identity sense signals based on measurement or sensing of one more physical characteristics of the individual subject. For example, the optoelectronics can include, but are not limited to, one or more polymer light-emitting diodes (PLEDs), one or more organic photodetectors (OPDs), or combinations thereof. In an embodiment, the optoelectronics include a plurality of polymer light-emitting diodes (PLEDs) configured to emit light of differing wavelengths (e.g., green, red, blue, etc.), which in combination with one or more organic photodetectors (e.g., having an active layer of poly(3-hexylthiophene) (P3HT):(6,6)-phenyl-C61-butyric acid methyl ester (PCBM)) are arranged as an ultraflexible reflective pulse oximeter.

Chemical sensors and biosensors (e.g., chemical sensor 218 and biosensor 216) can include aspects of physiological sensors, such that each of chemical sensors and biosensors can detect certain physiological conditions or parameters. For example, without limitation, a chemical sensor can detect a chemical signature of an analyte, for example an analyte of a physiological origin (e.g., a cellular compound, a secreted compound such as an antibody or a cytokine, or a metabolite) or an analyte of an exogenous origin (e.g., an ingested, inhaled, or topical substance, such as a drug, or a tagging or labeling compound). Examples of chemical sensors include, but are not limited to, sensors having recognition elements, electronic chip sensors, microbalance sensors, and near infrared spectrometers. A biosensor can detect a biochemical or biological element. Biosensors include, for example but are not limited to, sensors having a biological recognition element able to bind an analyte of interest (e.g., an aptamer-based microcantilever) and sensors utilizing an enzyme with recognition and reaction properties. In an embodiment, chemical sensors or biosensors can include molecular sensor or nanosensor aspects.

The sensor assembly 104 can be structured relative to the deformable substrate 102 such that at least a portion of the sensor assembly 104 is embedded within the deformable substrate 102, affixed to the deformable substrate 102, residing on the deformable substrate 102, printed directly onto the deformable substrate 102, or a combination thereof. For example, at least a portion of an identity sensor 200 can be embedded within the deformable substrate 102, can be affixed to the deformable substrate 102, can reside on the deformable substrate 102, can be directly printed on the deformable substrate 102, or a combination thereof. In an embodiment, the deformable substrate 102 can include one or more of a stretchable/flexible fabric, an elastomeric polymer, a hydrocolloid film, a membrane (e.g., a nanomembrane, such as a silicon nanomembrane), a gas-permeable elastomeric sheet, or other conformable material. In an embodiment, at least one of the sensor assembly 104, the circuitry 106, or the reporter 108 resides on the deformable substrate 102, such as residing on at least a portion of one or more of a stretchable/flexible fabric, an elastomeric polymer, a hydrocolloid film, a membrane (e.g., a nanomembrane, such as a silicon nanomembrane), a gas-permeable elastomeric sheet, or other conformable material. For example, at least a portion of at least one of the sensor assembly 104, the circuitry 106, or the reporter 108 can be printed directly onto at least a portion of the deformable substrate 102. In an embodiment, at least one of the sensor assembly 104, the circuitry 106, or the reporter 108 is embedded within the deformable substrate 102, such as embedded within at least a portion of one or more of a stretchable/flexible fabric, an elastomeric polymer, a hydrocolloid film, a membrane (e.g., a nanomembrane, such as a silicon nanomembrane), a gas-permeable elastomeric sheet, or other conformable material.

Figure 4:
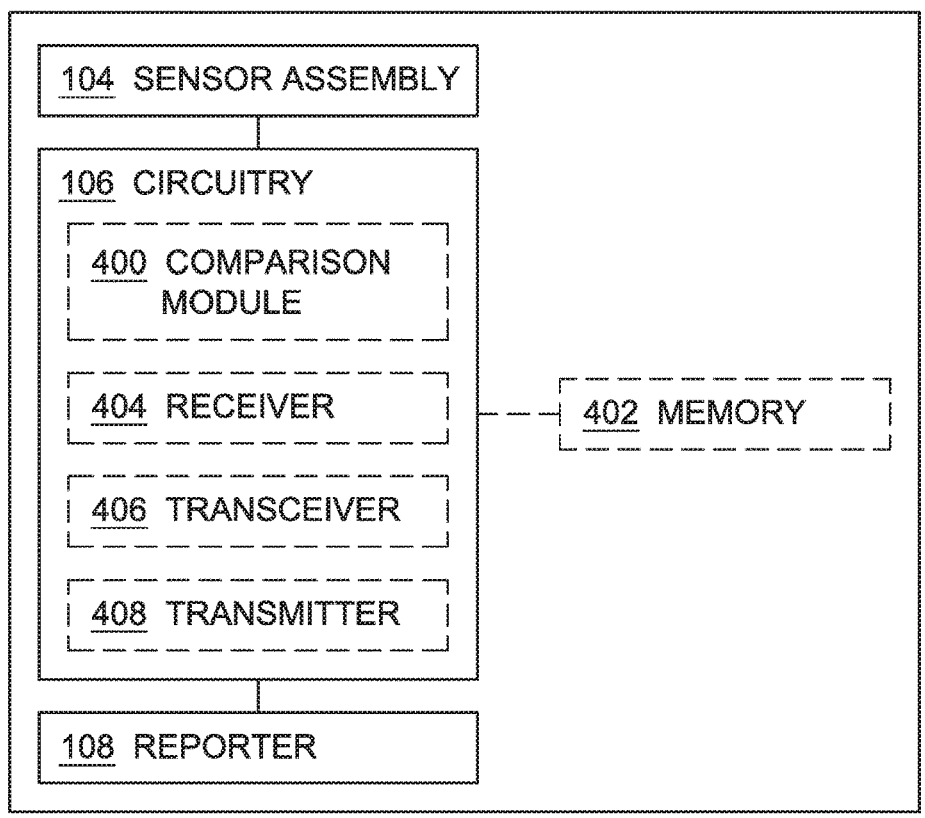
FIG. 4 is a schematic of an embodiment of a system such as shown in FIG. 1.

The circuitry 106 is configured to receive one or more identity sense signals (e.g., from the sensor assembly 104) associated with one or more physical characteristics of the individual subject on which the system 100 is positioned, and can provide analysis of the one or more identity sense signals. For example, in an embodiment, the circuitry 106 is operably coupled to the sensor assembly 104 such that the circuitry 106 is configured to receive the one or more identity sense signals from the one or more identity sensors 200 of the sensor assembly 104. In an embodiment, shown in FIG. 4, the circuitry 106 includes a comparison module 400 configured to compare the one or more identity sense signals generated by the sensor assembly 104 to reference data indicative of one or more physical characteristics associated with an identity of at least one individual to determine whether the one or more identity signals correspond to the identity of the at least one individual. In an embodiment, the reference data is stored in a computer memory device 402 which can include, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information maintained by the comparison module 400 and which can be accessed by the circuitry 106 or other associated accessing device.

The circuitry 106 includes components to process the one or more sense signals from the sensor assembly 104 and to provide instruction to the reporter 108 to generate one or more communication signals associated with the one or more identity sense signals, a comparison of the one or more identity sense signals with the one or more physical characteristics from reference data indicative with an identity of a particular individual, determinations made by the circuitry 106, or other information. For example, the circuitry 106 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In an embodiment, the circuitry 106 includes one or more ASICs having a plurality of predefined logic components. In an embodiment, the circuitry 106 includes one or more FPGAs having a plurality of programmable logic commands. The computer memory device can be integrated with the system 100, can be associated with an external device and accessible by the system 100 through wireless or wired communication protocols, or a combination thereof. For example, the reference data can be stored by the computer memory 702 coupled to the deformable substrate 102 of the system 100, can be accessible by the circuitry 106 via wireless means, or can be available to the circuitry 106 through another method, such as through a remote network, a cloud network, and so forth. In an embodiment, the circuitry 106 includes a receiver 404 or transceiver 406 (e.g., antenna, etc.) to receive the reference data information or other information (e.g., correspondence threshold information, programming information) to facilitate operation or control of the system 100 through wireless or wired communication protocols. For example, the receiver 404 can receive one or more communication signals from an external device associated with but not limited to, control programming, authorization parameters, reference data, or a query (e.g., a query to transmit information from the system 100 to the external device, a query to begin sensing of identity sense signals via the sensor assembly 104, etc.). In embodiments, the circuitry 106 can also include a transmitter 408 or transceiver (e.g., antenna, etc.) to send information amongst components of the system 100 or to components external the system, such as to communicate with an external device (e.g., external device 800 described herein). Such communication can include, for example, indications that the circuitry 106 is accessing one or more databases or memory devices storing reference or programming data, computational protocols, system updates, or the like.

The reference data includes data indicative of one or more physical characteristics associated with an identity of at least one individual. For example, the reference data can include, but is not limited to, a skin topography feature associated with an identity of an individual, a skin surface pattern associated with an identity of an individual, a follicle pattern associated with an identity of an individual, a pore pattern associated with an identity of an individual, a pigmentation pattern or characteristic associated with an identity of an individual, a vascular layout associated with an identity of an individual, an electric current pattern associated with an identity of an individual, a photovoltaic current pattern associated with an identity of an individual, a skin resistivity measurement associated with an identity of an individual, or the like. For example, the reference data can include one or more physical characteristics associated with a first person/individual, one or more physical characteristics associated with a second person/individual, one or more physical characteristics associated with a third person/individual, and so on. The circuitry 106 is configured to compare the identity sense signals from the sensor assembly 104 to the reference data, such that when the comparison is at or exceeds a threshold correspondence (e.g., within a predetermined confidence interval), the identity of the person/individual stored by the reference data can be attributed to the individual on which the system 100 is positioned. For example, if the reference data includes physical characteristic information for each of Bob, Jan, and Joe, the circuitry 106 can compare the identity sense signals from the sensor assembly 104 to determine whether the identity sense signals would correspond to the physical characteristic information of Bob, Jan, or Joe.

Figure 5:
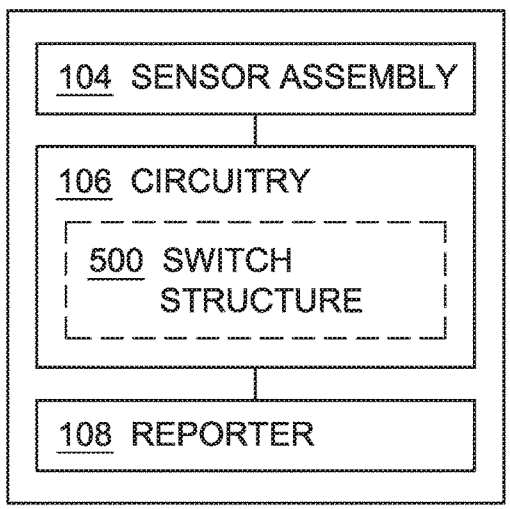
FIG. 5 is a schematic of an embodiment of a system such as shown in FIG. 1.

The circuitry 106 can coordinate operations of the system 100 based on analysis of the one or more identity sense signals, which can include but is not limited to, enabling or disabling certain operations or components of the system 100 based on whether the individual subject can be identified via the one or more identity sense signals. For example, in an embodiment, the circuitry 106 is configured to disable at least one component of the system 100 responsive to a correspondence between the one or more identity sense signals and the one or more physical characteristics associated with the identity of the at least one individual being below a threshold correspondence. The correspondence between the one or more identity sense signals and the one or more physical characteristics associated with the identity of the at least one individual can include a comparison by the circuitry 106 between the one or more identity sense signals and the one or more physical characteristics provided in the reference data (e.g., which can be linked or associated with certain identified individuals). As such, the circuitry 106 can disable functionality of a component of the system 100 where the individual subject on which the system 100 is positioned cannot be readily identified based on the comparison made by the circuitry 106. For example, in an embodiment, the circuitry 106 is configured to disable a power connection to the sensor assembly 104 responsive to the correspondence between the one or more identity sense signals and the one or more physical characteristics associated with the identity of the at least one individual being below the threshold correspondence. In an embodiment, the circuitry 106 is configured to disable a power connection to the reporter 108 responsive to the correspondence between the one or more identity sense signals and the one or more physical characteristics associated with the identity of the at least one individual being below the threshold correspondence. For example, in an embodiment, shown in FIG. 5, the circuitry 106 can include, or can be operably coupled to, a switch structure 500 switchable between an active configuration and an inactivate configuration responsive to control by the circuitry 106. The switch structure 500 can automatically disable, or can continue to disable, a power connection to one or more of the sensor assembly 104 or the reporter 108 (e.g., by providing a break in an electrical circuit providing power to the sensor assembly 104 or the reporter 108) when the individual subject on which the system 100 is positioned cannot be identified by the one or more identity sense signals, causing the circuitry 106 to manipulate the switch structure 500 to the inactive configuration, or causing the circuitry 106 to maintain the inactive configuration. Thus, when the individual subject cannot be identified, the individual subject would be precluded from operating the sensor assembly 104 or the reporter 108.

The circuitry 106 can be configured to permit operation of at least one component of the system 100 responsive to a correspondence between the one or more identity sense signals and the one or more physical characteristics associated with the identity of the at least one individual being at or above a threshold correspondence. The correspondence between the one or more identity sense signals and the one or more physical characteristics associated with the identity of the at least one individual can include a comparison by the circuitry 106 between the one or more identity sense signals and the one or more physical characteristics provided in the reference data (e.g., which can be linked or associated with certain identified individuals). As such, the circuitry 106 can enable functionality of a component of the system 100 where the individual subject on which the system 100 is positioned can be identified (e.g., within the threshold correspondence) based on the comparison made by the circuitry 106. For example, in an embodiment, the circuitry 106 is configured to activate a power connection to the sensor assembly 104 responsive to the correspondence between the one or more identity sense signals and the one or more physical characteristics associated with the identity of the at least one individual being at least at the threshold correspondence. In an embodiment, the circuitry 106 is configured to activate a power connection to the reporter 108 responsive to the correspondence between the one or more identity sense signals and the one or more physical characteristics associated with the identity of the at least one individual being at least at the threshold correspondence. For example, the switch structure 500 can automatically activate, or can continue to support, a power connection to one or more of the sensor assembly 104 or the reporter 108 (e.g., by closing a break in an electrical circuit providing power to the sensor assembly 104 or the reporter 108, by maintaining the operability of the electrical circuit providing power to the sensor assembly 104 or the reporter 108, etc.) when the individual subject on which the system 100 is positioned can be identified by the one or more identity sense signals, causing the circuitry 106 to manipulate the switch structure 500 to the active configuration, causing the circuitry to maintain the switch structure 500 in the active configuration, or the like. Thus, when the individual subject can be identified, the individual subject can operate the sensor assembly 104 or the reporter 108, the system 100 can maintain functionality, etc.

In an embodiment, the circuitry 106 is activated, controlled, or deactivated by gesture. For example, the circuitry 106 can receive one or more sense signals from a gesture sensor of the system (e.g., an accelerometer, a motion sensor, a proximity sensor, a contact sensor, or other sensor) indicative of a gesture performed by the individual subject, such as a gesture with the body portion on which the system is positioned, a body portion proximate to the body portion on which the system is positioned, or other body portion. For example, the gesture can include a wave, a pinch, a rub, a squeeze, a click, a lift, a flick, a shake, or other gesture configured to activate, control, or deactivate the circuitry 106 via the one or more sense signals from gesture sensor. The system 100 can store a correspondence between a particular gesture and a functionality of the circuitry. For example, a first gesture (e.g., a wave gesture) can correspond to execution of a first program or protocol (e.g., a reporting protocol to cause the circuitry 106 to instruct the reporter 108 to generate the one or more communication signals), a second gesture (e.g., a pinch gesture) can correspond to execution of a second program or protocol (e.g., a sensing protocol to cause the circuitry 106 to activate or deactivate the sensor assembly 104), and where a third gesture (e.g., a shake gesture) can correspond to execution of a third program or protocol (e.g., a power protocol to cause the system 100 to power up or power down), and so on.

Figure 6:
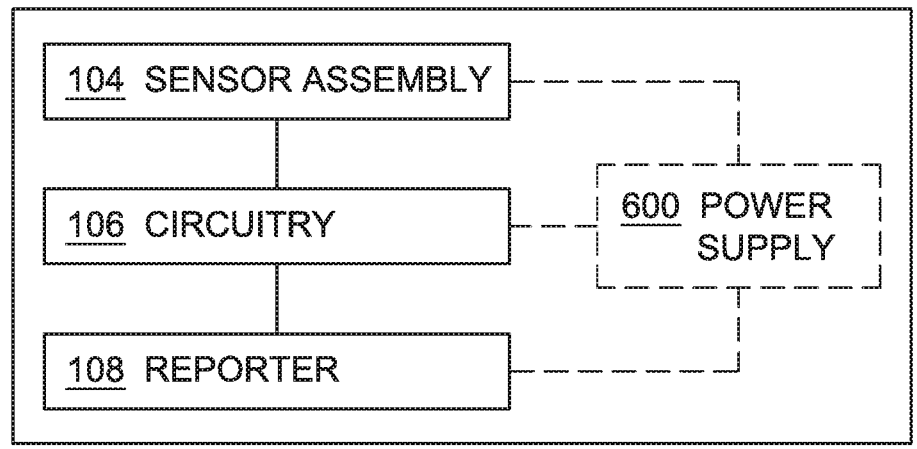
FIG. 6 is a schematic of an embodiment of a system such as shown in FIG. 1.

In an embodiment, as shown in FIG. 6, the system 100 includes a power supply 600 configured to provide power to one or more components of the system 100 including, but not limited to, the sensor assembly 104, the circuitry 106, and the reporter 108. For example, the power supply 600 can be a resident device component that is coupled to the deformable substrate 102. Examples of resident device components include, but are not limited to, batteries (e.g., a thin film battery, a microbattery), solar cells (e.g., silicon-based solar cells) configured to convert light energy into electrical energy for use by the components of the system 100, fuel cells, and energy harvesting devices (e.g., power devices configured to generate power from motion, such as motion of the body portion, motion of blood flow, and so forth). In embodiments, the power supply 600 includes one or more components positioned remotely from the deformable substrate 102 that transmit power signals via associated wireless power methods including, but not limited to, inductive coupling of power signals. In such embodiments, the system 100 includes one or more components positioned on the deformable substrate 102 configured to one or more of receive, process, and/or distribute the power signals that originate from components positioned remotely from the deformable substrate 102. For example, the system 100 can include a wireless power coil coupled to the deformable substrate 102 that is configured to receive a remote power signal, such as a remote power signal originating from a remote transmission coil. In an embodiment, the power supply 600 includes stretchable or flexible electronics. For example, the power supply 600 can include a silicon filamentary serpentine-shaped photovoltaic cell. For example, the power supply 600 can include filamentary serpentine-shaped inductive coils.

The reporter 108 of the system 100 is configured to generate one or more communication signals to report information associated with operation of the system 100. In an embodiment, the reporter 108 is operably coupled to the circuitry 106 and is configured to generate one or more communication signals responsive to instruction by the circuitry 106. The communication signals can be associated with the one or more identity sense signals generated by the sensor assembly 104 (e.g., via the one or more identity sensors 200), with a comparison of the one or more identity sense signals with the one or more physical characteristics associated with the identity of the at least one individual (e.g., as provided by the circuitry 106 to determine whether the one or more identity signals correspond to the identity of the at least one individual), or a combination thereof. For example, the reporter 108 can report that the individual on which the system 100 is placed corresponds to a first individual (e.g., it is Bob), the reporter 108 can report that the information transmitted is a second individual's physical characteristics (e.g., this information corresponds to the skin topography feature of Jan), the reporter 108 can report that the system 100 is unable to determine an identity of the individual (e.g., the physical characteristics measured by the sensor assembly 104 do not correspond to, or do not meet a threshold correspondence to, any of Bob, Jan, or Joe), or the like. In an embodiment, the communication signals are reportable to an external device or system (e.g., external device 800, described further herein). For example the external device or system can include, but is not limited to, a computing device, system or network (e.g., a personal computing device, an electronic health record, etc.), or an electronic device (e.g., an electronic game, an electronic controller such as on a vehicle or instrument, or other electronic equipment). In an embodiment, the system 100 can transmit the one or more communication signals to a computing device having at least one of circuitry or programming that collects data from one or more wearable sensors that are part of the system 100 or are otherwise associated with the individual on which the system 100 is positioned, so that the computing device can associate data within the communication signals with the individual. The system 100, via the reporter 108, can transmit identity information to an electronic controller equipped with authorization capabilities for employment in authorizing use of one or more devices, programs, device functionalities, or the like, by the identified individual. For example, the system 100 can transmit information that the individual is identified as Bob, whereby the electronic controller can facilitate use of one or more devices, programs, device functionalities by Bob, according to his identity.

Figure 7:
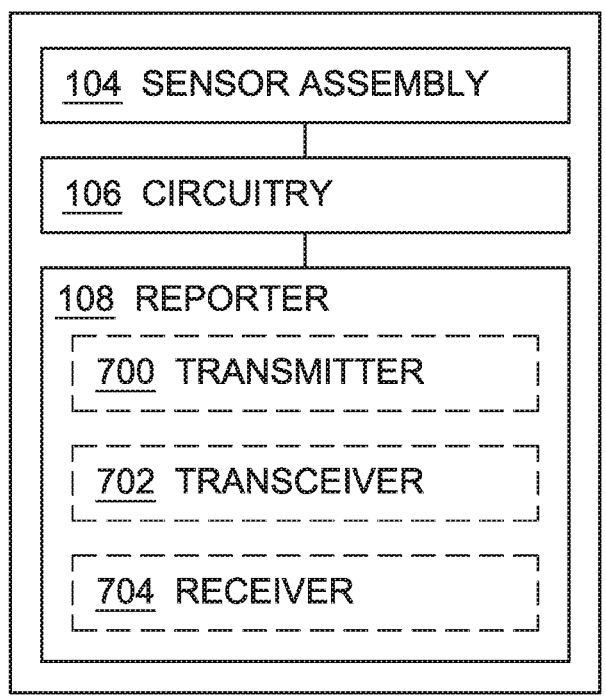
FIG. 7 is a schematic of an embodiment of a system such as shown in FIG. 1.

In an embodiment, shown in FIG. 7, the reporter 108 includes one or more of a transmitter 700, a transceiver 702, or a receiver 704. For example, the reporter 108 can include an antenna structure configured to at least one of transmit the one or more communication signals (e.g., via the transmitter 700, the transceiver 702, etc.) or receive one or more communication signals from an external device (e.g., via the transceiver 702, the receiver 704, etc.). The one or more communication signals from the external device can include but are not limited to, control programming, authorization parameters, reference data, or a query (e.g., a query to transmit information from the system 100 to the external device). In an embodiment, the sensor assembly 104 includes one or more of a transceiver (e.g., transceiver 702) or a receiver (e.g., receiver 704) configured receive one or more communication signals from an external device. For example, the one or more communication signals from the external device can include but are not limited to, control programming, authorization parameters, reference data, or a query (e.g., a query to begin sensing physical characteristics of the individual subject on which the system 100 is positioned).

In an embodiment, the system 100 includes a unique identifier associated with at least one of the deformable substrate 102, the sensor assembly 104, the circuitry 106, or the reporter 108. The unique identifier can facilitate identifying a source of data, a source of communication signals, or the like, such as when multiple identification devices or systems 100 are utilized in combination to identify a plurality of individual subjects or when multiple identification devices or systems 100 are utilized by an individual subject, e.g., over a period of time. For example, when the reporter 108 generates the one or more communication signals for transmission (e.g., to an external device), the one or more communication signals can be associated with or can include the unique identifier to identify the source of the one or more communication signals, which in turn can be associated with a particular identity of an individual on which the system 100 is positioned. The external device can therefore associate the identity of the individual with the particular device in future communications, actions, queries, and the like. When multiple identification devices or systems 100 are utilized by the individual subject the use of such identification devices or systems 100 can be tracked via the unique identifier associated with each identification device or system. For example, the unique identifier can designate a source for communications, measurements, identifications, etc. as being directed to a specific identification device or system 100 (e.g., a lot number), where the communications can be tracked sequentially (when multiple identification devices or systems 100 are utilized by the individual subject over a period of time), in parallel (when multiple identification devices or systems 100 are utilized by the individual subject at a given time), or a combination thereof (when multiple identification devices or systems 100 are utilized by the individual subject over a period of time and at a given time).

Figure 8:
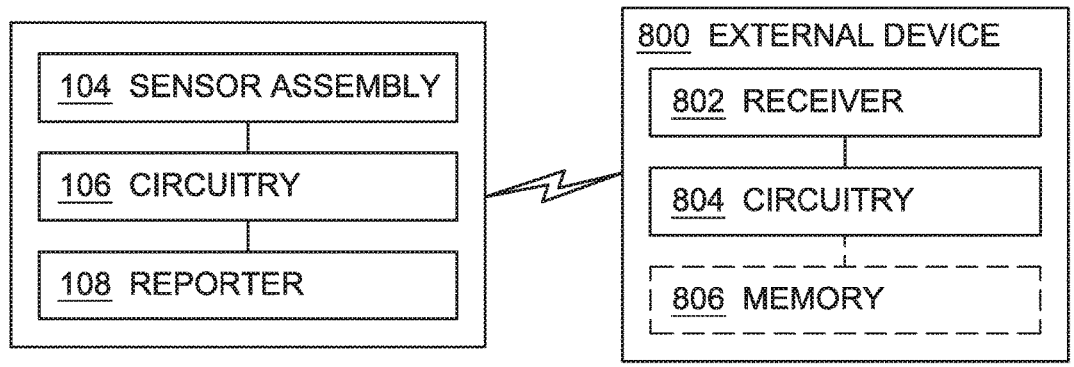
FIG. 8 is a schematic of an embodiment of a system such as shown in FIG. 1.

In an embodiment, shown in FIG. 8, the system 100 further includes an external device or system (referred to herein as external device 800) configured to receive communications from the reporter 108 for analysis by the external device 800. The external device 800 can include a receiver 802 (e.g., receiving antenna, transceiver, etc.) configured to receive the one or more communication signals from the reporter 108. The external device 800 can also include circuitry 804 configured to compare the one or more communication signals with one or more authorization parameters associated with one or more users authorized to operate the external device 800. For example, the external device 800 can include, or can access, a computer memory device 806 that maintains data associated with authorization parameters pertinent to operation of the external device 800. The authorization parameters can include but are not limited to, a list of identified individuals, identities, devices, or systems authorized to operate at least a portion of features of the external device 800, a list of reference physical characteristics for one or more users authorized to operate the external device 800, a list of functionalities of the external device 800 that identified individuals are authorized to utilize, or the like. For example, the external device 800 can receive the communication signals from the reporter 108 indicating an identity of the individual subject on whom the deformable substrate 102 is positioned, whereby the external device 800 can compare (e.g., via the circuitry 804) the identity of the individual with the authorization parameters stored in the memory 806 to determine whether the identified individual is authorized to operate the external device 800, to determine which functionalities of the external device 800 the identified individual is authorized to operate, or the like. As another example, where the authorization parameters includes a list of identified devices or systems, such devices or systems can automatically operate the portion of features of the external device 800, such as without interaction with the individual subject or other individual. The external device 800 can include but is not limited to, a communication device or electronic equipment, such as one or more of a mobile communication device or a computer system including, but not limited to, mobile computing devices (e.g., hand-held portable computers, Personal Digital Assistants (PDAs), laptop computers, netbook computers, tablet computers, or so forth), mobile telephone devices (e.g., cellular telephones and smartphones), devices that include functionalities associated with smartphones and tablet computers (e.g., phablets), portable game devices, portable media players, multimedia devices, satellite navigation devices (e.g., Global Positioning System (GPS) navigation devices), e-book reader devices (eReaders), Smart Television (TV) devices, surface computing devices (e.g., table top computers), Personal Computer (PC) devices, devices that employ touch-based human interfaces, currency-handling devices (e.g., automated teller machines (ATMs), cash registers, coin/bill counters and sorters, credit/debit card readers, etc.), a motorized vehicle or control systems thereof (e.g., car, truck, motorcycle, boat, snowmobile, airplane, helicopter, etc.), exercise facilities or equipment, a home security system, an electronic medication dispenser (e.g., pill dispenser), medical treatment facilities or equipment (e.g., patient suites, surgical suites, surgical equipment, etc.), rental equipment with a user interface (e.g., video rentals, audio rentals, etc.), transportation security terminals (e.g., airport security terminal, train security terminal, ferry security terminal, etc.), personnel-tracking equipment, heavy or specialized machinery, specialized tools, safety equipment, security equipment (e.g., a lock or access point), medical equipment (e.g., drug delivery devices or surgical tools), or personal equipment or clothing having customizable electronic features. The reporter 108 can communicate (e.g., send and receive communication signals) with the external device 800 via one or more connected or wireless communication mechanisms including, but not limited to acoustic communication signals, sound communication signals (e.g., audible, inaudible, or combinations thereof), optical communication signals, radio communication signals, infrared communication signals, ultrasonic communication signals, electric signals (e.g., via a conduction pathway between a component of the system 100 and the external device 800), and the like. In an embodiment, one or more of the sensor assembly 104 or the circuitry 106 can receive communication signals from the external device 800. For example, the external device 800 (e.g., a cellular or network-based device) can transmit one or more communication signals to one or more of the sensor assembly 104 or the circuitry 106, where such communication signals can initiate or terminate particular functionalities of the sensor assembly 104 or circuitry 106 (e.g., turn on/off), provide programming information, provide updated functionalities, provide or update comparison threshold values or reference data, or the like. In an embodiment, the circuitry 106 directs the reporter 108 to generate the one or more communication responsive to a query from the external device 800. In an embodiment, the reporter 108 generates the one or more communication signals responsive to instruction by the circuitry 106 without any dependence or communication from the external device 800. For example, the reporter 108 can generate the one or more communication signals regardless of whether the external device 800 is capable of receiving the communication signals. In such instances, the communication signals generated by the reporter 108 can be stored in memory of the system 100, where the stored communication signals can be utilized later (e.g., to program one or more new systems 100, external devices 800, etc.).

In an embodiment, one or more of the sensor assembly 104, the circuitry 106, or the reporter 108 facilitates interaction between the system 100 and one or more other devices or systems resident on the body of the individual on which the system 100 is positioned. For example, the external device 800 can include one or more devices or systems (e.g., one or more sensors, computing devices, or the like) that also reside on the individual on which the system 100 is positioned. In an embodiment, the system 100 includes the one or more other devices or systems resident on the body of the individual, such as additional sensing devices communicatively coupled with one or more of the sensor assembly 104, the circuitry 106, or the reporter 108. For example, when a sensing device resident on the body of the individual is active (e.g., a heart rate monitor), the output of the sensing device can be associated with the identity of the individual by the association between the sensing device resident on the body and the activities of one or more of the sensor assembly 104, the circuitry 106, or the reporter 108 (e.g., the heart rate measured by the heart rate monitor can be associated with the identity of individual on which the devices or systems are positioned).

Figure 9:
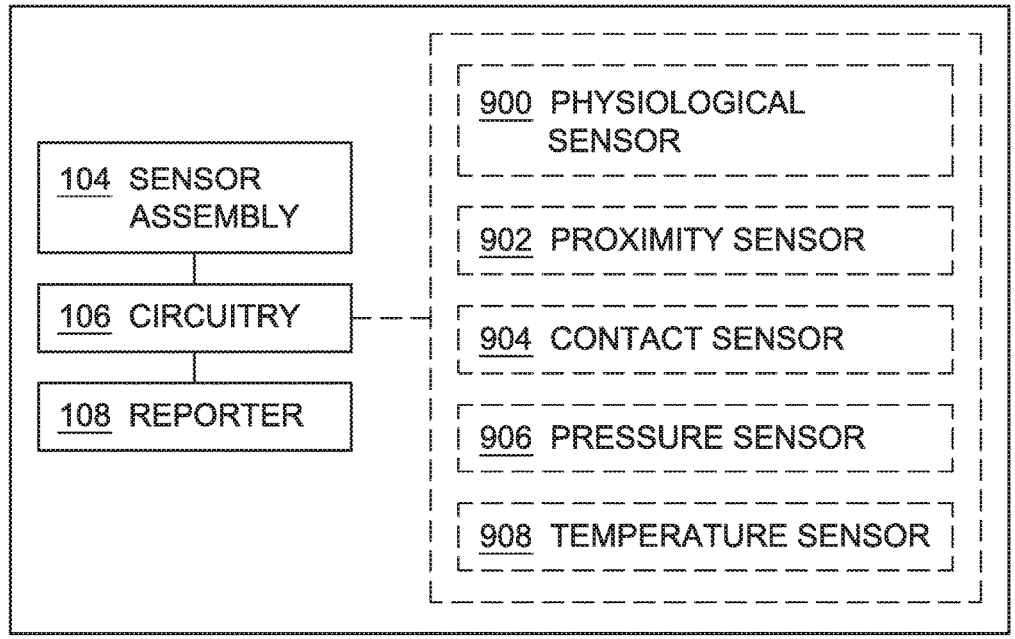
FIG. 9 is a schematic of an embodiment of a system such as shown in FIG. 1.

The system 100 can also include other sensors to provide functionalities independent of identification, supportive of identification, or the like. For example, in an embodiment, shown in FIG. 9, the system 100 includes one or more of a physiological sensor 900, a proximity sensor 902, a contact sensor 904, a pressure sensor 906, or a temperature sensor 908. In an embodiment, one or more of the physiological sensor 900, the proximity sensor 902, the contact sensor 904, the pressure sensor 906, or the temperature sensor 908 can provide sense signals indicative of whether the deformable substrate 102 is attached to, maintained against, or otherwise in contact with a skin surface of the individual. For example, the circuitry 106 can receive the sense signals from one or more of the physiological sensor 900, the proximity sensor 902, the contact sensor 904, the pressure sensor 906, or the temperature sensor 908 and can activate the sensor assembly 104 to begin identification of the individual subject responsive to confirmation of the presence of the deformable substrate 102 on the skin surface.

Figure 10:
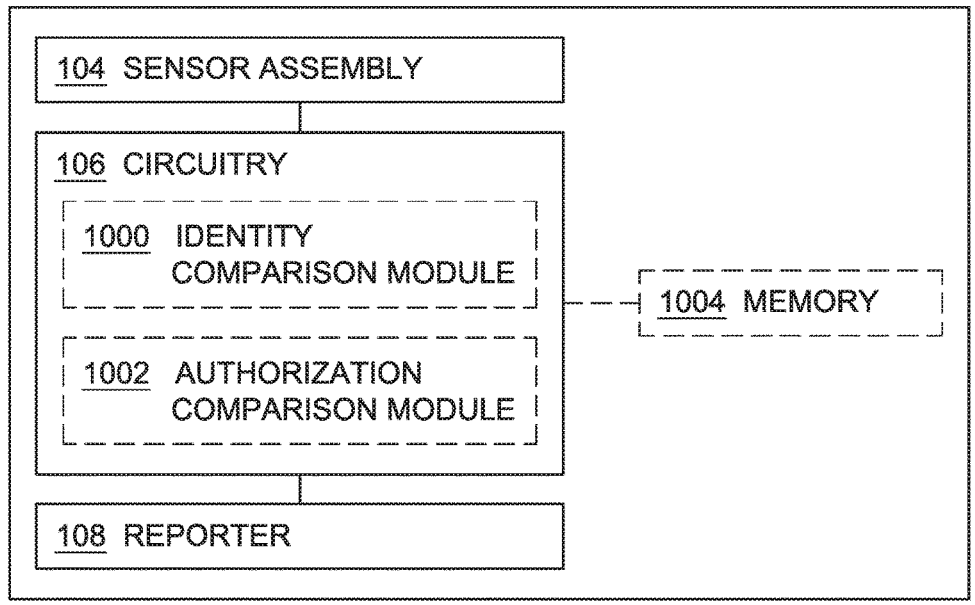
FIG. 10 is a schematic of a system for identification of an individual and authorization of an identified individual using conformable electronics.

In an embodiment, shown in FIG. 10, the circuitry 106 includes an identity comparison module 1000 and an authorization comparison module 1002. The identity comparison module 1000 is configured to compare the one or more identity sense signals generated by the sensor assembly 104 to reference data indicative of one or more physical characteristics associated with an identity of at least one individual to determine whether the one or more identity sense signals correspond to the identity of the at least one individual. For example, the identity comparison module 1000 can include structure and functionality similar to, or the same as, the comparison module 400 described herein. The reference data indicative of one or more physical characteristics associated with an identity of at least one individual can be stored in a computer memory device 1004 accessible by the circuitry 106, the identity comparison module 1000, or the authorization comparison module 1002. For example, the computer memory device 1004 can store data associated with a list of identities (e.g., names of individuals) having associated physical characteristics attributable to the particular identity (e.g., a skin topography feature associated with and unique to a first identity, a skin topography feature associated with and unique to a second identity, and the so forth). The authorization comparison module 1002 is configured to compare at least one of the one or more identity sense signals or the identity of the at least one individual with one or more authorization parameters. The authorization parameters can include but are not limited to, a list of identified individuals or identities authorized to operate at least a portion of features of the system 100, a list of identified authorized individuals or identities under which at least a portion of features of the system 100 (e.g., reporter 108) will function, a list of identified individuals or identities authorized to operate at least a portion of features of an external device (e.g., external device 800), a list of reference physical characteristics for one or more users authorized to operate an external device (e.g., external device 800), a list of functionalities of an external device (e.g., external device 800) that identified individuals are authorized to utilize, or the like.

In an embodiment, the reporter 108 is configured to generate the one or more communication signals responsive to instruction by the circuitry 106, where the one or more communication signals are associated with a comparison of at least one of the one or more identity sense signals with the one or more authorization parameters or the identity of the at least one individual with the one or more authorization parameters. For example, instances where the one or more communication signals are based on a comparison of one or more identity sense signals with the one or more authorization parameters, the authorization comparison module 1002 can directly compare the one or more identity sense signals with authorization parameters stored in the memory 1004. The authorization parameters can include a list of physical characteristics of authorized individuals, such that when the identity sense signals match the physical characteristics of authorized individuals stored in memory, the individual subject can be authorized. For example, authorization can include, but is not limited to, the individual being authorized to utilize the system 100 or to use an external device (e.g., where that individual subject substantially matches one identity of the list of individuals authorized to operate the external device), or the system 100 can function fully (e.g., can transmit information) or a portion of the functionalities of the system 100 to which the authorized individual is permitted to utilized are enabled. When the one or more communication signals are based on a comparison of the identity of the at least one individual with the one or more authorization parameters, the identity comparison module 1000 can first identity the individual based on the one or more identity sense signals, whereby the authorization comparison module 1002 can determine whether the identified authorized individual is (e.g., by comparing the identity to reference data having a list of authorized individuals or identities). In an embodiment, when the one or more authorization parameters corresponds to a single authorized user, the identity comparison module 1000 and the authorization comparison module 1002 can be incorporated as a single module for automatic authentication after identification.

Figure 11:
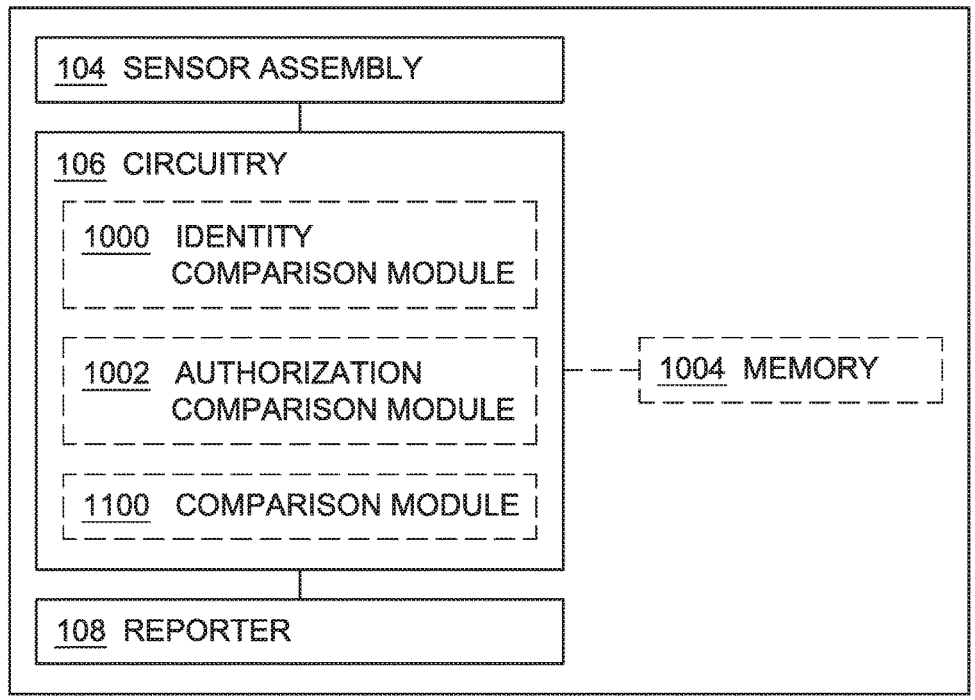
FIG. 11 is a schematic of an embodiment of a system such as shown in FIG. 10.

In an embodiment, shown in FIG. 11, the circuitry 106 includes a comparison module 1100 configured to compare the one or more identity sense signals generated by the sensor assembly 104 to reference data indicative of one or more physical characteristics associated with a physical state of the individual to determine whether the individual subject is authorized to operate an external device. For example, the memory 1004 can store reference data associated with physical states including but not limited to, a vital status (e.g., physiological reference data indicative of a living status or a deceased status, physiological data associated with a distress or stress status, or the like) or a functional status (e.g., a physical status, a mental status, or the like). In an embodiment, the comparison module compares sense signals from other sensors of the system (e.g., one or more of the physiological sensor 900, the proximity sensor 902, the contact sensor 904, the pressure sensor 906, or the temperature sensor 908) to determine the vital status or the functional status of the individual. The reference data indicative of one or more physical characteristics associated with a functional status can include but are not limited to, chemical or biological indicators of inebriation or intoxication (e.g., by drugs or alcohol), the presence or absence of a substance (e.g., a toxin, a poison, a prescription medication), a blood oxygenation level, a movement, pattern of movement, or absence of movement (e.g., as indicators of a state of consciousness or of compromised fine motor skills), or so forth. The vital status or the functional status can serve as an indicator as to whether an identified individual is in a state suitable for operation of the external device. For example, while the individual subject may be identified and authorized to use a device, the current status of the individual may preclude total or partial operation of the external device. For example, the sensors of the system 100 may detect that the individual does not have sufficient levels of medication in their bloodstream (e.g., a person with tremors or seizures) to safely operate a motorized vehicle for an extended period of time. In an embodiment, the circuitry 106 is configured to prevent authorization of the individual subject to operate at least a portion of the external device responsive to a correspondence between the one or more identity sense signals and the reference data indicative of the one or more physical characteristics associated with the functional status of the individual being above a functional threshold correspondence. For example, the functional threshold correspondence can be related to a safety threshold of a physical characteristic for operation of the external device (e.g., a blood alcohol content, a medication level, etc.). In an embodiment, the circuitry 106 prevents authorization of the individual subject by not instructing the reporter 108 to generate or transmit the one or more communication signals. In an embodiment, the circuitry 106 can permit partial authorization of operation of the external device, such that only a subset of functionalities of the external device is available to the individual for operation. For example, if an individual is identified and authorized to use a smart phone device, and that individual is determined to be intoxicated or to otherwise have a diminished functional status, the circuitry 106 can permit phone calls or web browsing functionalities, but prevent financial transaction functionalities.

Figure 12:
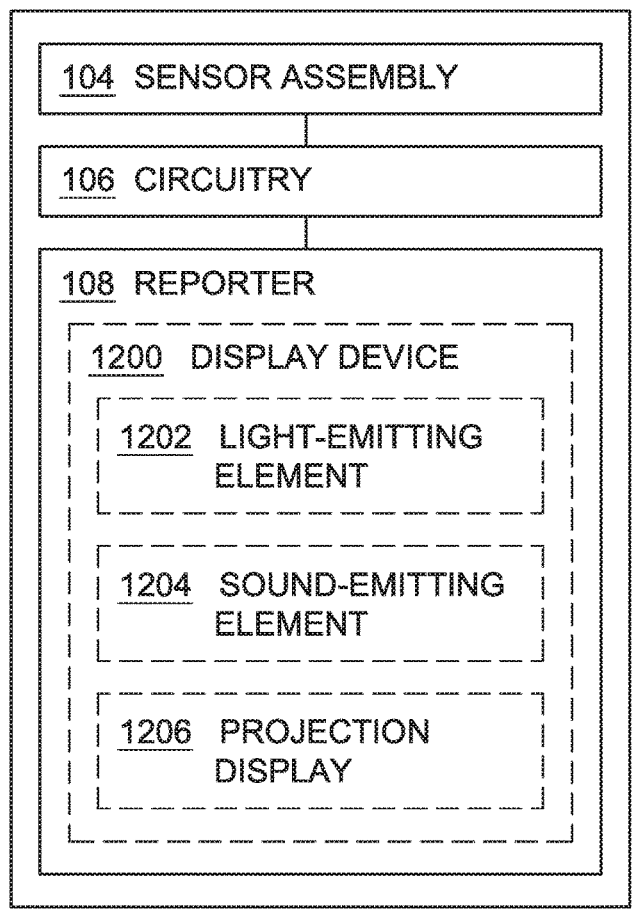
FIG. 12 is a schematic of an embodiment of a system such as shown in FIGS. 1 and 10.

In an embodiment, shown in FIG. 12, the reporter 108 includes a display device 1200 configured to provide a visual indication associated with an output of the reporter 108. For example, the display device 1200 can include one or more light-emitting elements 1202 (e.g., light-emitting diodes, polymer light-emitting diodes (PLEDs), lasers, or other light source(s)) configured to provide a predetermined pattern of light corresponding to a comparison between at least one of the one or more identity sense signals with the one or more authorization parameters or the identity of the at least one individual with the one or more authorization parameters. The predetermined pattern of light can include patterns associated with light intensity or brightness, color, shapes, or other characteristics discernable between distinct patterns. In an embodiment, the predetermined pattern includes a first pattern associated with a correspondence between at least one of the one or more identity sense signals with the one or more authorization parameters or the identity of the at least one individual with the one or more authorization parameters being below a threshold correspondence (e.g., the physical characteristics measured by the sensor assembly 104 do not correspond to an authorized individual), and the predetermined pattern includes a second pattern associated with a correspondence between at least one of the one or more identity sense signals with the one or more authorization parameters or the identity of the at least one individual with the one or more authorization parameters being at least at the threshold correspondence (e.g., the physical characteristics measured by the sensor assembly 104 correspond to an authorized individual). For example, the reporter 108 can display via the display device a first pattern (e.g., a first intensity, a first color, a first shape, etc.) if the individual subject is not authorized to operate the external device, and can display a distinct second pattern (a second intensity, a second color, a second shape, etc.) if the individual subject is authorized to operate the external device. The system 100 can also include one or more photodetectors, such as one or more organic photodetectors (OPDs), to detect light from the display device 1200 and/or the sensor assembly 104, such as light reflected by or refracted from a body portion. For example, the system 100 can include an organic photodetector comprising an active layer of poly(3-hexylthiophene) (P3HT):(6,6)-phenyl-C61-butyric acid methyl ester (PCBM).

In an embodiment, the display device 1200 can include one or more sound-emitting elements 1204 (e.g., speaker, tone-source, or other sound source(s)) configured to provide a predetermined pattern of sound corresponding to a comparison between at least one of the one or more identity sense signals with the one or more authorization parameters or the identity of the at least one individual with the one or more authorization parameters. The predetermined pattern of sound can include patterns associated with sound intensity, audible and inaudible phases, or other characteristics discernable between distinct patterns. In an embodiment, the predetermined pattern includes a first pattern associated with a correspondence between at least one of the one or more identity sense signals with the one or more authorization parameters or the identity of the at least one individual with the one or more authorization parameters being below a threshold correspondence (e.g., the physical characteristics measured by the sensor assembly 104 do not correspond to an authorized individual), and the predetermined pattern includes a second pattern associated with a correspondence between at least one of the one or more identity sense signals with the one or more authorization parameters or the identity of the at least one individual with the one or more authorization parameters being at least at the threshold correspondence (e.g., the physical characteristics measured by the sensor assembly 104 correspond to an authorized individual). For example, the reporter 108 can display via the display device a first pattern (e.g., a first intensity, a first audible/inaudible pattern, etc.) if the individual subject is not authorized to operate the external device, and can display a distinct second pattern (a second intensity, a second audible/inaudible pattern, etc.) if the individual subject is authorized to operate the external device.

In an embodiment, the display device 1200 includes a projection display 1206 configured to provide a visual indication associated with an output of the reporter 108. For example, the projection display 1206 can be configured to provide a projected image (e.g., projected onto a skin surface, onto a clothing item or garment, onto a wall or support surface, onto a screen, etc.) corresponding to a comparison between at least one of the one or more identity sense signals with the one or more authorization parameters or the identity of the at least one individual with the one or more authorization parameters.

In an embodiment, the circuitry 106 is configured to determine whether the deformable substrate 102 has been removed from the skin surface of the individual subject. For example, the system 100 can include, as a part of the sensor assembly 104, distinct from the sensor assembly 104, or a combination thereof, one or more of a strain gauge or a proximity sensor configured to sense whether the deformable substrate 102 has been removed from the skin surface of the individual subject. For example, the system 100 can include a computer memory device storing reference data associated with strain or distance measurements corresponding to removal of the deformable substrate 102 from a skin surface. The circuitry 106 can compare the output from the strain gauge or proximity sensor to such reference data to determine whether the deformable substrate 102 has been removed. In an embodiment, the circuitry 106 is configured to determine whether the deformable substrate 102 has been applied to a skin surface that differs from the skin surface of the individual subject. For example, the system 100 can store in a computer memory device the one or more identity sense signals obtained by the sensor assembly 104 at a first time, whereby the circuitry 106 can compare one or more identity sense signals obtained by the sensor assembly 104 at a second time to the stored identity sense signals obtained by the sensor assembly 104 at the first time to determine whether the signals substantially differ. If the signals are directed to a skin property, a substantial difference between signals obtained at differing times can indicate that the skin surface differs between the first time and the second, which can indicate that the system 100 was transferred between different individuals between the first time and the second time.

The reporter 108 can generate the one or more communication signals responsive to a variety of scenarios involving one or more of identification or authorization. For example, in an embodiment, the one or more communication signals generated by the reporter 108 correspond to a lack of authorization of the individual subject to operate an external device responsive to a correspondence between the one or more identity sense signals and the reference data indicative of one or more physical characteristics associated with the identity of the at least one individual being below a threshold correspondence. For example, when the circuitry 106 (e.g., via the identity comparison module 1000) is unable to identify the individual subject on which the system 100 is positioned, the reporter 108 can report via the communication signals that the individual subject is not authorized to operate the external device on the basis that such individual subject is not recognizable. In an embodiment, when the circuitry 106 (e.g., via the identity comparison module 1000) is unable to identify the individual subject on which the system 100 is positioned, the circuitry 106 prevents generation of the communication signals by the reporter 108 (e.g., no instruction from the circuitry 106 to the reporter 108 regarding generation of the one or more communication signals). In an embodiment, the one or more communication signals generated by the reporter 108 correspond to authorization of the individual subject to operate an external device responsive to both of (i) a correspondence between the one or more identity sense signals and the reference data indicative of one or more physical characteristics associated with the identity of the at least one individual being at least at a threshold correspondence and (ii) a correspondence between at least one of the one or more identity sense signals or the identity of the at least one individual with one or more authorization parameters being at least at a threshold correspondence. For example, when the circuitry 106 is able to identify the individual subject on which the system 100 is positioned (e.g., via the identity comparison module 1000) and the circuitry 106 is able to authorize the individual subject on which the system 100 is positioned for operation of the external device (e.g., via the authorization comparison module 1002), the reporter 108 can report via the communication signals that the individual subject is authorized to operate the external device.

In an embodiment, the reporter 108 is configured to provide a static output of communication signals. In an embodiment, the reporter 108 is configured to continuously generate the one or more communication signals. In an embodiment, the reporter 108 is configured to provide a dynamic output of communication signals. In an embodiment, the reporter 108 is configured to generate the one or more communication signals responsive to a query from an external device (e.g., external device 800). In an embodiment, the reporter 108 is configured to generate the one or more communication signals responsive to a proximity between the reporter 108 and an external device (e.g., external device 800). For example, the system can include a proximity sensor (e.g., proximity sensor 902) configured to generate sense signals indicative of proximity between the reporter 108 and an external device (e.g., external device 800). The circuitry 106 can compare the sense signals from the proximity sensor to reference data (e.g., a threshold proximity) to determine whether the reporter 108 and the external device 800 are close enough to begin transmission of communication signals from the reporter 108 to the external device 800, and instruct the reporter 108 to generate the one or more communication signals when it is determined that the reporter 108 and the external device 800 are within a threshold proximity.

Figure 13:
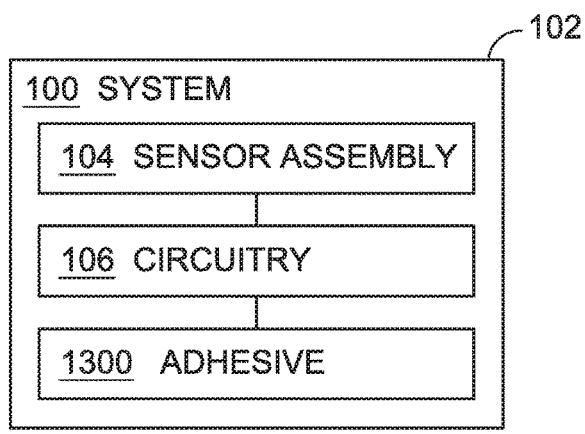
FIG. 13 is a schematic of an embodiment of a system such as shown in FIGS. 1 and 10.

In an embodiment, shown in FIG. 13, the system 100 includes the deformable substrate 102, the sensor assembly 104, the circuitry 106, and an adhesive 1300. The adhesive 1300 is coupled to a surface of the deformable substrate 102 and configured to adhere the deformable substrate 102 to the skin surface of the individual subject. The adhesive 1300 is configured to transition from a first state (e.g., an adhesive state) to a second state (e.g., a non-adhesive state) responsive to one or more energy signals (e.g., electric signals, thermal signals, magnetic signals, light signals, etc.) from the circuitry 106. In an embodiment, the circuitry 106 is configured to generate the one or more energy signals responsive to a correspondence between the one or more identity sense signals and the one or more physical characteristics associated with the identity of the at least one individual being below a threshold correspondence. For example, if the circuitry 106 cannot determine the identity of the individual subject on whom the system 100 is positioned (e.g., via one or more of the comparison module 400 or the identity comparison module 1000), the circuitry 106 generates the one or more energy signals to transition the adhesive 1300 from an adhesive state to a non-adhesive state. When in the non-adhesive state, the adhesive 1300 lacks sufficient ability (e.g., adhesive properties, tackiness, adhesion properties, or the like) to keep the deformable substrate 102 secured in place relative to the skin surface of the individual subject (e.g., a low adhesive state). Thus, when the adhesive 1300 is in the non-adhesive state, the system 100 can lose functionality or operability with respect to an individual subject that cannot be readily identified.

Figure 14:
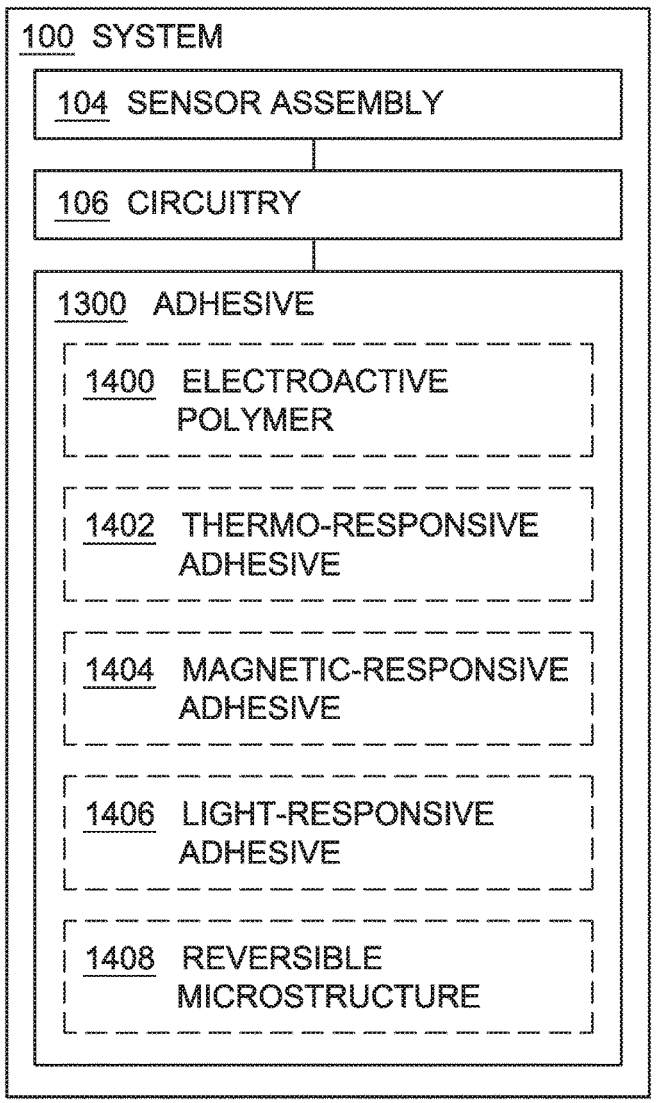
FIG. 14 is a schematic of an embodiment of a system such as shown in FIGS. 1 and 10.

In an embodiment, shown in FIG. 14, the adhesive 1300 can include one or more of an electro-responsive adhesive, such as an electroactive polymer 1400, a thermo-responsive adhesive 1402, a magnetic-responsive adhesive 1404, a light-responsive adhesive 1406, or a reversible microstructure 1408. The electroactive polymer 1400 can be actuatable by the one or more energy signals from the circuitry 106 to provide reversible or switchable adhesion characteristics, such as to transition between the adhesive state and the non-adhesive state. For example, the electroactive polymer 1400 can be configured to change a dimension or shape responsive to the one or more energy signals, which can increase or decrease the adhesive effect between the electroactive polymer 1400 and the skin surface to which the system 100 is applied (such as through a change in the amount of surface area in contact with the skin surface, or the like). The electroactive polymer 1400 can include, for example, an electroactive hydrogel, dielectric polymer, electrorestrictive polymer, electroviscoelastic polymer, ferroelectric polymer (e.g., PVDF), liquid crystal elastomer, ionic polymer (e.g., an ionomer such as Nafion), conductive polymer (e.g., polyaniline or polypyrrole films), ionomeric polymer-metallic composite (IPMC), conjugated polymer (e.g., peptide-conjugated PEDOT), single-network or double-network stimuli-responsive gel (e.g., methacrylates such as PMAA and POEGMA), carbon structures (including nanostructures), and the like. In an embodiment, the electroactive polymer 1400 is configured to reversibly transition between the adhesive state and the non-adhesive state responsive to the one or more energy signals from the circuitry 106. In an embodiment, the electroactive polymer 1400 is configured to reversibly transition between the nonadhesive state and the adhesive state responsive to the one or more energy signals from the circuitry 106.

The thermo-responsive adhesive 1402 can be actuatable by a change in temperature of the adhesive responsive to the one or more energy signals from the circuitry 106 to transition from the adhesive state to the non-adhesive state. For example, the thermo-responsive adhesive 1402 can be configured to at least partially ablate due to an increase in temperature responsive to interaction with the one or more energy signals from the circuitry 106, which can lead to loss or lessening of adhesion. The thermo-responsive adhesive 1402 can include, for example a thermo-responsive polymer, such as a polyacrylamide (e.g., Poly(N-isopropylacrylamide or poly(N,N-diethylacrylamide)), a shape memory polymer (e.g., epoxy-based), or a L-3,4-dihydroxylphenylalanine (DOPA)-modified polymer. In an embodiment, the thermo-responsive adhesive 1402 is configured to reversibly transition between the adhesive state and the non-adhesive state responsive to the one or more energy signals from the circuitry 106. In an embodiment, the thermo-responsive adhesive 1402 is configured to reversibly transition between the nonadhesive state and the adhesive state responsive to the one or more energy signals from the circuitry 106. For example, a thermoresponsive adhesive that becomes adhesive to tissue above a predetermined temperature (e.g., 32 degrees C.) and will lose its adhesive properties below that temperature responsive to the thermal energy signal. For example, a thermal-responsive adhesive includes a DOPA-modified PEG polymer and an oxidizing reagent stored in liposomes, which, when thermally triggered by the energy source, release the oxidizing agent thereby transforming the polymer to an adhesive hydrogel.

The magnetic-responsive adhesive 1404 can be actuatable by application of a magnetic field, or change in a magnetic field, applied to the adhesive responsive to the one or more energy signals from the circuitry 106, such as to transition from the adhesive state to the non-adhesive state. The magnetic-responsive adhesive 1404 can include, for example an array of micropillars formed with polydimethylsiloxane (PDMS) that has incorporated metallic micro- or nanoparticles such as neodymium (NdFeB) microparticles. In an embodiment, the magnetic-responsive adhesive 1404 is configured to reversibly transition between the adhesive state and the non-adhesive state responsive to the one or more energy signals from the circuitry 106. In an embodiment, the magnetic-responsive adhesive 1404 is configured to reversibly transition between the nonadhesive state and the adhesive state responsive to the one or more energy signals from the circuitry 106.

The light-responsive adhesive 1406 can be actuatable by application of a light source, or change in exposure to light, applied to the adhesive responsive to the one or more energy signals from the circuitry 106, such as to transition from the adhesive state to the non-adhesive state. The light-responsive adhesive 1406 can include, for example an azobenzene-modified glycoconjugate, azo-containing liquid crystalline network (LCN) micropillars, or combinations thereof. In an embodiment, the light-responsive adhesive 1406 is configured to reversibly transition between the adhesive state and the non-adhesive state responsive to the one or more energy signals from the circuitry 106. In an embodiment, the light-responsive adhesive 1406 is configured to reversibly transition between the nonadhesive state and the adhesive state responsive to the one or more energy signals from the circuitry 106. In embodiments, the light-responsive adhesive 1406 is sensitive to particular wavelengths of light (e.g., ultraviolet light, blue light, etc.). For example, application of the particular wavelengths of light can provide mitigation of the adhesive effect of the light-responsive adhesive 1406.

The reversible microstructure 1408 can be configured to transition between the adhesive state and the non-adhesive state responsive to the one or more energy signals from the circuitry 106. For example, the reversible microstructure 1408 can include microtip surfaces, such as elastomeric microtip surfaces, having geometric (e.g., pyramidal) structures protruding from posts arranged in arrays (e.g., square arrays). Such configurations can permit collapse of regions between the posts of the arrays between the protruding geometric structures, such as when subjected to an applied force. The reversible microstructure 1408 can provide differing levels of adhesion based on the underlying attractive forces between, for example, the reversible microstructure 1408 and a skin surface to which the system 100 is applied. For instance, the reversible microstructure 1408 can provide a generally high level of adhesion when the regions between the microtips are collapsed to maximize contact area between the reversible microstructure 1408 and the skin surface, which can facilitate van der Waals interactions. When the posts are permitted to retract to a resting state (e.g., neutral elastomeric positions), the adhesive effect is substantially reduced as compared to the collapsed state. In an embodiment, the reversible microstructure 1408 is configured to reversibly transition between the adhesive state and the non-adhesive state responsive to the one or more energy signals from the circuitry 106.

In embodiments, the reversible microstructure 1408 can comprise micropillar or microfibrillar structures or an array thereof, which can include biomimetic structural designs that confer adhesive properties (e.g., van der Waals forces, directional adhesion, and frictional adhesion) of natural *setae* (e.g., gecko *setae*), designs including anisotropic, asymmetrical materials or structure design (e.g., for anisotropic directional and frictional adhesion), and end shape design. For example, end shapes can include one or more of a plate shape (e.g., T or L shapes), semi-sphere shape, concave shape, mushroom shape, fibrillar shapes, or lamellae (e.g., in a hierarchical structure). Micropillar or microfibrillar structures can be formed from energy-responsive materials, energy non-responsive materials, or mixtures thereof including, but not limited to, polymide, PVS, PDMS, poly(methyl methacrylate) (PMMA), polyurethane, polystyrene (PS), silicon rubber, polypropylene, polyethylene, poly (methylvinylsiloxane) (PMVS), IPMC, and other polymers listed in here, as well as carbon structures (including nanostructures). Different portions (e.g., the end shape) of a micropillar or microfibrillar structure can be formed from a material that is different than that forming another portion (e.g., the pillar or fiber) of the structure. At least a portion of a micropillar or microfibrillar structure can be coated, for example with an energy-responsive polymer or with a substance that confers biocompatibility.

Micropillar or microfibrillar structures can be configured to transition between the adhesive state and the non-adhesive state responsive to the one or more energy signals from the circuitry 106. In an embodiment, the reversible microstructure 1408 is configured to reversibly transition between the adhesive state and the non-adhesive state responsive to the one or more energy signals from the circuitry 106. For example, adhesive properties of a reversible microstructure that includes micropillar or microfibrillar structures can be altered by altering the orientation of the micropillar or microfibrillar structures (thereby altering the frictional or directional adhesive properties), responsive to the one or more energy signals from the circuitry 106. In an embodiment, the magnetic-responsive adhesive 1404 includes micropillar structures with a T-shaped ending and formed from a magnetic-responsive material (e.g., PDMA with NdFeB microparticles) controllably tilt in the presence of a magnetic field according to the strength and direction of the field, so that adhesion of the micropillar structures can be controllably disrupted responsive to the one or more electromagnetic signals from the circuitry 106.

In an embodiment, the adhesive 1300 includes an actuator responsive to the one or more energy signals from the circuitry 106. For example, an array of micropillars formed from PMVS is attached to an actuator of IPMC, which, responsive to the one or more energy signals from the circuitry 106 (e.g., at 1.0, 1.5, or 2.0 V depending on desired adhesion), bends driving the micropillars to actively adhere to or release the surface.

Figure 15:
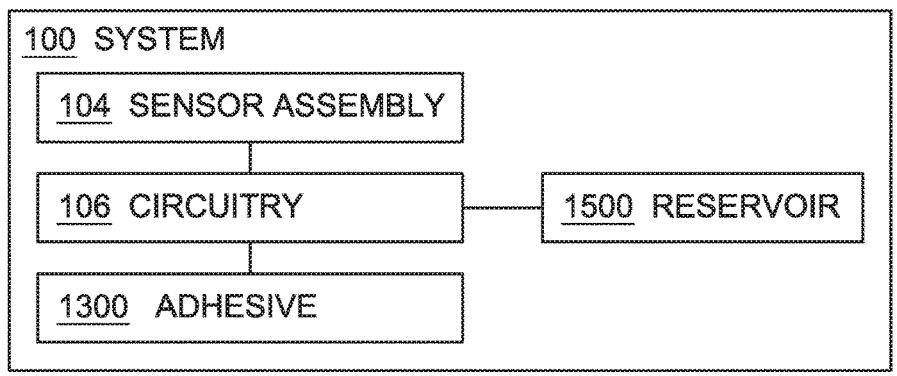
FIG. 15 is a schematic of an embodiment of a system such as shown in FIGS. 1 and 10.

In an embodiment, shown in FIG. 15, the system 100 includes a reservoir 1500 configured to release an adherence mitigator responsive to the one or more energy signals from the circuitry 106. The adherence mitigator is configured to interact with the adhesive 1300 to transition the adhesive 1300 from the adhesive state to the non-adhesive state. For example, the adherence mitigator can include a substance having a pH (e.g., an acid) that alters the ionic properties of the adhesive (e.g., a single or double network poly(methacrylic acid) hydrogel that bonds at pH 6 but loses adhesion when exposed to acidic pH). For example, the adherence mitigator can include a solvent that degrades a polymer adhesive. The reservoir 1500 can be formed from a portion of the material of the deformable substrate 102, can be formed from a structure positioned on a surface of the deformable substrate 102, or a combination thereof. In an embodiment, the reservoir 1500 includes a plurality of reservoirs, configured to release the reservoir contents temporally, sequentially, in parallel, or in combinations thereof. In an embodiment, the reservoir 1500 includes an energy-responsive hydrogel configured to release the reservoir contents upon stimulation (e.g., in response to the one or more energy signals, in response to an electric signal, in response to a thermal signal, in response to an electromagnetic signal, etc.) In scenarios where the individual subject cannot be identified, or where the individual subject is identified but not authorized to operate an external device, the circuitry 106 can generate one or more energy signals to activate the reservoir 1500 to cause release of the adherence mitigator, thereby permitting interaction between the adherence mitigator and the adhesive 1300. In an embodiment, the adherence mitigator includes one or more of a fluid material or a powdered material. In an embodiment, the adhesive 1300 is configured to transition from the non-adhesive state to the adhesive state upon removal of the adherence mitigator. For example, the adherent material can be washed or otherwise removed from contact with the adhesive 1300 to permit the adhesive 1300 to attain the adhesive state. In an embodiment, the adherence mitigator is configured to degrade at least a portion of at least one of the adhesive 1300, the deformable substrate 102, the sensor assembly 104, or the circuitry 106. Such degradation can influence the functionality of one or more of the adhesive 1300, the deformable substrate 102, the sensor assembly 104, or the circuitry 106, such as by causing at least a portion of the adhesive 1300, the deformable substrate 102, the sensor assembly 104, or the circuitry 106 to become inoperative. In an embodiment, the one or more energy signals generated by the circuitry 106 are configured to degrade at least a portion of at least one of the adhesive 1300, the deformable substrate 102, the sensor assembly 104, or the circuitry 106. Such degradation can influence the functionality of one or more of the adhesive 1300, the deformable substrate 102, the sensor assembly 104, or the circuitry 106, such as by causing at least a portion of the adhesive 1300, the deformable substrate 102, the sensor assembly 104, or the circuitry 106 to become inoperative. For example, in scenarios where the individual subject cannot be identified, or where the individual subject is identified but not authorized to operate an external device, the circuitry 106 can generate one or more energy signals to cause the inoperability of one or more functions of one or more of the adhesive 1300, the deformable substrate 102, the sensor assembly 104, or the circuitry 106, due to direct interaction with the energy signals or due to interaction with the adherence mitigator released from the reservoir 1500. In an embodiment (not shown) the system 100 includes a reservoir configured to release an adherence promoter responsive to the one or more energy signals from the circuitry 106. For example, the adherence promotor can include a pH enhancer, a wetting agent, a drying agent, or the like.

FIG. 16 illustrates a method 1600 for identifying an individual using conformable electronics positioned on the individual. Method 1600 shows generating one or more identity sense signals in block 1602, where the sense signals correspond to an individual subject and are generated by an identification device having a deformable substrate and at least one sensor coupled to the deformable substrate. For example, the sensor assembly 104 (e.g., one or more identity sensors 200) can generate one or more identity sense signals associated with an individual subject on which the system 100 is positioned. Method 1600 also includes comparing the one or more identity sense signals to reference data indicative of one or more physical characteristics associated with an identity of at least one individual in block 1604. For example, the circuitry 106 can compare (e.g., via comparison module 400, via comparison module 1000, etc.) the identity sense signals to reference data stored in memory (e.g., memory 402), where the reference data includes physical characteristics linked or associated with an identity of a known individual. Where the identity sense signals meet or exceed a threshold correspondence when compared to the reference data, the identity linked or associated with the physical characteristics stored in memory can be correlated to the individual subject on which the system 100 is positioned (i.e., the individual subject can be presumed to have the known identity based on a successful correspondence). Where the identity sense signals do not meet a threshold correspondence when compared to the reference data, the identity linked or associated with the physical characteristics stored in memory cannot be correlated to the individual subject on which the system 100 is positioned (i.e., the individual subject is not presumed to have the known identity based on the unsuccessful correspondence). Method 1600 also includes reporting one or more communication signals related to the identity sense signals or the comparison of the identity sense signals to the reference data in block 1606. For example, the reporter 108 can generate the one or more communication signals responsive to instruction by the circuitry 106, where such communication signals can relate to the identity sense signals or to the comparison by the circuitry 106 of the identity sense signals with the reference data. For instance, the communication signals can indicate a successful correspondence between the identity signals and the reference data (e.g., provide the established identity of the individual subject on which the system 100 is positioned), can indicate an unsuccessful correspondence between the identity sense signals and the reference data (e.g., provide that the identity of the individual subject on which the system 100 is positioned cannot be established with a certain threshold correspondence), or the like.

FIG. 17 illustrates a method 1700 for identifying and authorizing an individual using conformable electronics positioned on the individual. Method 1700 shows generating one or more identity sense signals in block 1702, where the sense signals correspond to an individual subject and are generated by an identification device having a deformable substrate and at least one sensor coupled to the deformable substrate. For example, the sensor assembly 104 (e.g., one or more identity sensors 200) can generate one or more identity sense signals associated with an individual subject on which the system 100 is positioned. Method 1700 also includes comparing the one or more identity sense signals to reference data indicative of one or more physical characteristics associated with an identity of at least one individual in block 1704. For example, the circuitry 106 can compare (e.g., via comparison module 400, via identity comparison module 1000) the identity sense signals to reference data stored in memory (e.g., memory 402), where the reference data includes physical characteristics linked or associated with an identity of a known individual. Where the identity sense signals meet or exceed a threshold correspondence when compared to the reference data, the identity linked or associated with the physical characteristics stored in memory can be correlated to the individual subject on which the system 100 is positioned (i.e., the individual subject can be presumed to have the known identity based on a successful correspondence). Where the identity sense signals do not meet a threshold correspondence when compared to the reference data, the identity linked or associated with the physical characteristics stored in memory cannot be correlated to the individual subject on which the system 100 is positioned (i.e., the individual subject is not presumed to have the known identity based on the unsuccessful correspondence). Method 1700 also includes comparing the one or more identity sense signals or a determined identity with one or more authorization parameters in block 1706. For example, the circuitry 106 can compare (e.g., via authorization comparison module 1002) the one or more identity sense signals with one or more authorization parameters to determine whether the identity sense signals correspond to an individual that is authorized to operate an associated external device (such as when the reference data includes a list of physical characteristics associated with individuals authorized to operate at least a portion of the functionalities of the external device 800). The circuitry 106 can compare (e.g., via authorization comparison module 1002) an identity of the individual subject (e.g., when the identity sense signals sufficiently correspond to the physical characteristics provided in the reference data in order to identify the individual subject) to a list of individuals authorized to operate the external device to determine whether the identified individual subject can operate at least a portion of the functionalities of the external device. Method 1700 also includes reporting to an associated external device one or more communication signals related to the comparison with authorization parameters in block 1708. For example, the reporter 108 can generate the one or more communication signals responsive to instruction by the circuitry 106 to report to the external device 800, where such communication signals can relate to whether the individual subject is authorized to operate the external device, such as by being unable to identify the individual (e.g., no authorization), by identifying the individual but the identified individual is not on the authorized list (e.g., no authorization), by successfully corresponding the identity sense signals with physical characteristics of authorized individuals (e.g., authorization), by identifying the individual and having the identified individual being on the authorized list (e.g., authorization), or the like.

FIG. 18 illustrates a method 1800 for adjusting an adhesive state of an adhesive responsive to identification of an individual using conformable electronics. Method 1800 shows generating one or more identity sense signals in block 1802, where the sense signals correspond to an individual subject and are generated by an identification device having a deformable substrate and at least one identity sensor coupled to the deformable substrate. For example, the sensor assembly 104 (e.g., one or more identity sensors 200) can generate one or more identity sense signals associated with an individual subject on which the system 100 is positioned. Method 1800 also includes comparing the one or more identity sense signals to reference data indicative of one or more physical characteristics associated with an identity of at least one individual in block 1804. For example, the circuitry 106 can compare (e.g., via comparison module 400, via comparison module 1000, etc.) the identity sense signals to reference data stored in memory (e.g., memory 402), where the reference data includes physical characteristics linked or associated with an identity of a known individual. Where the identity sense signals meet or exceed a threshold correspondence when compared to the reference data, the identity linked or associated with the physical characteristics stored in memory can be correlated to the individual subject on which the system 100 is positioned (i.e., the individual subject can be presumed to have the known identity based on a successful correspondence). Where the identity sense signals do not meet a threshold correspondence when compared to the reference data, the identity linked or associated with the physical characteristics stored in memory cannot be correlated to the individual subject on which the system 100 is positioned (i.e., the individual subject is not presumed to have the known identity based on the unsuccessful correspondence). Method 1800 also includes transitioning an adhesive from an adhesive state to a non-adhesive state upon determination that the identity sense signals do not provide a threshold correspondence to the physical characteristics in block 1806. For example, the circuitry 106 can generate one or more energy signals to interact with the adhesive 1300 to transition the adhesive 1300 from an adhesive state to a non-adhesive state when the identity of the individual subject on which the system 100 is positioned cannot be determined within a particular threshold correspondence. In such circumstances, the system 100 may no longer be positioned on the individual subject due to an inability of the adhesive 1300 to maintain a suitable connection to a skin surface of the individual subject when in the non-adhesive state.

FIG. 19 illustrates a method 1900 for adjusting an adhesive state of an adhesive responsive to identification of an individual using conformable electronics. Method 1900 shows generating one or more identity sense signals in block 1902, where the sense signals correspond to an individual subject and are generated by an identification device having a deformable substrate and at least one identity sensor coupled to the deformable substrate. For example, the sensor assembly 104 (e.g., one or more identity sensors 200) can generate one or more identity sense signals associated with an individual subject on which the system 100 is positioned. Method 1900 also includes comparing the one or more identity sense signals to reference data indicative of one or more physical characteristics associated with an identity of at least one individual in block 1904. For example, the circuitry 106 can compare (e.g., via comparison module 400, via comparison module 1000, etc.) the identity sense signals to reference data stored in memory (e.g., memory 402), where the reference data includes physical characteristics linked or associated with an identity of a known individual. Where the identity sense signals meet or exceed a threshold correspondence when compared to the reference data, the identity linked or associated with the physical characteristics stored in memory can be correlated to the individual subject on which the system 100 is positioned (i.e., the individual subject can be presumed to have the known identity based on a successful correspondence). Where the identity sense signals do not meet a threshold correspondence when compared to the reference data, the identity linked or associated with the physical characteristics stored in memory cannot be correlated to the individual subject on which the system 100 is positioned (i.e., the individual subject is not presumed to have the known identity based on the unsuccessful correspondence). Method 1900 also includes transitioning an adhesive from a non-adhesive state to an adhesive state upon determination that the identity sense signals provide a threshold correspondence to the physical characteristics in block 1906. For example, the circuitry 106 can generate one or more energy signals to interact with the adhesive 1300 to transition the adhesive 1300 from a non-adhesive state to an adhesive state when the identity of the individual subject on which the system 100 is positioned can be determined within a particular threshold correspondence. For example, the system 100 may be manually positioned or held against the body portion of an individual subject to permit the sensor assembly 104 to generate the identity sense signals, which when the identity can be determined, the adhesive 1300 can transition from the non-adhesive state to an adhesive state (e.g., via interaction with the energy signals from the circuitry 106) to maintain a suitable connection to a skin surface of the individual subject, such as to fix the system 100 in place on an identified individual.

In an embodiment, the system 100 is configured as an authorized key or pass. For example, an individual subject can utilize a system described herein to gain access to a building (e.g., clinic, hospital, ER, care facility), room, or kiosk, and to interface with systems therein. The individual subject can utilize a system described herein to gain access to a local gym and interface with its system. The individual subject's identity can be recognized, and the individual subject can be directed to particular exercise equipment or classes specific for that individual subject. The individual subject can also receive feedback once interacting or engaging with the exercise equipment or, for example, doing exercises in front of a mirror or mat with sensors. Thus, the individual subject can receive physical therapy, occupational therapy, or customized exercises specifically tailored to him or her by utilizing a system described herein. Further, the system can make product or service recommendations to the individual subject based on the subject's profile. For example, nutrition products or athletic gear or exercise services can be tailored to the individual subject as selected advertising or promotional offers (coupons, etc.). For example, an individual subject can utilize a system as a transportation pass, such as a bus pass, boarding ticket, or venue ticket. After using the pass, the individual subject individual subject's identity can be recognized, and the individual subject can be directed to particular seat. Further, the system can make product or service recommendations to the individual subject based on the subject's profile, for example suggesting a pair of headphones useful for the venue or a particular beverage tailored to the individual subject as selected advertising.

As an example, an individual subject can utilize a system described herein to gain access to one or more piece of equipment such as that described herein. In this regard, the system can identify the individual and activate the transmission by the system so as to act as a key for any of several pieces of equipment configured to receive the predetermined transmission.

As an example, an individual subject can utilize a system described herein to interface with other information or sensor systems for collecting and transmitting data. For example, health sensors worn by an individual subject can interface with the system, which identifies the individual subject and controls data transmission. Identity is authenticated and transmission is allowed, e.g., to a health care record or daily activity record specific to the individual subject. The transmission includes information associating data with the individual subject. The system can further provide recommendations for products or services based on the data (e.g., a recommendation to see a health care provider or have a prescription filled) and can interface with a third party, such as a health care provider's office or pharmacy, to schedule an appointment or place an order, using the identity and authentication.

Systems, devices, and methods are described for identification and authorization of individuals including, but not limited to, healthcare providers (e.g., physicians, nurses, care providers, medical assistants, physicians assistants, lab technicians, etc.) and individual subjects including patients, research subjects, other healthcare providers, and other persons in a medical, research, rehabilitation, or extended care facility, using conformable electronics for aspects of the identification and authorization processes. Authorizations can include, but are not limited to, authorizations to perform actions with respect to other individuals, authorizations to access information, authorizations to operate external devices, and so forth.

In an embodiment, a system or device as described herein can be applied to, maintained against, or can otherwise be in contact with, a skin surface of a body portion of a healthcare provider to evaluate one or more physical characteristics of the healthcare provider, including but not limited to, skin topography features (e.g., pattern of skin surface, follicle pattern, pore pattern, pigmentation, etc.), vascular properties or layouts, electric current pattern (e.g., photovoltaic current pattern), or skin resistivity measurement. The physical characteristics can be compared against reference data that include physical characteristics of known identities to determine whether the measured physical characteristics correspond to the reference physical characteristics, whereby the particular identity of the healthcare provider can be determined or inferred. The identity of the healthcare provider may be determined or inferred prior to or in conjunction with an authorization of the healthcare provider to perform a health service action with respect to an individual subject. In an embodiment, the identity of the healthcare provider may be determined or inferred prior to or in conjunction with an authorization of the healthcare provider to perform a health service action including, but not limited to, operating an external device, performing a scheduled procedure, or accessing information associated with the individual subject.

In an embodiment, a system or device as described herein can be applied (e.g., adhered or otherwise attached) to a skin surface of a body portion of a first individual (e.g., a healthcare provider) and configured to evaluate one or more physical characteristics of a second individual (e.g., an individual subject), including but not limited to, skin topography features (e.g., pattern of skin surface, follicle pattern, pore pattern, pigmentation, etc.), vascular properties or layouts, electric current pattern (e.g., photovoltaic current pattern), or skin resistivity measurement. The physical characteristics can be compared against reference data that include physical characteristics of known identities to determine whether the measured physical characteristics correspond to the reference physical characteristics, whereby the particular identity of the second individual can be determined or inferred. In an embodiment, a system or device as described herein can be applied to a skin surface of a first individual and configured to at least partially conform to a skin surface of a body portion of a second individual to evaluate one or more physical characteristics of the second individual. In an embodiment, a system or device as described herein can be applied to a skin surface of a first individual and configured to scan a skin surface of a body portion of a second individual at a distance to evaluate one or more physical characteristics of the second individual.

In an embodiment, a system or device as described herein can be applied to, maintained against, or can otherwise be in contact with, a skin surface of a body portion of an individual subject (e.g., a patient or client) to evaluate one or more physical characteristics of the individual subject, including but not limited to, skin topography features (e.g., pattern of skin surface, follicle pattern, pore pattern, pigmentation, etc.), vascular properties or layouts, electric current pattern (e.g., photovoltaic current pattern), or skin resistivity measurement. The physical characteristics can be compared against reference data that include physical characteristics of known identities to determine whether the measured physical characteristics correspond to the reference physical characteristics, whereby the particular identity of the individual subject can be determined or inferred. The identity of the individual subject may be determined or inferred prior to or in conjunction with an authorization of the individual subject to perform an action associated with a scheduled parameter. In an embodiment, the identity of the individual subject may be determined or inferred prior to or in conjunction with an authorization of the individual subject to perform an action associated with a scheduled parameter corresponding to at least one of a treatment schedule, a recovery schedule, a rehabilitation schedule, a pre-operative schedule, a post-operative schedule, a discharge schedule, or the like. For example, a scheduled parameter can include, but is not limited to, a list of identities of one or more individuals scheduled to undergo a procedure, a list of identities of one or more individuals scheduled to receive a treatment, a list of identities of one or more individuals scheduled to operate an external device (e.g., a therapeutic device), a list of identities of one or more individuals with pre-operative permissions or restrictions, a list of identities of one or more individuals with post-operative permissions or restrictions, a list of identities of one or more individuals with pre-treatment permissions or restrictions, a list of identities of one or more individuals with post-treatment permissions or restrictions, or a combination thereof.

In an embodiment, an identification of an individual can lead to subsequent authorization, such as authorization reported to or processed by an external device or an information system. Such authorization can permit operation of the external device, access to information stored by the information system, or operation of an associated device or system by the identified and authorized individual, for the identified and authorized individual, or can permit an external device, information system, or an associated device or system to be aware of the identity of the individual.

In an embodiment, a system or device as described herein can employ one or more identity sensors configured to monitor or sense at least one physical characteristic of the individual. The identity sensor can include, but is not limited to, an optical sensor, an electromagnetic sensor, an impedance sensor, a capacitive sensor, an electrophysiological sensor, a plethysmographic sensor, a resistive sensor, a biosensor, or a chemical sensor. The identity sensors are coupled to circuitry configured to compare the output of the identity sensors to reference data to determine whether the output of the identity sensors corresponds to an identity of a known individual. The systems can also include one or more of physiological sensors, proximity sensors, contact sensors, pressure sensors, or temperature sensors to facilitate operation of the system, to provide contextual data in combination with the output from the identity sensors, to toggle activation/deactivation of one or more components of the system, or the like.

In an embodiment, a system or device as described herein can employ a reporter configured to generate one or more communication signals responsive to instruction by the circuitry. For example, the reporter can convey information via the one or more communication signals directed to the output of the sensors, a comparison of the output of the sensors with reference data (e.g., reference identity data or reference physical characteristics), identity information of the individual on which the system or device is positioned, identity information of a second individual having a skin surface of a body portion in contact with or scanned by the system or device, authorization information (e.g., whether or not an identified individual is authorized, such as authorized to perform an action, receive a treatment, operate a particular device, machine, electronic device, etc.), or the like.

Figure 20:
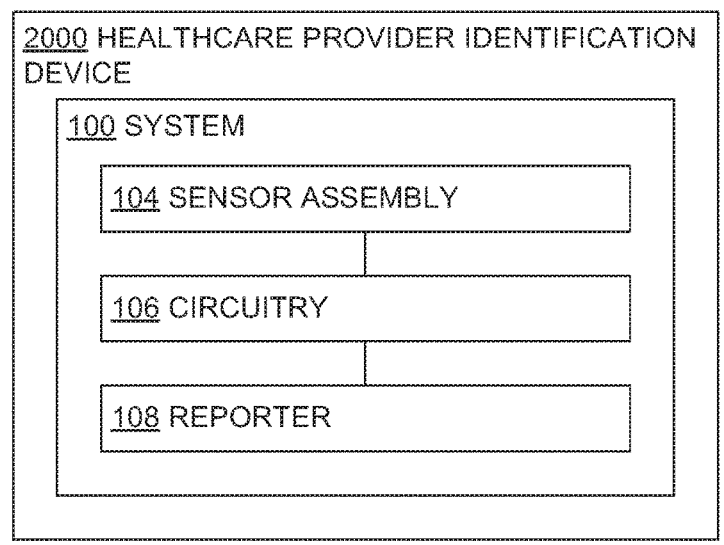
FIG. 20 is a schematic of a healthcare provider identification device including a system for identification of an individual using conformable electronics, such as the system shown in FIGS. 1 through 15.

In an embodiment, shown in FIG. 20, a healthcare provider identification device 2000 is configured to evaluate one or more physical characteristics of a healthcare provider on which the healthcare provider identification device 2000 is positioned to facilitate identification of the healthcare provider. The healthcare provider identification device 2000 includes a system (or device), such as the system 100 described herein to facilitate the identification of the healthcare provider. As described herein and shown in FIG. 1, in an embodiment, the system 100 includes deformable substrate 102, sensor assembly 104, circuitry 106, and reporter 108. In an embodiment, the deformable substrate 102 is configured to conform to a contour of a body portion of a healthcare provider (e.g., the curvature of a limb). For example, as described herein, the deformable substrate 102 can comprise a deformable (e.g., conformable, flexible, stretchable, etc.) material configured to interface with, and conform to, the body portion. The body portion is shown in FIG. 1 as a hand, however the system 100 can be positioned on the skin surface of any body portion, including but not limited to, an arm, an elbow, a wrist, a hand, a finger, a leg, a knee, an ankle, a foot, a toe, a facial region, a neck region, a torso region, or the like. The deformable substrate 102 can be positioned in proximity with the skin surface according to various mechanisms including, but not limited to, affixed to the skin via an adhesive material, held in place by an external pressure, such as pressure provided by a material wrapped around or about a body portion (e.g., a fabric, a garment, a glove, a bandage, etc.), affixed in a textile, fabric, garment, accessory (e.g., a glove, a sock, a finger cot, etc.), or so forth.

As described herein, the sensor assembly 104 is coupled to the deformable substrate 102 and is positioned to generate one or more sense signals associated with a physical characteristic of the individual (e.g., healthcare provider) on whom the system 100 is positioned. For example, as shown in FIG. 2, the sensor assembly 104 includes one or more identity sensors 200 configured to generate one or more identity sense signals associated with at least one physical characteristic of the healthcare provider. The identity sensor 200 can sense the physical characteristic to provide a basis for identification of the healthcare provider, or to provide an indication that the healthcare provider cannot be readily identified based on the observed physical characteristics. As described herein, the identity sensor 200 can include, but is not limited to, one or more of an optical sensor 202, an electromagnetic sensor 204, an impedance sensor 206, a capacitive sensor 208, an electrophysiological sensor 210, a plethysmographic sensor 212, a resistive sensor 214, a biosensor 216, or a chemical sensor 218. The identity sensor 200 can generate the one or more identity sense signals based on measurement or sensing of one more physical characteristics of the healthcare provider, where the one or physical characteristics can include, but are not limited to, skin topography features (e.g., pattern of skin surface, follicle pattern, pore pattern, pigmentation, etc.), vascular properties or layouts (e.g., arterial patterns, properties, or layouts; vein patterns, properties, or layouts; etc.), electric current pattern (e.g., photovoltaic current pattern), or skin resistivity measurement. For example, as shown in FIG. 3, the system 100 can be positioned on a skin surface of a body portion (shown as a top surface of a hand in FIG. 3), where the system 100 can detect via the identity sensor 200 one or more of a follicle pattern 300, a pore pattern 302, a skin pigmentation or distinctive skin mark 304, or a vascular pattern or layout 306. The identity sensor 200 can then generate one or more identity sense signals based on the structure of the particular sensor(s) of the sensor assembly 104 (e.g., optical sensor 202, electromagnetic sensor 204, impedance sensor 206, etc.), where such signals will correspond to the measured or sensed physical characteristics to facilitate in analysis of whether the identity of the healthcare provider can be determined.

Figure 21:
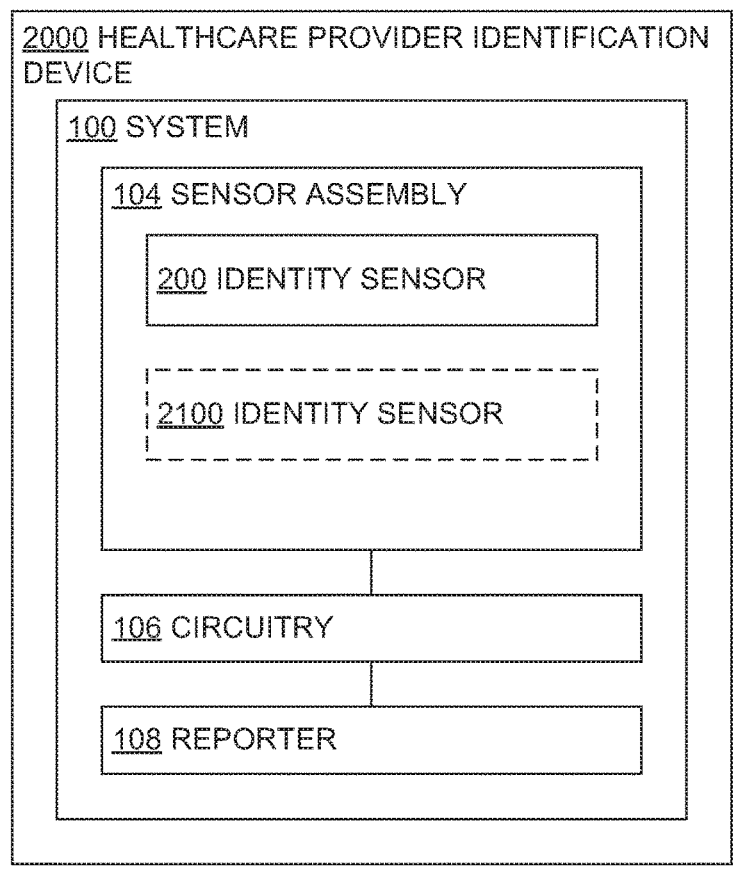
FIG. 21 is a schematic of an embodiment of a healthcare provider identification device such as shown in FIG. 20.

In an embodiment, shown in FIG. 21, the one or more identity sensors 200, or another one or more identity sensors 2100 of the sensor assembly 104 having similar or same structure and functionality as the one or more identity sensors 200, are configured to generate one or more identity sense signals associated with at least one physical characteristic of a second individual other than the individual on whom the deformable substrate 102 is positioned. For example, the sensor assembly 104 can be configured to generate one or more identity sense signals associated with an individual subject (e.g., a patient, another healthcare provider, or another individual) being evaluated or cared for by a healthcare provider on whom the system 100 is placed.

Figure 22A:
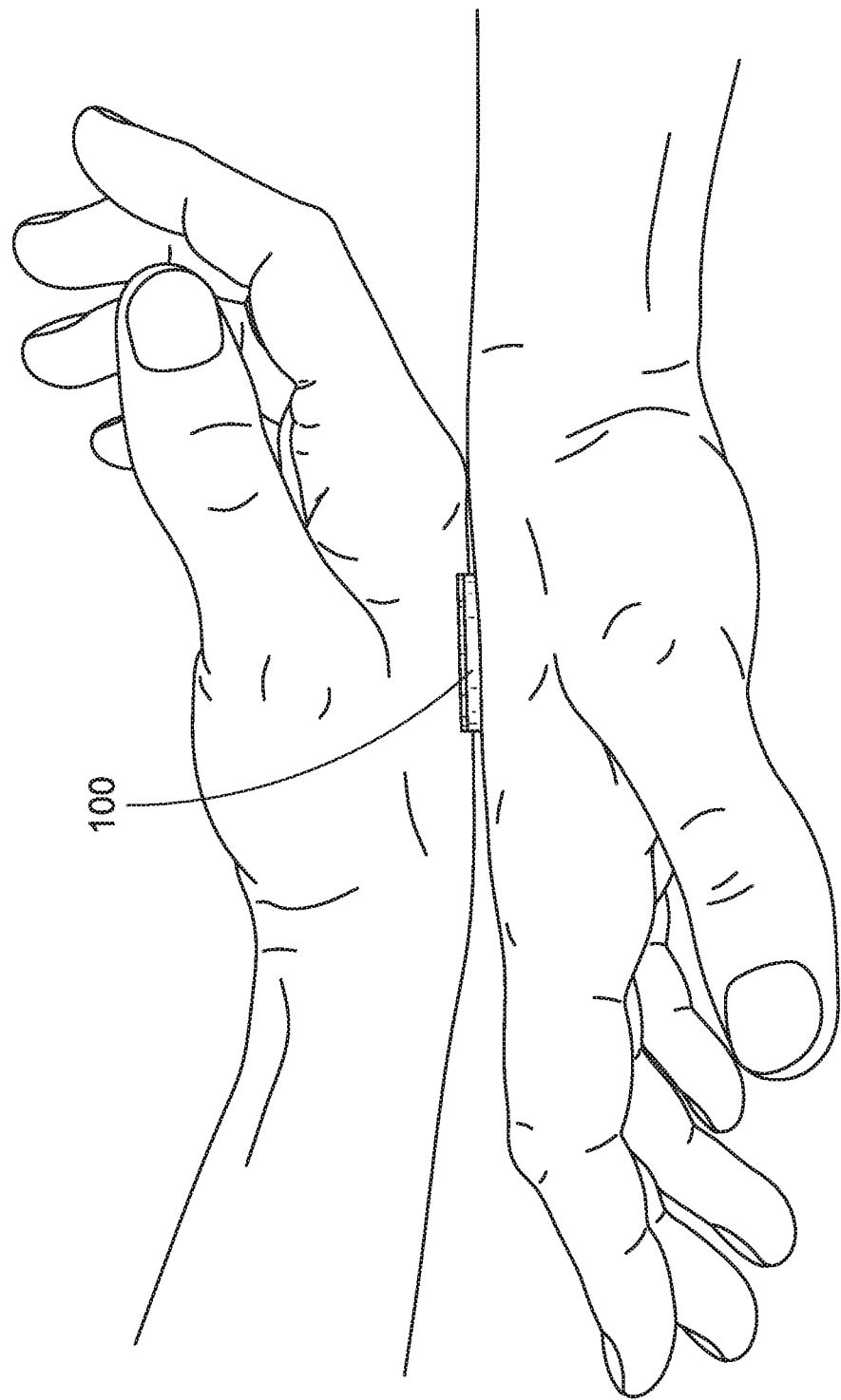
FIG. 22A is a schematic of an embodiment of a healthcare provider identification device such as shown in FIG. 20.

The identity sensor 200 (or identity sensor 2100) can sense the physical characteristic to provide a basis for identification of the second individual or to provide an indication that the other individual cannot be readily identified based on the observed physical characteristics. The identity sensor 200 (or identity sensor 2100) can generate the one or more identity sense signals based on measurement or sensing of one more physical characteristics of the individual subject, where the one or physical characteristics can include, but are not limited to, skin topography features (e.g., pattern of skin surface, follicle pattern, pore pattern, pigmentation, etc.), vascular properties or layouts (e.g., arterial patterns, properties, or layouts; vein patterns, properties, or layouts; etc.), electric current pattern (e.g., photovoltaic current pattern), or skin resistivity measurement. For example, as shown in FIGS. 22A and 22B, the system 100 can be positioned on a skin surface of a body portion of a first individual (e.g., the healthcare provider) and can sense one or more physical characteristics of a second individual (e.g., the individual subject), where the system 100 can detect via the identity sensor 200 (or identity sensor 2100) one or more of a follicle pattern, a pore pattern, a skin pigmentation or distinctive skin mark, or a vascular pattern or layout. The identity sensor 200 (or identity sensor 2100) can then generate one or more identity sense signals based on the structure of the particular sensor(s) of the sensor assembly 104 (e.g., optical sensor 202, electromagnetic sensor 204, impedance sensor 206, etc.), where such signals will correspond to the measured or sensed physical characteristics to facilitate in analysis of whether the identity of the second individual can be determined. In an embodiment, shown in FIG. 22A, the sensor assembly 104 can be configured to sense the one or more physical characteristics when the system is in contact with a skin surface of a body portion of the second individual. In an embodiment, shown in FIG. 22B, the sensor assembly 104 can be configured to sense the one or more physical characteristics at a distance from the skin surface of the body portion of the second individual. For example, the sensor assembly 104 can sense the one or more physical characteristics associated with the second individual utilizing noncontact or remote sensors. In an embodiment, electrocardiographic or electroencephalographic patterns associated with the second individual (e.g., a patient) may be obtained by measuring electrical potentials and bioelectric signals using a remote or noncontact high input impedance electrometer or capacitive sensor. In an embodiment, heartbeat intervals and electrocardiographic information may be obtained using an electromagnetic signal sent at and reflected from the second individual (e.g., radiofrequency or microwave signals). In an embodiment, skin characteristic (e.g., one or more of a follicle pattern, a pore pattern, a skin pigmentation or distinctive skin mark) information may be obtained using an optical sensor or imager (e.g., scanner) with or without an electromagnetic signal sent at and reflected from the second individual (e.g., light or radiofrequency signals). In an embodiment, the sensor assembly 104 can include a first identity sensor 200 configured to be oriented towards a skin surface of a body portion of the individual on whom the deformable substrate 102 is positioned and a second identity sensor 2100 configured to be oriented away from the skin surface of the body portion of the individual on whom the deformable substrate 102 is positioned, where the first identity sensor 200 is configured to generate one or more identity sense signals associated with the individual on whom the deformable substrate 102 is positioned, and the second identity sensor 2100 is configured to generate one or more identity sense signals associated with a second individual in proximity of the individual on whom the deformable substrate 102 is positioned.

As described herein, the sensor assembly 104 can be structured relative to the deformable substrate 102 such that at least a portion of the sensor assembly 104 is embedded within the deformable substrate 102, affixed to the deformable substrate 102, residing on the deformable substrate 102, printed directly onto the deformable substrate 102, or a combination thereof. For example, at least a portion of an identity sensor 200 (or identity sensor 2100) can be embedded within the deformable substrate 102, can be affixed to the deformable substrate 102, can reside on the deformable substrate 102, can be directly printed on the deformable substrate 102, or a combination thereof. In an embodiment, the deformable substrate 102 can include one or more of a stretchable/flexible fabric, an elastomeric polymer, a hydrocolloid film, a membrane (e.g., a nanomembrane, such as a silicon nanomembrane), a gas-permeable elastomeric sheet, or other conformable material. In an embodiment, at least one of the sensor assembly 104, the circuitry 106, or the reporter 108 resides on the deformable substrate 102, such as residing on at least a portion of one or more of a stretchable/flexible fabric, an elastomeric polymer, a hydrocolloid film, a membrane (e.g., a nanomembrane, such as a silicon nanomembrane), a gas-permeable elastomeric sheet, or other conformable material. For example, at least a portion of at least one of the sensor assembly 104, the circuitry 106, or the reporter 108 can be printed directly onto at least a portion of the deformable substrate 102. In an embodiment, at least one of the sensor assembly 104, the circuitry 106, or the reporter 108 is embedded within the deformable substrate 102, such as embedded within at least a portion of one or more of a stretchable/flexible fabric, an elastomeric polymer, a hydrocolloid film, a membrane (e.g., a nanomembrane, such as a silicon nanomembrane), a gas-permeable elastomeric sheet, or other conformable material.

In an embodiment, the circuitry 106 is configured to receive one or more identity sense signals (e.g., from the sensor assembly 104) associated with one or more physical characteristics of the healthcare provider on which system 100 is positioned, and can provide analysis of the one or more identity sense signals. For example, in an embodiment, the circuitry 106 is operably coupled to the sensor assembly 104 such that the circuitry 106 is configured to receive the one or more identity sense signals from the one or more identity sensors 200 of the sensor assembly 104. In an embodiment, shown in FIG. 4, the circuitry 106 includes a comparison module 400 configured to compare the one or more identity sense signals generated by the sensor assembly 104 to reference data indicative of one or more physical characteristics associated with an identity of at least one individual to determine whether the one or more identity signals correspond to the identity of the at least one individual. In an embodiment, the reference data is stored in a computer memory device 402 which can include, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information maintained by the comparison module 400 and which can be accessed by the circuitry 106 or other associated accessing device.

In an embodiment, the circuitry 106 is configured to receive one or more identity sense signals (e.g., from the sensor assembly 104) associated with one or more physical characteristics of an individual subject being evaluated or cared for by the healthcare provider on which system 100 is positioned, and can provide analysis of the one or more identity sense signals. For example, in an embodiment, the circuitry 106 is operably coupled to the sensor assembly 104 such that the circuitry 106 is configured to receive the one or more identity sense signals associated with a second individual from the one or more identity sensors 200 (or identity sensor 2100) of the sensor assembly 104. In an embodiment, the comparison module 400 is configured to compare the one or more identity sense signals generated by the sensor assembly 104 to reference data indicative of one or more physical characteristics associated with an identity of at least one individual to determine whether the one or more identity signals correspond to the identity of the at least one individual. In an embodiment, the reference data is stored in a computer memory device 402 which can include, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information maintained by the comparison module 400 and which can be accessed by the circuitry 106 or other associated accessing device.

As described herein, the circuitry 106 includes components to process the one or more sense signals from the sensor assembly 104 and to provide instruction to the reporter 108 to generate one or more communication signals associated with the one or more identity sense signals, a comparison of the one or more identity sense signals with the one or more physical characteristics from reference data indicative with an identity of a particular individual, determinations made by the circuitry 106, or other information. For example, the circuitry 106 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In an embodiment, the circuitry 106 includes one or more ASICs having a plurality of predefined logic components. In an embodiment, the circuitry 106 includes one or more FPGAs having a plurality of programmable logic commands. The computer memory device can be integrated with the system 100, can be associated with an external device and accessible by the system 100 through wireless or wired communication protocols, or a combination thereof. For example, the reference data can be stored by the computer memory 702 coupled to the deformable substrate 102 of the system 100, can be accessible by the circuitry 106 via wireless means, or can be available to the circuitry 106 through another method, such as through a remote network, a cloud network, and so forth. In an embodiment, the circuitry 106 includes a receiver 404 or transceiver 406 (e.g., antenna, etc.) to receive the reference data information or other information (e.g., correspondence threshold information, programming information) to facilitate operation or control of the system 100 through wireless or wired communication protocols. For example, the receiver 404 can receive one or more communication signals from an external device associated with but not limited to, control programming, authorization parameters, reference data, or a query (e.g., a query to transmit information from the system 100 to the external device, a query to begin sensing of identity sense signals via the sensor assembly 104, etc.). In embodiments, the circuitry 106 can also include a transmitter 408 or transceiver (e.g., antenna, etc.) to send information amongst components of the system 100 or to components external the system, such as to communicate with an external device or system (e.g., an external device or system described herein, including, but not limited to, external device 800, external device 2300, information system 2500, information system 2800, healthcare provider identification device 2900, individual subject identification device 3000, or guest device 3200, or a combination thereof). Such communication can include, for example, indications that the circuitry 106 is accessing one or more databases or memory devices storing reference or programming data, computational protocols, system updates, or the like.

The reference data includes data indicative of one or more physical characteristics associated with an identity of at least one individual. For example, the reference data can include, but is not limited to, a skin topography feature associated with an identity of an individual, a skin surface pattern associated with an identity of an individual, a follicle pattern associated with an identity of an individual, a pore pattern associated with an identity of an individual, a pigmentation pattern or characteristic associated with an identity of an individual, a vascular layout associated with an identity of an individual, an electric current pattern associated with an identity of an individual, a photovoltaic current pattern associated with an identity of an individual, a skin resistivity measurement associated with an identity of an individual, or the like. For example, the reference data can include one or more physical characteristics associated with a first person/individual, one or more physical characteristics associated with a second person/individual, one or more physical characteristics associated with a third person/individual, and so on. The circuitry 106 is configured to compare the identity sense signals from the sensor assembly 104 to the reference data, such that when the comparison is at or exceeds a threshold correspondence (e.g., within a predetermined confidence interval), the identity of the person/individual stored by the reference data can be attributed to the individual on which the system 100 is positioned. For example, if the reference data includes physical characteristic information for each of Dr. Bob, Dr. Jan, and Nurse Joe, the circuitry 106 can compare the identity sense signals from the sensor assembly 104 to determine whether the identity sense signals would correspond to the physical characteristic information of Dr. Bob, Dr. Jan, or Nurse Joe. In another example, if the reference data includes physical characteristic information for each of patients Greg, Joe, and Lisa, the circuitry 106 can compare the identity sense signals from the sensor assembly 104 to determine whether the identity sense signals would correspond to the physical characteristic information of Greg, Joe, or Lisa.

As described herein, the reporter 108 of the system 100 is configured to generate one or more communication signals to report information associated with operation of the system 100. In an embodiment, the reporter 108 is operably coupled to the circuitry 106 and is configured to generate one or more communication signals responsive to instruction by the circuitry 106. The communication signals can be associated with the one or more identity sense signals generated by the sensor assembly 104 (e.g., via the one or more identity sensors 200 or the one or more identity sensors 2100), with a comparison of the one or more identity sense signals with the one or more physical characteristics associated with the identity of the at least one individual (e.g., as provided by the circuitry 106 to determine whether the one or more identity signals correspond to the identity of the at least one individual), or a combination thereof. For example, the reporter 108 can report that the individual on which the system 100 is placed corresponds to a first individual (e.g., it is Dr. Bob), the reporter 108 can report that the information transmitted is a second individual's physical characteristics (e.g., this information corresponds to the skin topography feature of Dr. Jan), the reporter 108 can report that the system 100 is unable to determine an identity of the individual (e.g., the physical characteristics measured by the sensor assembly 104 do not correspond to, or do not meet a threshold correspondence to, any of Dr. Bob, Dr. Jan, or Nurse Joe), or the like. In another example, the reporter 108 can report that a second individual being evaluated or cared for by the individual on which the system 100 is placed corresponds to a first individual (e.g., it is patient Greg), the reporter 108 can report that the information transmitted is a second individual's physical characteristics (e.g., this information corresponds to the skin topography feature of patient Joe), the reporter 108 can report that the system 100 is unable to determine an identity of the individual (e.g., the physical characteristics measured by the sensor assembly 104 do not correspond to, or do not meet a threshold correspondence to, any of patients Greg, Joe, or Lisa), or the like.

In an embodiment, the reporter 108 is configured to generate the one or more communication signals prior to or in conjunction with an authorization of the healthcare provider to perform a health service action with respect to an individual subject. For example, the one or more communication signals can include an authorization signal reported to an external device or system, the one or more communication signals can include one or more signals associated with a comparison between identity sense signals or an identity of the healthcare provider with one or more authorization parameters, the one or more communication signals can include an identity or identity sense signals reported to an external device or system that is configured to determine whether the healthcare provider is authorized to perform the health service action with respect to the individual subject, or a combination thereof (e.g., partial authorization by system 100 and partial authorization by external device or system). Health service actions the healthcare provider can be authorized to perform with respect to the individual subject include, but are not limited to, operating an external device (e.g., external device 800 or external device 2300 described herein), performing a scheduled procedure, providing a treatment, accessing information associated with the individual subject (e.g., via information system 2500 or information system 2800 described herein), or the like.

In an embodiment, the one or more communication signals correspond to a lack of authorization of the healthcare provider to perform a health service action with respect to an individual subject responsive to a correspondence between one or more identity sense signals and reference data indicative of one or more physical characteristics associated with an identity of at least one individual being below a threshold correspondence. For example, the reporter 108 can be configured to generate one or more communication signals corresponding to a lack of authorization for the individual on which the system 100 is placed to perform or participate in a health service action when the identity sense signals do not correspond to reference data indicative of one or more physical characteristics associated with the identity of Dr. Bob, that is, when the individual on which the system 100 is placed cannot be identified as Dr. Bob. In an embodiment, the one or more communication signals correspond to authorization of the healthcare provider to perform a health service action with respect to an individual subject responsive to a correspondence between one or more identity sense signals and reference data indicative of one or more physical characteristics associated with an identity of at least one individual at least at a threshold correspondence. For example, the reporter 108 can be configured to generate one or more communication signals corresponding to an authorization for the individual on which the system 100 is placed to perform or participate in a health service action when the identity sense signals meet a threshold correspondence to reference data indicative of one or more physical characteristics associated with the identity of Dr. Bob, that is, when the individual on which the system 100 is placed can be identified as Dr. Bob.

In an embodiment, the one or more communication signals correspond to a lack of authorization of the healthcare provider to perform a health service action with respect to an individual subject responsive to a correspondence between one or more identity sense signals associated with the individual subject and reference data indicative of one or more physical characteristics associated with the identity of at least one individual being below a threshold correspondence. For example, the reporter 108 can be configured to generate one or more communication signals corresponding to a lack of authorization for the individual on which the system 100 is placed to perform or participate in a health service action when identity sense signals associated with a second individual (e.g. a patient evaluated by the system 100, where the system 100 is placed on a healthcare provider, as shown in FIGS. 22A and 22B) do not correspond to reference data indicative of one or more physical characteristics associated with the identity of patient Greg, that is, when the individual being evaluated or cared for by the individual on which the system 100 is placed cannot be identified by system 100 as patient Greg. In an embodiment, the one or more communication signals correspond to an authorization of the healthcare provider to perform a health service action with respect to an individual subject responsive to a correspondence between one or more identity sense signals associated with the individual subject and reference data indicative of one or more physical characteristics associated with the identity of at least one individual being at least at a threshold correspondence. For example, the reporter 108 can be configured to generate one or more communication signals corresponding to an authorization for the individual on which the system 100 is placed to perform or participate in a health service action when identity sense signals associated with a second individual (e.g. a patient evaluated by the system 100, where the system 100 is placed on a healthcare provider, as shown in FIGS. 22A and 22B) meet a threshold correspondence with reference data indicative of one or more physical characteristics associated with the identity of patient Greg, that is, when the individual being evaluated or cared for by the individual on which the system 100 is placed can be identified as patient Greg.

In an embodiment, the one or more communication signals correspond to authorization of the healthcare provider to perform the health service action with respect to the individual subject responsive to both of (i) a correspondence between one or more identity sense signals associated with the individual on which the system 100 is placed and reference data indicative of one or more physical characteristics associated with the identity of the at least one individual being at least at a threshold correspondence (e.g., individual on which the system 100 is placed can be identified as Dr. Bob) and (ii) a correspondence between one or more second identity sense signals associated with an individual subject (e.g. a patient scanned by the system 100, where the system 100 is placed on a healthcare provider, as shown in FIGS. 22A and 22B) and reference data indicative of one or more physical characteristics associated with the identity of the at least one second individual being at least at a threshold correspondence (e.g., a second individual being evaluated or cared for by the individual on which the system 100 is placed can be identified as patient Greg).

In embodiments, the reporter 108 is configured to report the one or more communications signals to identify the healthcare provider (or an individual subject being evaluated or cared for by the healthcare provider) for authorization by an external device or system, to request authorization from an external device or system for the healthcare provider to perform the health service action (e.g., based on identity, identity sense signals, or an associated comparison), or at least partially authorizing the healthcare provider to perform the health service action with respect to an individual subject. For example, the reporter 108 can report one or more communications signals identifying Dr. Bob or patient Greg to an external device or system, requesting authorization from the external device or system for Dr. Bob to perform a scheduled surgical procedure on patient Greg, or at least partially authorizing Dr. Bob to perform the scheduled surgical procedure on patient Greg.

In an embodiment, the communication signals are reportable to an external device or system (e.g., an external device or system described herein, including, but not limited to, external device 800, external device 2300, information system 2500, information system 2800, healthcare provider identification device 2900, individual subject identification device 3000, or guest device 3200, or a combination thereof). For example the external device or system can include, but is not limited to, a computing device, system or network (e.g., a personal computing device, a server, electronic health records system, a billing system, a scheduling system, an inventory management system, a claim processing system, an administrative system, etc.), or an electronic device (e.g., an electronic controller such as on a medical device, surgical device, a therapeutic device, an assistive device, an imaging device, a rehabilitative device, a drug delivery tool, vending machine, display device, or other electronic equipment). In an embodiment, the system 100 can transmit the one or more communication signals to a computing device having at least one of circuitry or programming that collects data from one or more wearable sensors that are part of the system 100 or are otherwise associated with the individual on which the system 100 is positioned, so that the computing device can associate data within the communication signals with the individual. The system 100, via the reporter 108, can transmit identity information to an electronic controller equipped with authorization capabilities for employment in authorizing use of one or more devices, programs, device functionalities, or the like, by the identified individual. For example, the system 100 can transmit information that the individual is identified as Dr. Bob, whereby the electronic controller can facilitate use of one or more devices, programs, device functionalities by Dr. Bob, according to his identity.

In an embodiment, shown in FIG. 7, the reporter 108 includes one or more of a transmitter 700, a transceiver 702, or a receiver 704. For example, as described herein, the reporter 108 can include an antenna structure configured to at least one of transmit the one or more communication signals (e.g., via the transmitter 700, the transceiver 702, etc.) or receive one or more communication signals from an external device (e.g., via the transceiver 702, the receiver 704, etc.). The one or more communication signals from the external device can include but are not limited to, control programming, authorization parameters, reference data, or a query (e.g., a query to transmit information from the system 100 to the external device). In an embodiment, the sensor assembly 104 includes one or more of a transceiver (e.g., transceiver 702) or a receiver (e.g., receiver 704) configured receive one or more communication signals from an external device. For example, the one or more communication signals from the external device can include but are not limited to, control programming, authorization parameters, reference data, or a query (e.g., a query for one or more communication signals associated with an identity or identity sense signals, or a query to begin sensing physical characteristics of the healthcare provider on which the system 100 is positioned).

Figure 23:
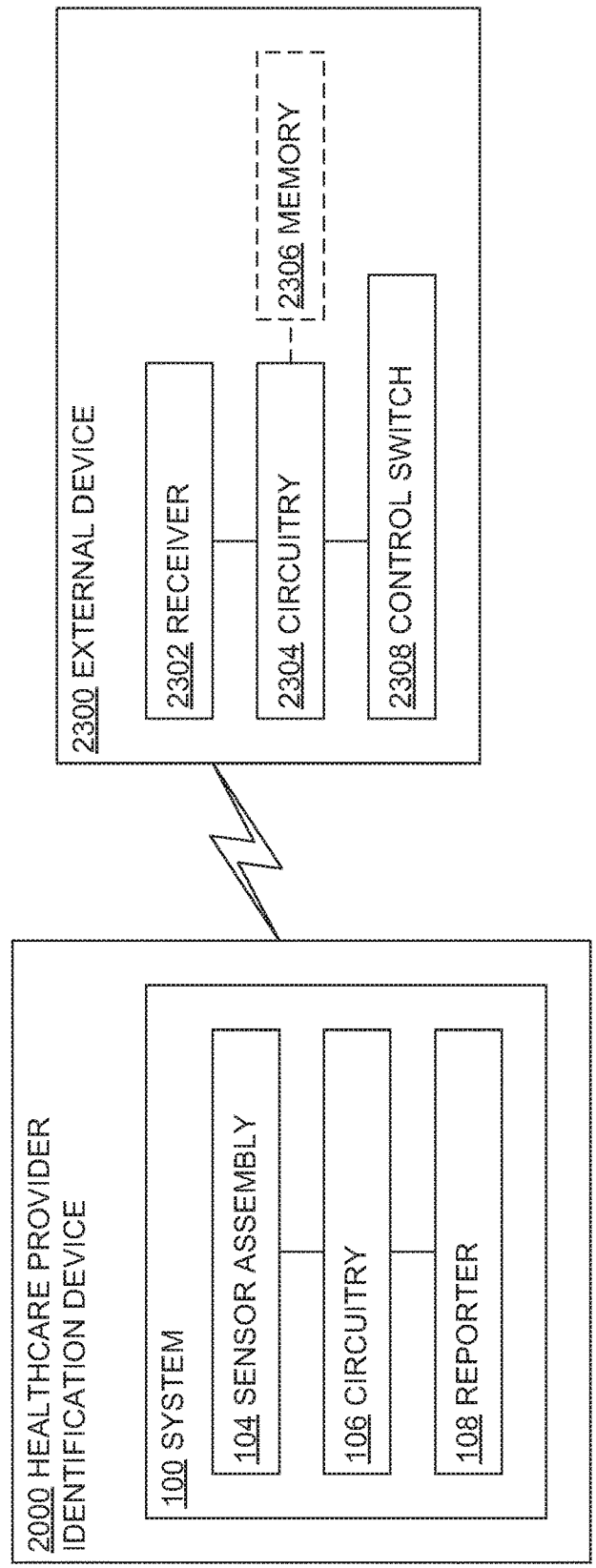
FIG. 23 is a schematic of an embodiment of a healthcare provider identification device such as shown in FIG. 20 and an external device in communication with the healthcare provider identification device.

In an embodiment, shown in FIG. 23, the healthcare provider identification device 2000 is configured to communicate with an external device or system (referred to herein as external device 2300). The external device 2300 is configured to receive communications from the reporter 108 for analysis by the external device 2300. The external device 2300 can include a receiver 2302 (e.g., receiving antenna, transceiver, etc.) configured to receive the one or more communication signals from the reporter 108. The external device 2300 can also include circuitry 2304 configured to compare the one or more communication signals with one or more authorization parameters associated with one or more users authorized to operate the external device 2300. For example, the external device 2300 can include, or can access, a computer memory device 2306 that maintains data associated with authorization parameters pertinent to operation of the external device 2300. The authorization parameters can include but are not limited to, a list of identified individuals, identities, devices, or systems authorized to operate at least a portion of features of the external device 2300, a list of reference physical characteristics for one or more users authorized to operate the external device 2300, a list of functionalities of the external device 2300 that identified individuals are authorized to utilize, or the like. For example, the external device 2300 can receive the communication signals from the reporter 108 indicating an identity of the healthcare provider on whom the deformable substrate 102 is positioned, whereby the external device 2300 can compare (e.g., via the circuitry 2304) the identity of the individual with the authorization parameters stored in the memory 2306 to determine whether the identified individual is authorized to operate the external device 2300, to determine which functionalities of the external device 2300 the identified individual is authorized to operate, or the like. As another example, where the authorization parameters includes a list of identified devices or systems, such devices or systems can automatically operate the portion of features of the external device 2300, such as without interaction with the healthcare provider or other individual. In an embodiment, the external device 2300 includes a control switch 2308 for turning at least a portion of the external device 2300 on or off, or partially enabling or disabling one or more functionalities of the external device 2300 based on a comparison of the identity or identity sense signals with one or more authorization parameters, or based on whether or not the individual on whom the deformable substrate 102 is positioned is identified to the external device 2300 as having authorization to operate the external device 2300.

In an embodiment, shown in FIG. 24, the external device includes, but is not limited to, a medical device 2400 (e.g., invasive medical device or non-invasive medical device (e.g. gamma knife)), surgical device 2402 (e.g., an endoscopic tool, saw, gamma knife, stapling or suturing device, robotic surgical tool, etc.), a therapeutic device 2406, an assistive device 2410 (e.g., an ambulatory assistive device, an assistive speaking device, an assistive hearing device, an assistive vision device, etc.), an imaging device 2404 (e.g., a X-ray device, a magnetic resonance imaging (MRI) device, an ultrasound device, an endoscopy device, an elastography device, a tactile imaging device, a thermography device, a positron emission tomography (PET) device, single-photon emission computed tomography (SPECT) device, etc.), a rehabilitative device 2412, a drug delivery tool 2408 (e.g., a pill dispenser, peristaltic pump, syringe, etc.), a vending machine 2414 (e.g., vending machine for drugs, medical equipment (e.g., disposable or reusable tools, bandages, and the like) or consumables (e.g., candy, food, beverages, and the like)), a display device 2416, or any combination thereof. In an embodiment, the display device 2416 can include, but is not limited to, a liquid crystal display (LCD), an LED display 2420, and OLED display 2422, a touchscreen assembly 2424 (e.g., resistive or capacitive touch panel), a projection-based display 2426 (e.g., a built-in projection display (e.g., projection display 2106 of display device 1200 described herein), an external projection display, a heads-up display device, or the like), an interactive drape 2428 (e.g., an interactive surgical drape or patient room drape with a projected display or including an embedded flexible display). In an embodiment, the display device 2416 can be configured as a virtual reality or augmented reality display. For example, the display device 2416 can be configured to display a virtual reality environment or an augmented reality environment. The display device 2416 can be configured to display the virtual reality or augmented reality environment with one or more display features or functionalities associated with one or more authorization parameters for the identified individual. For example, an individual identified as Dr. Bob can access full functionality of a surgical simulator, while an individual identified as Nurse Joe is denied access to one or more features or functions of the surgical simulator.

In embodiments, the external device 2300 can include, but is not limited to, a communication device or electronic equipment, such as one or more of a mobile communication device or a computer system including, but not limited to, mobile computing devices (e.g., hand-held portable computers, Personal Digital Assistants (PDAs), laptop computers, netbook computers, tablet computers, or so forth), mobile telephone devices (e.g., cellular telephones and smartphones), devices that include functionalities associated with smartphones and tablet computers (e.g., phablets), portable game devices, portable media players, multimedia devices, satellite navigation devices (e.g., Global Positioning System (GPS) navigation devices), e-book reader devices (eReaders), Smart Television (TV) devices, surface computing devices (e.g., table top computers), Personal Computer (PC) devices, devices that employ touch-based human interfaces, currency-handling devices (e.g., automated teller machines (ATMs), cash registers, coin/bill counters and sorters, credit/debit card readers, etc.), a motorized vehicle or control systems thereof (e.g., car, truck, motorcycle, boat, snowmobile, airplane, helicopter, etc.), exercise facilities or equipment, a home security system, an electronic medication dispenser (e.g., pill dispenser), medical treatment facilities or equipment (e.g., patient suites, surgical suites, surgical equipment, etc.), rental equipment with a user interface (e.g., video rentals, audio rentals, etc.), transportation security terminals (e.g., airport security terminal, train security terminal, ferry security terminal, etc.), personnel-tracking equipment, heavy or specialized machinery, specialized tools, safety equipment, security equipment (e.g., a lock or access point), medical equipment (e.g., drug delivery devices or surgical tools), or personal equipment or clothing having customizable electronic features. The reporter 108 can communicate (e.g., send and receive communication signals) with the external device 2300 via one or more connected or wireless communication mechanisms including, but not limited to acoustic communication signals, sound communication signals (e.g., audible, inaudible, or combinations thereof), optical communication signals, radio communication signals, infrared communication signals, ultrasonic communication signals, electric signals (e.g., via a conduction pathway between a component of the system 100 and the external device 2300), and the like. In an embodiment, one or more of the sensor assembly 104 or the circuitry 106 can receive communication signals from the external device 2300. For example, the external device 2300 (e.g., a cellular or network-based device) can transmit one or more communication signals to one or more of the sensor assembly 104 or the circuitry 106, where such communication signals can initiate or terminate particular functionalities of the sensor assembly 104 or circuitry 106 (e.g., turn on/off), provide programming information, provide updated functionalities, provide or update comparison threshold values or reference data, or the like. In an embodiment, the circuitry 106 directs the reporter 108 to generate the one or more communication responsive to a query from the external device 2300. In an embodiment, the reporter 108 generates the one or more communication signals responsive to instruction by the circuitry 106 without any dependence or communication from the external device 2300. For example, the reporter 108 can generate the one or more communication signals regardless of whether the external device 2300 is capable of receiving the communication signals. In such instances, the communication signals generated by the reporter 108 can be stored in memory of the system 100, where the stored communication signals can be utilized later (e.g., to program one or more new systems 100, external devices 2300, etc.).

As described herein and shown in FIG. 10, in an embodiment, the circuitry 106 can include an identity comparison module 1000 and an authorization comparison module 1002. The identity comparison module 1000 is configured to compare the one or more identity sense signals generated by the sensor assembly 104 to reference data indicative of one or more physical characteristics associated with an identity of at least one individual to determine whether the one or more identity sense signals correspond to the identity of the at least one individual. For example, the identity comparison module 1000 can include structure and functionality similar to, or the same as, the comparison module 400 described herein. The reference data indicative of one or more physical characteristics associated with an identity of at least one individual can be stored in a computer memory device 1004 accessible by the circuitry 106, the identity comparison module 1000, or the authorization comparison module 1002. For example, the computer memory device 1004 can store data associated with a list of identities (e.g., names of individuals) having associated physical characteristics attributable to the particular identity (e.g., a skin topography feature associated with and unique to a first identity, a skin topography feature associated with and unique to a second identity, and the so forth). The authorization comparison module 1002 is configured to compare at least one of the one or more identity sense signals or the identity of the at least one individual with one or more authorization parameters. In an embodiment, the authorization comparison module 1002 is configured to compare at least one of one or more identity sense signals associated with a healthcare provider on which the system 100 is placed or the identity of healthcare provider with one or more authorization parameters. In an embodiment, the authorization comparison module 1002 is configured to compare at least one of one or more identity sense signals associated with an individual subject being evaluated or cared for by a healthcare provider on which the system 100 is placed or the identity of individual subject with one or more authorization parameters. In embodiments, one or more authorization parameters associated with one or more healthcare providers or other individuals can include, but are not limited to, a list of identified individuals or identities authorized to operate at least a portion of features of the system 100, a list of identified authorized individuals or identities under which at least a portion of features of the system 100 (e.g., reporter 108) will function, a list of identified individuals or identities authorized to operate at least a portion of features of an external device (e.g., external device 800 or external device 2300), a list of reference physical characteristics for one or more users authorized to operate an external device (e.g., external device 800 or external device 2300), a list of functionalities of an external device (e.g., external device 800 or external device 2300) that identified individuals are authorized to utilize, a list of identities of one or more individuals authorized to perform or participate in a scheduled procedure, a list of identities of one or more individuals authorized to access information associated with an individual subject (e.g., a patient), a list of identities of one or more individuals associated with at least one of a time, a date, or a location, a list of reference physical characteristics for one or more individuals authorized to perform a scheduled procedure, a list of reference physical characteristics for one or more individuals authorized to access information associated with the individual subject, or the like. In embodiments, one or more authorization parameters associated with one or more individual subjects (e.g., one or more patients or other individuals) can include, but are not limited to, a list of identities of one or more individuals authorized to undergo a scheduled procedure, a list of identities of one or more individuals scheduled to receive a treatment, a list of identities of one or more individuals with pre-operative permissions or restrictions, a list of identities of one or more individuals with post-operative permissions or restrictions, a list of identities of one or more individuals with pre-treatment permissions or restrictions, a list of identities of one or more individuals with post-treatment permissions or restrictions, at least one authorization parameter associated with at least one of a treatment schedule, a recovery schedule, a rehabilitation schedule, a pre-operative schedule, or a post-operative schedule, a list of identities of one or more individuals assigned to the healthcare provider, a list of identities of one or more individuals associated with at least one of a time, a date, or a location, or the like.

In an embodiment, the reporter 108 is configured to generate the one or more communication signals responsive to instruction by the circuitry 106, where the one or more communication signals are associated with a comparison of at least one of the one or more identity sense signals with the one or more authorization parameters or the identity of the at least one individual with the one or more authorization parameters. For example, instances where the one or more communication signals are based on a comparison of one or more identity sense signals with the one or more authorization parameters, the authorization comparison module 1002 can directly compare the one or more identity sense signals with authorization parameters stored in the memory 1004. The authorization parameters can include a list of physical characteristics of authorized individuals, such that when the identity sense signals match the physical characteristics of authorized individuals stored in memory, the healthcare provider can be authorized. For example, authorization can include, but is not limited to, the individual being authorized to perform or participate in a health service action, to utilize the system 100, or to use an external device (e.g., where the healthcare provider substantially matches one identity of the list of individuals authorized to operate the external device). Also or instead, the system 100 can function fully (e.g., can transmit information) or a portion of the functionalities of the system 100 to which the authorized individual is permitted to utilized are enabled. When the one or more communication signals are based on a comparison of the identity of the at least one individual with the one or more authorization parameters, the identity comparison module 1000 can first identify the individual based on the one or more identity sense signals, whereby the authorization comparison module 1002 can determine whether the identified individual is an authorized individual (e.g., by comparing the identity to reference data having a list of authorized individuals or identities). In an embodiment, when the one or more authorization parameters correspond to a single authorized user, the identity comparison module 1000 and the authorization comparison module 1002 can be incorporated as a single module for automatic authentication after identification.

In an embodiment, shown in FIG. 11, the circuitry 106 includes a comparison module 1100 configured to compare the one or more identity sense signals generated by the sensor assembly 104 to reference data indicative of one or more physical characteristics associated with a physical state of the individual to determine whether the healthcare provider is authorized to operate an external device. For example, the memory 1004 can store reference data associated with physical states including but not limited to, a vital status (e.g., physiological reference data indicative of a living status or a deceased status, physiological data associated with a distress or stress status, or the like) or a functional status (e.g., a physical status, a mental status, or the like). In an embodiment, the comparison module compares sense signals from other sensors of the system (e.g., one or more of the physiological sensor 900, the proximity sensor 902, the contact sensor 904, the pressure sensor 906, or the temperature sensor 908) to determine the vital status or the functional status of the individual. The reference data indicative of one or more physical characteristics associated with a functional status can include but are not limited to, chemical or biological indicators of inebriation or intoxication (e.g., by drugs or alcohol), the presence or absence of a substance (e.g., a toxin, a poison, a prescription medication), a blood oxygenation level, a movement, pattern of movement, or absence of movement (e.g., as indicators of a state of consciousness or of compromised fine motor skills), or so forth. The vital status or the functional status can serve as an indicator as to whether an identified individual is in a state suitable for operation of the external device. While the healthcare provider may be identified and authorized to use an external device (e.g., external device 2300), the current status of the individual may preclude total or partial operation of the external device. For example, the sensors of the system 100 may detect that the healthcare provider has a blood alcohol content making it unsafe for the healthcare provider to perform a scheduled surgical procedure (e.g., using a saw) that the healthcare provider is otherwise authorized to perform. In an embodiment, the system 100 is configured to determine a status of the healthcare provider based on a schedule parameter (e.g., schedule of procedures), logged activity state of the healthcare provider (e.g., logged procedures, which may be stored by logging module 2002), timing information (e.g., check in time, time since last procedure, etc.), or the like. For example, the system 100 may determine that the healthcare provider has been on call for an extended period of time, making it unsuitable for the healthcare provider to perform an elective surgical procedure that the healthcare provider is otherwise authorized to perform. In another example, the system 100 can determine that Dr. Bob has been on call for 32 hours, so he is not authorized for elective surgery. In another example, the system 100 can determine that Dr. Bob performed part A of a treatment (e.g., administered a contrast agent) at 08:00, Dr. Bob or different authorized healthcare provider (e.g., a CT technician) must perform CT scan by 10:00; after 10:00 the system 100 can prevent the CT scan (e.g., by disabling or inhibiting use of CT equipment). In an embodiment, the circuitry 106 is configured to prevent authorization of the healthcare provider to operate at least a portion of the external device responsive to a correspondence between the one or more identity sense signals and the reference data indicative of the one or more physical characteristics associated with the functional status of the individual being above a functional threshold correspondence. For example, the functional threshold correspondence can be related to a safety threshold of a physical characteristic for operation of the external device (e.g., a blood alcohol content, a medication level, etc.). In an embodiment, the circuitry 106 prevents authorization of the healthcare provider by not instructing the reporter 108 to generate or transmit the one or more communication signals. In an embodiment, the circuitry 106 can permit partial authorization of operation of the external device, such that only a subset of functionalities of the external device is available to the healthcare provider for operation. For example, if a healthcare provider is identified and authorized to access patient information (e.g., via a computing device), and the healthcare provider is determined to be intoxicated or to otherwise have a diminished functional status, the circuitry 106 can permit "read only" functionalities, but prevent functionalities associated with adding, changing, or deleting patient information.

As described herein and shown in FIG. 12, in an embodiment, the reporter 108 includes a display device 1200 configured to provide a visual indication associated with an output of the reporter 108. For example, the display device 1200 can include one or more light-emitting elements 1202 (e.g., light-emitting diodes, polymer light-emitting diodes (PLEDs), lasers, or other light source(s)) configured to provide a predetermined pattern of light corresponding to a comparison between at least one of the one or more identity sense signals with the one or more authorization parameters or the identity of the at least one individual with the one or more authorization parameters. The predetermined pattern of light can include patterns associated with light intensity or brightness, color, shapes, or other characteristics discernable between distinct patterns. In an embodiment, the predetermined pattern includes a first pattern associated with a correspondence between at least one of the one or more identity sense signals with the one or more authorization parameters or the identity of the at least one individual with the one or more authorization parameters being below a threshold correspondence (e.g., the physical characteristics measured by the sensor assembly 104 do not correspond to an authorized individual), and the predetermined pattern includes a second pattern associated with a correspondence between at least one of the one or more identity sense signals with the one or more authorization parameters or the identity of the at least one individual with the one or more authorization parameters being at least at the threshold correspondence (e.g., the physical characteristics measured by the sensor assembly 104 correspond to an authorized individual). For example, the reporter 108 can display via the display device a first pattern (e.g., a first intensity, a first color, a first shape, etc.) if the healthcare provider is not authorized to perform a health service action with respect to an individual subject, and can display a distinct second pattern (a second intensity, a second color, a second shape, etc.) if the healthcare provider is authorized to perform the health service action with respect to the individual subject. The system 100 can also include one or more photodetectors, such as one or more organic photodetectors (OPDs), to detect light from the display device 1200 and/or the sensor assembly 104, such as light reflected by or refracted from a body portion. For example, the system 100 can include an organic photodetector comprising an active layer of poly(3-hexylthiophene) (P3HT):(6,6)-phenyl-C61-butyric acid methyl ester (PCBM).

In an embodiment, the display device 1200 can include one or more sound-emitting elements 1204 (e.g., speaker, tone-source, or other sound source(s)) configured to provide a predetermined pattern of sound corresponding to a comparison between at least one of the one or more identity sense signals with the one or more authorization parameters or the identity of the at least one individual with the one or more authorization parameters. The predetermined pattern of sound can include patterns associated with sound intensity, audible and inaudible phases, or other characteristics discernable between distinct patterns. In an embodiment, the predetermined pattern includes a first pattern associated with a correspondence between at least one of the one or more identity sense signals with the one or more authorization parameters or the identity of the at least one individual with the one or more authorization parameters being below a threshold correspondence (e.g., the physical characteristics measured by the sensor assembly 104 do not correspond to an authorized individual), and the predetermined pattern includes a second pattern associated with a correspondence between at least one of the one or more identity sense signals with the one or more authorization parameters or the identity of the at least one individual with the one or more authorization parameters being at least at the threshold correspondence (e.g., the physical characteristics measured by the sensor assembly 104 correspond to an authorized individual). For example, the reporter 108 can display via the display device a first pattern (e.g., a first intensity, a first audible/inaudible pattern, etc.) if the healthcare provider is not authorized to perform a health service action with respect to an individual subject, and can display a distinct second pattern (a second intensity, a second audible/inaudible pattern, etc.) if the healthcare provider is authorized to perform the health service action with respect to an individual subject.

In an embodiment, the display device 1200 includes a projection display 1206 configured to provide a visual indication associated with an output of the reporter 108. For example, the projection display 1206 can be configured to provide a projected image (e.g., projected onto a skin surface, onto a clothing item or garment, onto a wall or support surface, onto a screen, drape, etc.) corresponding to a comparison between at least one of the one or more identity sense signals with the one or more authorization parameters or the identity of the at least one individual with the one or more authorization parameters.

In an embodiment, the circuitry 106 is configured to determine whether the deformable substrate 102 has been removed from the skin surface of the healthcare provider. For example, the system 100 can include, as a part of the sensor assembly 104, distinct from the sensor assembly 104, or a combination thereof, one or more of a strain gauge or a proximity sensor configured to sense whether the deformable substrate 102 has been removed from the skin surface of the healthcare provider. For example, the system 100 can include a computer memory device storing reference data associated with strain or distance measurements corresponding to removal of the deformable substrate 102 from a skin surface. The circuitry 106 can compare the output from the strain gauge or proximity sensor to such reference data to determine whether the deformable substrate 102 has been removed. In an embodiment, the circuitry 106 is configured to determine whether the deformable substrate 102 has been applied to a skin surface that differs from the skin surface of the healthcare provider. For example, the system 100 can store in a computer memory device the one or more identity sense signals obtained by the sensor assembly 104 at a first time, whereby the circuitry 106 can compare one or more identity sense signals obtained by the sensor assembly 104 at a second time to the stored identity sense signals obtained by the sensor assembly 104 at the first time to determine whether the signals substantially differ. If the signals are directed to a skin property, a substantial difference between signals obtained at differing times can indicate that the skin surface differs between the first time and the second, which can indicate that the system 100 was transferred between different individuals between the first time and the second time.

The reporter 108 can generate the one or more communication signals responsive to a variety of scenarios involving one or more of identification or authorization. For example, in an embodiment, the one or more communication signals generated by the reporter 108 correspond to a lack of authorization of the healthcare provider to perform a health service action (e.g., operate an external device, etc.) responsive to a correspondence between the one or more identity sense signals and the reference data indicative of one or more physical characteristics associated with the identity of the at least one individual being below a threshold correspondence. For example, when the circuitry 106 (e.g., via the identity comparison module 1000) is unable to identify the healthcare provider on which the system 100 is positioned, the reporter 108 can report via the communication signals that the healthcare provider is not authorized to perform the health service action on the basis that such healthcare provider is not recognizable. In an embodiment, when the circuitry 106 (e.g., via the identity comparison module 1000) is unable to identify the healthcare provider on which the system 100 is positioned, the circuitry 106 prevents generation of the communication signals by the reporter 108 (e.g., no instruction from the circuitry 106 to the reporter 108 regarding generation of the one or more communication signals). In an embodiment, the one or more communication signals generated by the reporter 108 correspond to authorization of the healthcare provider to perform a health service action responsive to both of (i) a correspondence between the one or more identity sense signals and the reference data indicative of one or more physical characteristics associated with the identity of the at least one individual being at least at a threshold correspondence and (ii) a correspondence between at least one of the one or more identity sense signals or the identity of the at least one individual with one or more authorization parameters being at least at a threshold correspondence. For example, when the circuitry 106 is able to identify the healthcare provider on which the system 100 is positioned (e.g., via the identity comparison module 1000) and the circuitry 106 is able to authorize the healthcare provider on which the system 100 is positioned for operation of the external device (e.g., via the authorization comparison module 1002), the reporter 108 can report via the communication signals that the healthcare provider is authorized to perform a health service action with respect to an individual subject, operate an external device, or participate in any other activity requiring authorization of the healthcare provider.

In an embodiment, the reporter 108 is configured to provide a static output of communication signals. In an embodiment, the reporter 108 is configured to continuously generate the one or more communication signals. In an embodiment, the reporter 108 is configured to provide a dynamic output of communication signals. In an embodiment, the reporter 108 is configured to generate the one or more communication signals responsive to a query from an external device or system (e.g., an external device or system described herein, including, but not limited to, external device 800, external device 2300, information system 2500, information system 2800, healthcare provider identification device 2900, individual subject identification device 3000, or guest device 3200, or a combination thereof). In an embodiment, the reporter 108 is configured to generate the one or more communication signals responsive to a proximity between the reporter 108 and an external device or system (e.g., an external device or system described herein, including, but not limited to, external device 800, external device 2300, information system 2500, information system 2800, healthcare provider identification device 2900, individual subject identification device 3000, or guest device 3200, or a combination thereof). For example, the system 100 can include a proximity sensor (e.g., proximity sensor 902) configured to generate sense signals indicative of proximity between the reporter 108 and an external device or system (e.g., an external device or system described herein, including, but not limited to, external device 800, external device 2300, information system 2500, information system 2800, healthcare provider identification device 2900, individual subject identification device 3000, or guest device 3200, or a combination thereof). The circuitry 106 can compare the sense signals from the proximity sensor to reference data (e.g., a threshold proximity) to determine whether the reporter 108 and the external device or system are close enough to begin transmission of communication signals from the reporter 108 to the external device or system, and instruct the reporter 108 to generate the one or more communication signals when it is determined that the reporter 108 and the external device or system are within a threshold proximity.

Figure 25:
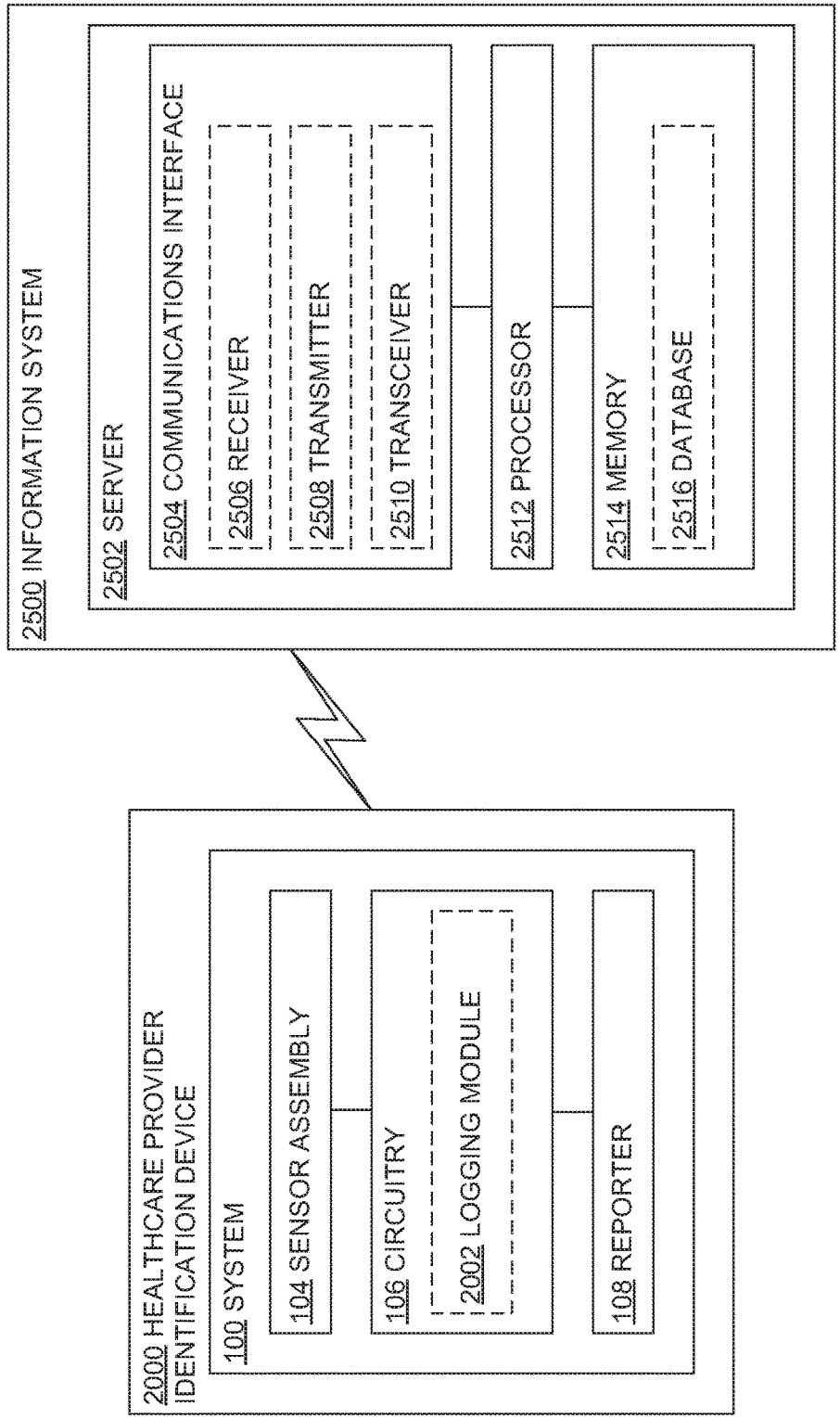
FIG. 25 is a schematic of an embodiment of a healthcare provider identification device such as shown in FIG. 20 and an information system in communication with the healthcare provider identification device.

In an embodiment, shown in FIG. 25, the healthcare provider identification device 2000 is configured to communicate with an information system 2500. The information system 2500 is configured to receive communications from the reporter 108 for analysis by the information system 2500. The information system 2500 can include at least one server 2502 (e.g., a computing device or network of computing devices) having a communications interface 2504 (e.g., a receiver 2506, transmitter 2508, transceiver 2510, or any combination thereof) and at least one processor 2512 (or controller) in communication with a memory 2514. The memory 2514 can include a database 2516 configured to store information received by the information system 2500, authorization parameters, activity logs, and so forth. The information system 2500 can be configured to receive (e.g., via communications interface 2504) one or more communication signals from the reporter 108. The information system 2500 can also include circuitry (e.g., processor 2512) configured to compare the one or more communication signals with one or more authorization parameters. For example, the database 2516 can maintain data associated with authorization parameters pertinent to performing health service actions, operation of external devices, accessing information (e.g., patient health records, billing information, inventory data, etc.). In an embodiment, the information system 2500 can receive the communication signals from the reporter 108 indicating an identity of the healthcare provider on whom the deformable substrate 102 is positioned or an identity of a second individual being evaluated or cared for by the healthcare provider, whereby the information system 2500 can compare (e.g., via processor 2512) the identity with authorization parameters stored in the memory 2514 to determine whether the healthcare provider is authorized to perform a health service action, operate an external device, or access information via the information system 2500, or perform any other activity requiring authorization of the healthcare provider.

In an embodiment, the information system 2500 can generate (e.g., via communications interface 2504) one or more communication signals associated with whether healthcare provider is authorized to perform a health service action, operate an external device, or access information via the information system 2500, or perform any other activity requiring authorization of the healthcare provider. For example, the information system 2500 can transmit (e.g., via communications interface 2504) one or more communication signals to the healthcare provider identification device 2000 or to an external device or system (e.g., external device 800, external device 2300, a second healthcare provider identification device 2900, or a second information system 2800, or the like). In an embodiment, the information system 2500 can transmit (e.g., via communications interface 2504) the one or more authorization parameters to the healthcare provider identification device 2000 or to an external device or system (e.g., external device 800, external device 2300, a second healthcare provider identification device 2900, or a second information system 2800, or the like), whereby the device or system receiving the one or more authorization parameters can perform a comparison between the one or more authorization parameters and the identity or identity sense signals associated with the individual (e.g., the healthcare provider on which the system 100 is placed or a second individual being evaluated or cared for by the healthcare provider).

Figure 26:
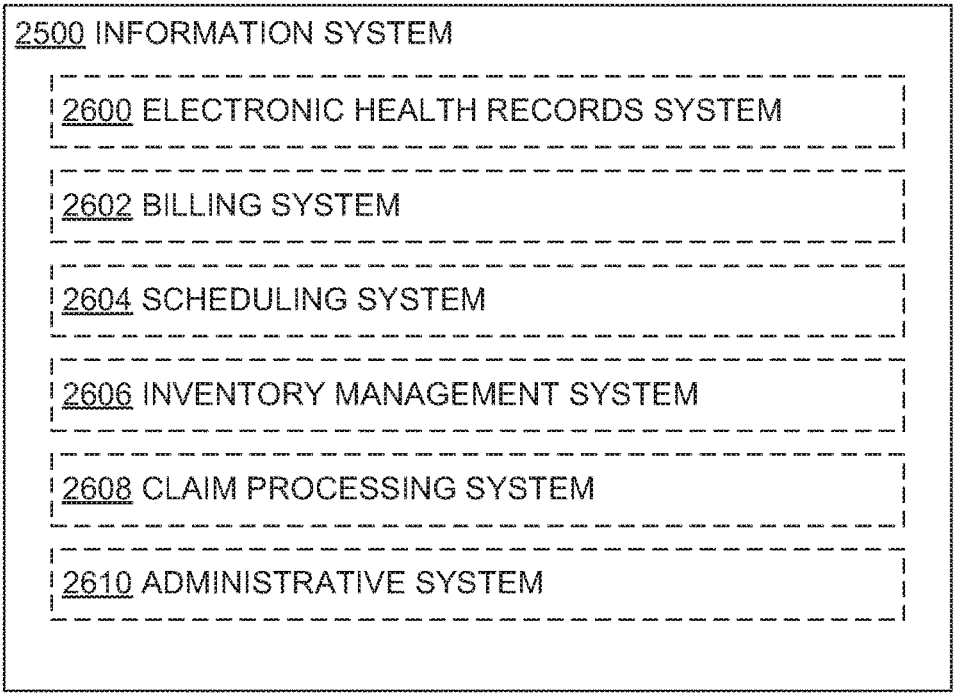
FIG. 26 is a schematic of an embodiment of an information system such as shown in FIG. 25.

In an embodiment, shown in FIG. 26, the information system 2500 includes, but is not limited to, an electronic health records system 2600, a billing system 2602 (e.g., invoicing system for patients, insurance entities, other medical facilities (e.g., labs), etc.), a scheduling system 2604 (e.g., patient scheduling system, doctor or staff scheduling system, room scheduling system, equipment scheduling system, etc.), an inventory management system 2606 (e.g., medical supplies inventory management system, consumables (e.g., food and beverage) inventory management system, drug inventory management system, etc.), a claim processing system 2608 (e.g., insurance claim processing system, tort claim processing system, etc.), or an administrative system 2610 (e.g., hospital administrative system, nurses station computing system or device, receptionist computing system or device, etc.), or any combination thereof. In embodiments, the reporter 108 can communicate (e.g., send and receive communication signals) with the information system 2500 via one or more connected or wireless communication mechanisms including, but not limited to acoustic communication signals, sound communication signals (e.g., audible, inaudible, or combinations thereof), optical communication signals, radio communication signals, infrared communication signals, ultrasonic communication signals, electric signals (e.g., via a conduction pathway between a component of the system 100 and the information system 2500), and the like. In an embodiment, one or more of the sensor assembly 104 or the circuitry 106 can receive communication signals from the information system 2500. For example, the communications interface 2504 (e.g., a cellular or network-based device) can transmit one or more communication signals to one or more of the sensor assembly 104 or the circuitry 106, where such communication signals can initiate or terminate particular functionalities of the sensor assembly 104 or circuitry 106 (e.g., turn on/off), provide programming information, provide updated functionalities, provide or update authorization parameters, comparison threshold values, or reference data, or the like. In an embodiment, the circuitry 106 directs the reporter 108 to generate the one or more communication responsive to a query from the information system 2500. In an embodiment, the reporter 108 generates the one or more communication signals responsive to instruction by the circuitry 106 without any dependence or communication from the information system 2500. For example, the reporter 108 can generate the one or more communication signals regardless of whether the information system 2500 is capable of receiving the communication signals. In such instances, the communication signals generated by the reporter 108 can be stored in memory of the system 100, where the stored communication signals can be utilized later (e.g., to add or modify entries stored in the memory 2514 (e.g., in database 2516) of the information system 2500, etc.).

In an embodiment, shown in FIG. 25, the circuitry 106 of the system 100 includes a logging module 2002 configured to store at least one activity state of the healthcare provider in a memory device of the system 100 (e.g., in memory 402 or memory 1004 described herein, or the like). For example, the logging module 2002 can be configured to store at least one activity state of the healthcare provider including information corresponding to a health service action performed by the healthcare provider. In embodiments, the logging module 2002 can be configured to store at least one activity state of the healthcare provider including, but not limited to, information corresponding to a procedure performed by the healthcare provider, information corresponding to an external device operated by the healthcare provider, information corresponding to supplies (e.g., medical supplies) exhausted by the healthcare provider, information corresponding to one or more individual subjects evaluated by the healthcare provider, or any combination thereof. In an embodiment, the reporter 108 is configured to generate one or more communication signals associated with a logged activity state of the healthcare provider. The reporter 108 can be configured to communicate one or more communication signals associated with a logged activity state of the healthcare provider to the information system 2500. For example, the reporter 108 can transmit one or more communication signals to the information system 2500 indicating that an individual identified as Dr. Bob performed a scheduled surgical procedure at 08:00 that lasted for 4 hours. Responsive to the information system 2500 indicating that an individual identified as Dr. Bob performed a scheduled surgical procedure, the information system 2500 can update one or more database entries (e.g., updates to billing information to account for the procedure, updates to inventory information (e.g., updates based on supplies exhausted for the procedure), updates to scheduling information for the healthcare provider or facilities, updates to patient information (e.g., updates to electronic health records) for the individual on which the procedure was performed, updates to scheduling information (e.g., generating a post-operative schedule) for the individual on which the procedure was performed, and the like).

Figure 27:
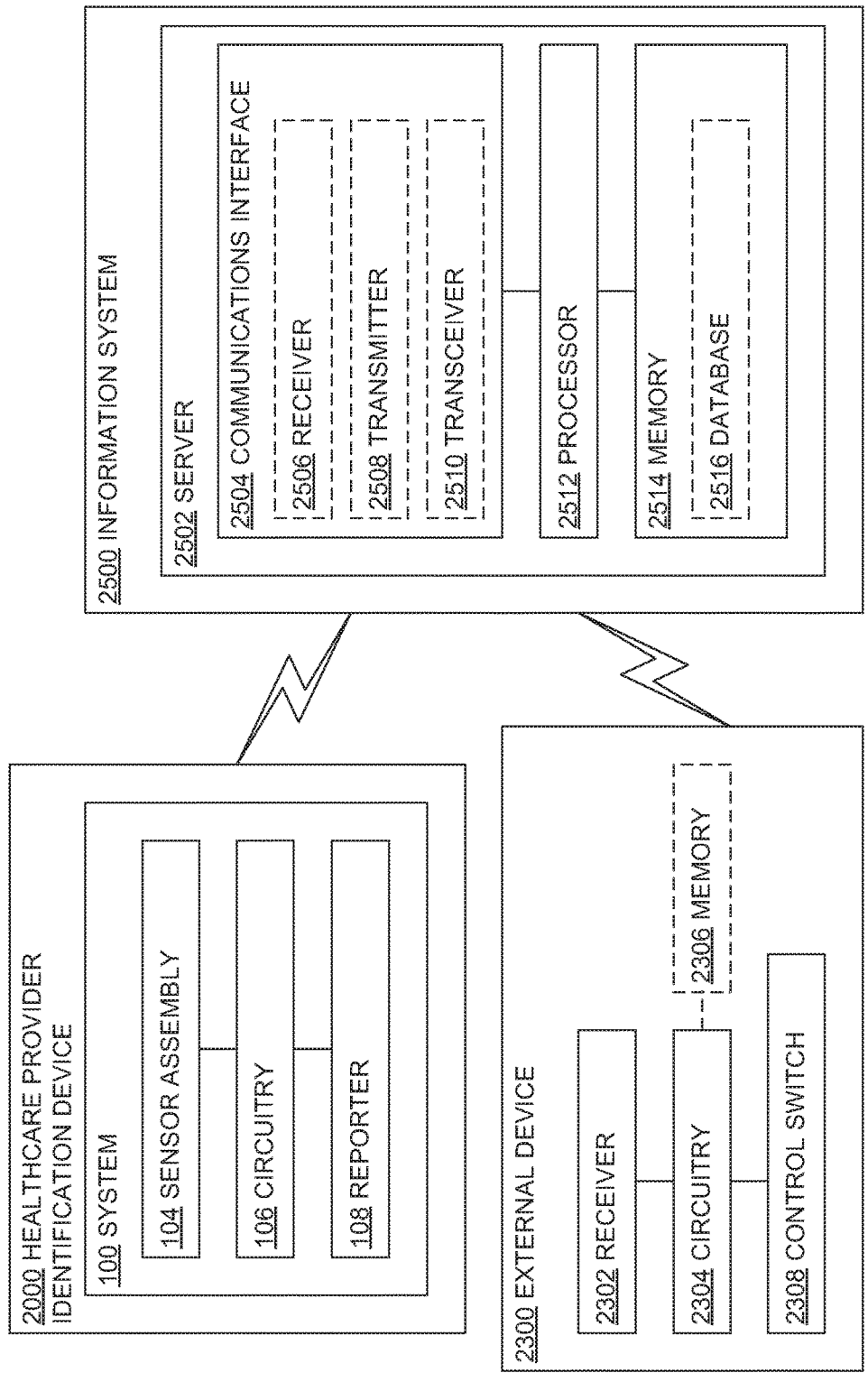
FIG. 27 is a schematic of an embodiment of an information system such as shown in FIG. 25 and a healthcare provider identification device and an external device in communication with the information system.

As shown in FIG. 27, the information system 2500 can be in communication with the healthcare provider identification device 2000 and the external device 2300. In an embodiment, the information system 2500 is configured to facilitate a network connection between the healthcare provider identification device 2000 and the external device 2300. In an embodiment, the information system 2500 is configured to provide one or more communication signals for controlling functionality of the external device 2300 based on the one or more communication signals received from the healthcare provider identification device 2000. For example, the healthcare provider identification device 2000 can transmit one or more communication signals associated with an identity or identity sense signals of the healthcare provider to the information system 2500, whereby the information system 2500 can perform a comparison with one or more authorization parameters. The information system 2500 can send one or more communication signals to the external device 2300 that enable the healthcare provider to fully or partially operate the external device 2300 based on the comparison. For example, the information system 2500 can send one or more communication signals that place the external device 2300 into an operational mode based on receiving one or more communication signals from the healthcare provider identification device 2000 indicating that an individual on which the healthcare provider identification device 2000 is placed can be identified as Dr. Bob.

Figure 28:
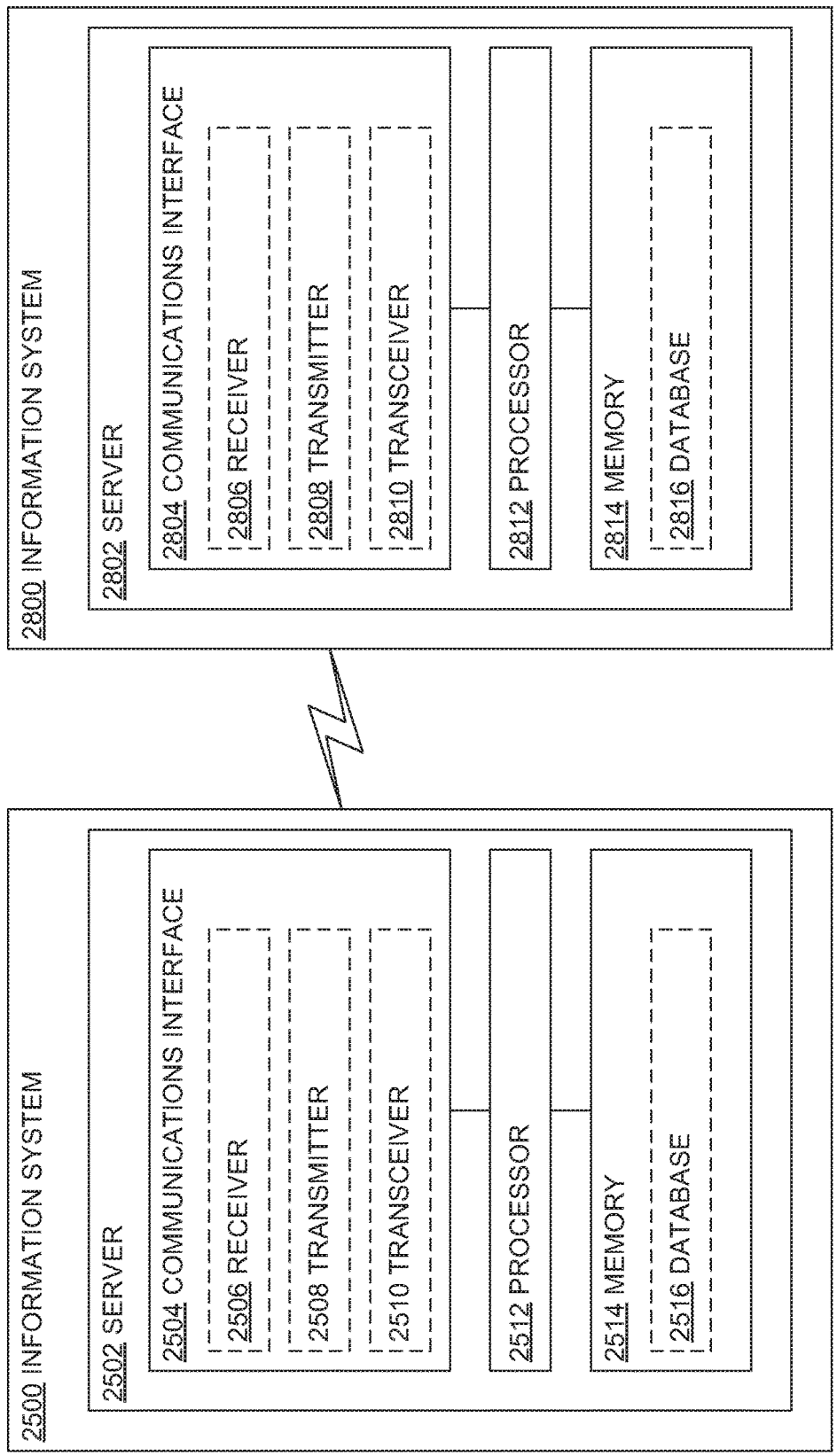
FIG. 28 is a schematic of an embodiment of a first information system such as shown in FIG. 25 and a second information system in communication with the first information system.

As shown in FIG. 28, the information system 2500 can be in communication with at least one other information system 2800, which may have similar structure and functionality to information system 2500. The information system 2800 can be configured to send communications to or receive communications from the information system 2500 and other devices or systems (e.g., external device 800, healthcare provider identification device 2000, healthcare provider identification device 2900 individual subject identification device 3000, guest identification device 3200, or the like). In an embodiment, the information system 2800 can include at least one server 2802 (e.g., a computing device or network of computing devices) having a communications interface 2804 (e.g., a receiver 2806, transmitter 2808, transceiver 2810, or any combination thereof) and at least one processor 2812 (or controller) in communication with a memory 2814. The memory 2814 can include a database 2816 configured to store information received by the information system 2800, authorization parameters, activity logs, and so forth. In an embodiment, the information system 2800 includes, but is not limited to, an electronic health records system, a billing system, a scheduling system, an inventory management system, a claim processing system, an administrative system, or any combination thereof. In an embodiment, the information system 2500 includes one of an electronic health records system, a billing system, a scheduling system, an inventory management system, a claim processing system, or an administrative system, and the information system 2800 includes a different one of an electronic health records system, a billing system, a scheduling system, an inventory management system, a claim processing system, or an administrative system. The information system 2500 can be configured to transmit one or more communication signals to the information system 2800 in response to one or more communications received from an external device (e.g., external device 800, healthcare provider identification device 2000, healthcare provider identification device 2900, individual subject identification device 3000, guest identification device 3200, or the like). For example, the first information system 2500 (e.g., a scheduling system) receives one or more communication signals from the healthcare provider identification device 2000 indicating that an individual on which the healthcare provider identification device 2000 is placed can be identified as Dr. Bob, and in response, the information system 2500 can transmit one or more communication signals associated with one or more procedures Dr. Bob is scheduled to perform to the second information system 2800 (e.g., a hospital administrative system, a billing system, or the like).

Figure 29A:
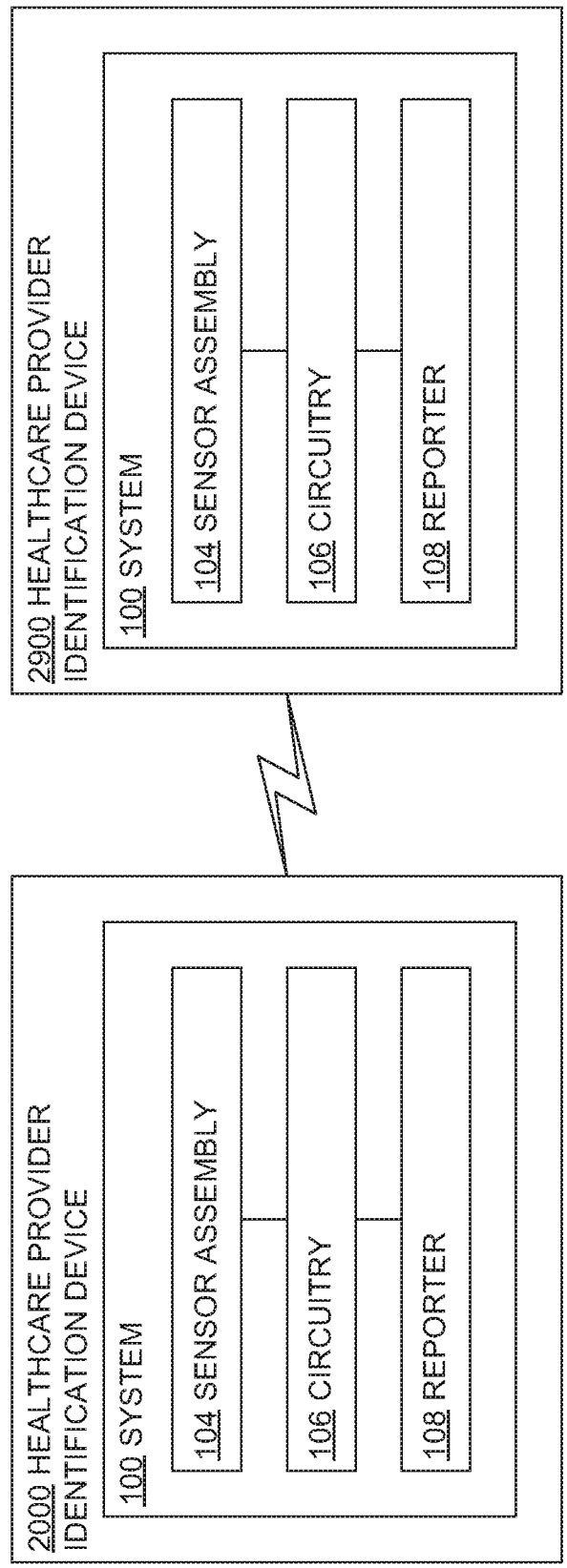
FIG. 29A is a schematic of an embodiment of a first healthcare provider identification device such as shown in FIG. 20 and a second healthcare provider identification device in communication with the first healthcare provider identification device.

In an embodiment, shown in FIG. 29A, the healthcare provider identification device 2000 is configured to communicate with another healthcare provider identification device 2900. The healthcare provider identification device 2900 can have structure and functionality that is the same as or similar to healthcare provider identification device 2000. For example, the healthcare provider identification device 2900 can also include a system, such as the system 100 described herein to facilitate the identification of a healthcare provider. In an embodiment, healthcare provider identification device 2900 is configured to generate (e.g., via reporter 108) one or more communication signals associated with an identity of a second healthcare provider or associated with identity sense signals corresponding to one or more physical characteristics of the second healthcare provider. The healthcare provider identification device 2000 can be configured to receive (e.g., via receiver 404 or transceiver 406 of circuitry 106) the one or more communication signals from healthcare provider identification device 2900, whereby the healthcare provider identification device 2000 can be configured to generate one or more communication signals (e.g., via reporter 108) corresponding to an authorization of the second healthcare provider to perform or participate in a health service action if the identity or identity sense signals generated by healthcare provider identification device 2900 are at least at a threshold correspondence with reference data (e.g., reference physical characteristics, authorization parameters, or the like). For example, when healthcare provider identification device 2000 is placed on an individual identified as Dr. Bob, the individual on which healthcare provider identification device 2900 is placed can be authorized to draw blood from patient Greg when healthcare provider identification device 2000 receives one or more communication signals identifying the individual as Nurse Joe. When the individual is not identified as Nurse Joe, healthcare provider identification device 2000 can be configured to provide an alert (e.g., via reporter 108) to Dr. Bob (e.g., via display device 1200), or to an external device or system.

Figure 29B:
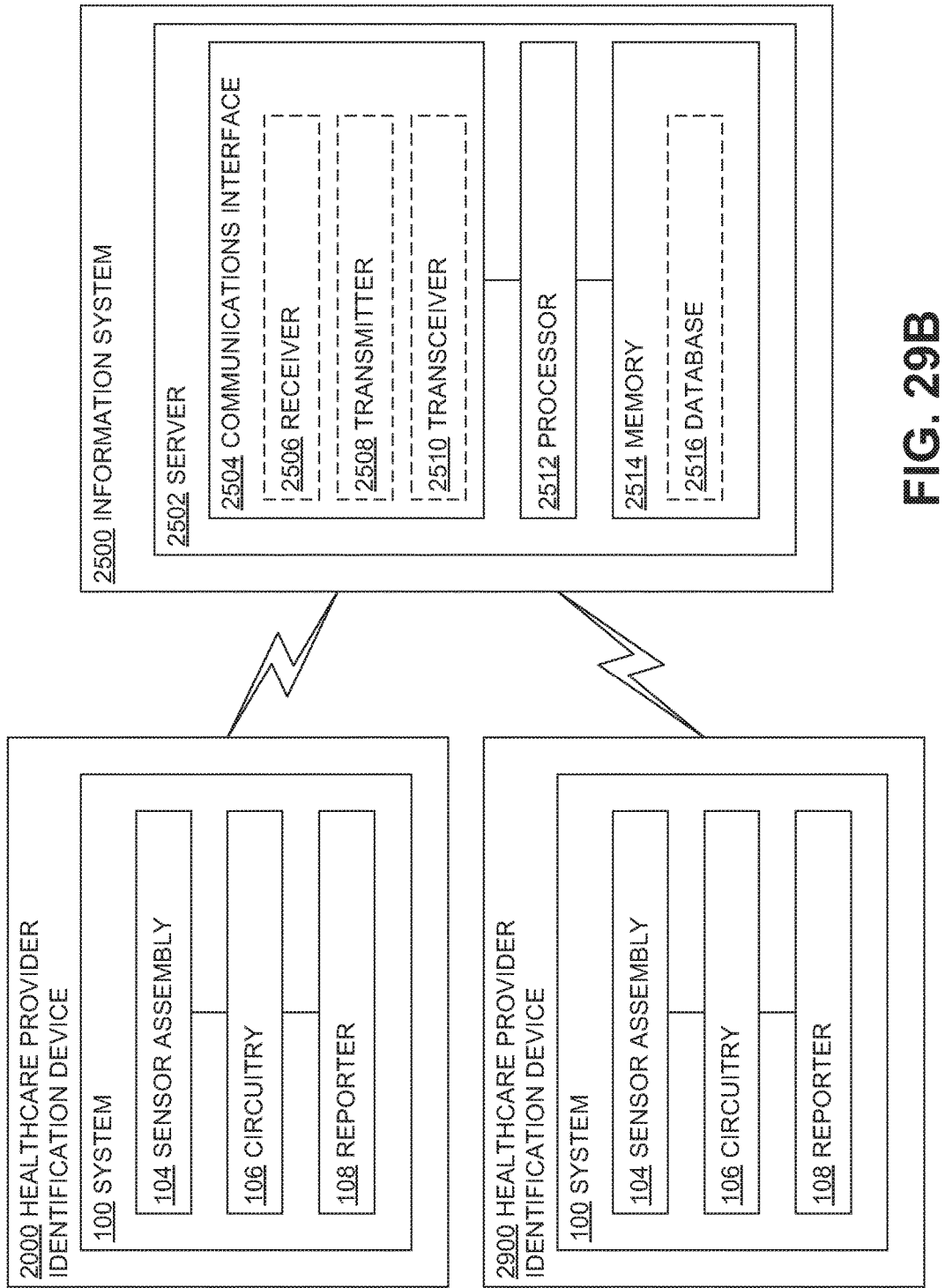
FIG. 29B is a schematic of an embodiment of an information system such as shown in FIG. 25 and a first healthcare provider identification device and a second healthcare provider identification device in communication with the information system.

In an embodiment, shown in FIG. 29B, healthcare provider identification device 2000 and healthcare provider identification device 2900 are configured to communicate with information system 2500. The information system 2500 can be configured to receive communication signals associated with identities of the individuals on whom healthcare provider identification device 2000 and healthcare provider identification device 2900 are placed, respectively. In an embodiment, the information system 2500 is configured to compare the communication signals with one or more authorization parameters and generate communication signals based on the comparison. For example, the information system 2500 can transmit one or more communication signals to healthcare provider identification device 2000 to alert the individual on whom the healthcare provider identification device 2000 is placed (e.g., an individual identified by healthcare provider identification device 200 as Dr. Bob) when the individual on whom the healthcare provider identification device 2900 is placed cannot be identified as an individual authorized to perform or participate in a health service action (e.g., individual on whom healthcare provider identification device 2900 is placed cannot be identified as Nurse Joe).

The reporter 108 can be configured to transmit one or more communication signals associated with an identity of the individual on whom the healthcare provider identification device 2000 is placed in a variety of scenarios. In an embodiment, the reporter 108 is configured to transmit the one or more communication signals to the information system 2500 to identify the healthcare provider to the information system 2500. For example, the reporter 108 can transmit one or more communication signals to log Dr. Bob into the information system 2500, whereby the information system 2500 grants Dr. Bob access based on one or more authorization parameters (e.g., permissions) corresponding to Dr. Bob. In an embodiment, the reporter 108 is configured to transmit the one or more communication signals to the information system 2500 to sign an information system entry for the healthcare provider. For example, the reporter 108 can transmit one or more communication signals to the information system 2500 to authenticate the entry as having been approved by an individual on whom the healthcare provider identification device 2000 is placed. In an embodiment, the reporter 108 is configured to transmit the one or more communication signals to the information system 2500 to sign an information system entry on demand from the healthcare provider or from an external device. For example, the reporter 108 can transmit one or more communication signals to the information system 2500 to authenticate the entry as having been approved by an individual on whom the healthcare provider identification device 2000 is placed in response to a user input (e.g., a user command) from the healthcare provider or a request from an external device (e.g., equipment the healthcare provider is accessing). In an embodiment, a healthcare provider or individual subject can initiate an interface (e.g., via reporter 108) with an external device or information system. For example, a doctor can initiate an interface (e.g., via reporter 108) with an external device or information system to sign electronic documents, or a doctor or patient can initiate an interface with an external device or information system to begin a session (e.g., a procedure, treatment, device operating session, etc.). In an embodiment, the reporter 108 is configured to transmit the one or more communication signals to the information system 2500 in response to a query from the information system 2500. For example, the information system 2500 can query the healthcare provider identification device 2000 to determine if the individual on whom the healthcare provider identification device 2000 is an authorized individual. In embodiments, the information system 2500 can query the healthcare provider identification device 2000 before authorizing a health service action, before providing access to information, or periodically (e.g., to make sure Dr. Bob is still the person on whom the healthcare provider identification device 2000 is placed). In an embodiment, the reporter 108 is configured to transmit one or more communication signals associated with at least one of identity sense signals or an identity of the healthcare provider to the information system 2500. In an embodiment, the reporter 108 is configured to transmit one or more communication signals associated with at least one of a date, a time, a location, or an activity state of the healthcare provider to the information system 2500.

The reporter 108 can be configured to transmit one or more communication signals associated with an identity of an individual being evaluated or cared for by a healthcare provider on whom the healthcare provider identification device 2000 is placed in a variety of scenarios. For example, as described herein and shown in FIGS. 22A and 22B, the healthcare provider identification device 2000 can be configured to evaluate one or more physical characteristics associated with an identity of an individual subject other than the healthcare provider on whom healthcare provider identification device 2000 is placed. In an embodiment, the reporter 108 is configured to transmit the one or more communication signals to the information system 2500 to identify an individual subject to the information system 2500. For example, the reporter 108 can transmit one or more communication signals that identify an individual to the information system 2500 as patient Greg, whereby the information system 2500 can associate data entries with patient Greg or provide access to information associated with patient Greg to the healthcare provider. In an embodiment, the reporter 108 is configured to transmit the one or more communication signals to the information system 2500 to validate an information system entry associated with the individual subject. For example, the reporter 108 can transmit one or more communication signals to the information system 2500 to authenticate the entry as corresponding to an individual being evaluated or cared for by the healthcare provider on whom the healthcare provider identification device 2000 is placed. In an embodiment, the reporter 108 is configured to transmit the one or more communication signals to the information system 2500 in response to a query from the information system 2500. For example, the information system 2500 can query the healthcare provider identification device 2000 to determine if the individual being evaluated by or cared for by the healthcare provider on whom the healthcare provider identification device 2000 is placed is an individual that the healthcare provider is authorized to perform a health service action with respect to (e.g., to make sure that Dr. Bob is evaluating or caring for an individual that can be identified as his patient, patient Greg). In embodiments, the information system 2500 can query the healthcare provider identification device 2000 before authorizing a health service action, before providing access to information, or periodically (e.g., to make sure Dr. Bob is with a patient that Dr. Bob is scheduled to see at a given time).

The healthcare provider identification device 2000 can also be configured to receive communication signals from the information system 2500. In an embodiment, the circuitry 106 is configured to receive (e.g., via receiver 404 or transceiver 406) one or more authorization parameters from the information system 2500. For example, the information system 2500 can program the healthcare provider identification device 2000 by providing authorization parameters for one or more individuals for whom the healthcare provider identification device 2000 is operable. For example, the healthcare provider identification device 2000 can be configured to receive authorization parameters associated with a list of individuals (e.g., Dr. Bob, Dr. Jan, and Nurse Joe) from the information system 2500. The circuitry 106 can be configured to store the one or more authorization parameters received from the information system 2500 in a memory (e.g., memory 402) of the system 100.

The healthcare provider identification device 2000 can be configured as a single-use device, a multiple-use device, a disposable device, a recyclable device, a reconfigurable device, or the like. In an embodiment, the healthcare provider identification device 2000 is configured as a single-use device. For example, the circuitry 106 can be configured to authorize a single health service action or provide a single comparison between reference data and identity sense signals associated with the individual on whom the deformable substrate 102 is placed. In an embodiment, an adhesive (e.g., adhesive 1300) for attaching the healthcare provider identification device 2000 to a skin surface of a body portion of a healthcare provider may be configured for a single-use application, whereby the adhesive is no longer capable of attaching the healthcare provider identification device 2000 to a skin surface after the healthcare provider identification device 2000 has been adhered to a skin surface and then removed. In an example, a healthcare provider may receive a new healthcare provider identification device 2000 before each procedure or other scheduled health service action. In an embodiment, the circuitry 106 is configured to authorize one or more health service actions for a single individual subject. For example, the circuitry 106 can be configured to authorize an individual identified as Dr. Bob to perform one or more procedures or other health service actions, but only with respect to patient Greg. In an example, a healthcare provider may receive a new healthcare provider identification device 2000 before seeing each patient. In an embodiment, the circuitry 106 is configured to authorize a plurality of health service actions. For example, the circuitry 106 can be configured to authorize an individual identified as Dr. Bob to perform several procedures or other health service actions. In an embodiment, the circuitry 106 is configured to authorize one or more health service actions for a predefined period of time. For example, the circuitry 106 can be configured to authorize an individual identified as Dr. Bob to perform one or more procedures or other health service actions within a predefined period of time (e.g., within 1 hour, 4 hours, 12 hours, 1 day, 1 week, etc.). In an example, a healthcare provider may receive a new healthcare provider identification device 2000 each day or before each shift (e.g., morning shift, afternoon shift, evening shift, night shift, overnight shift, etc.). In an embodiment, the circuitry 106 is configured to authorize one or more health service actions based upon a schedule. For example, the circuitry 106 can be configured with authorization parameters based upon a predetermined schedule for a healthcare provider on whom the healthcare provider identification device 2000 is to be placed. For example, the circuitry 106 can be configured with authorization parameters based upon a schedule of patients to be evaluated or cared for by Dr. Bob, a schedule of procedures Dr. Bob is scheduled to perform, or the like.

Figure 30A:
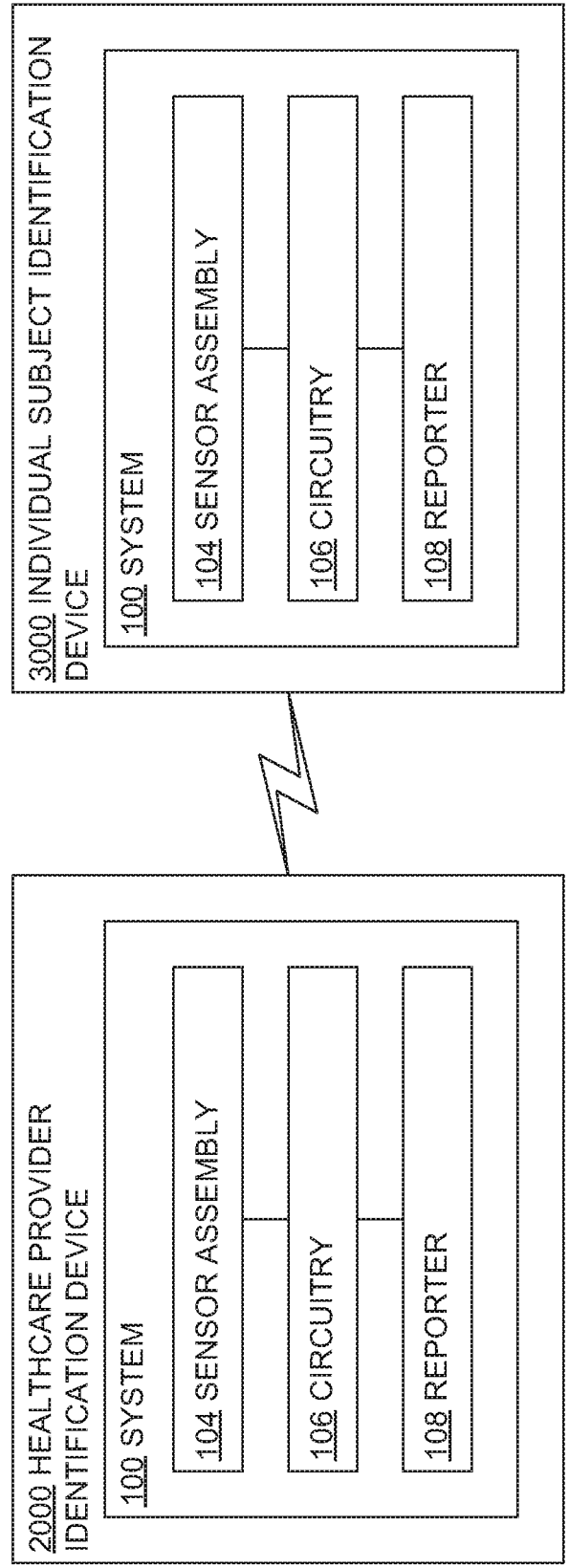
FIG. 30A is a schematic of an embodiment of a healthcare provider identification device such as shown in FIG. 20 and an individual subject identification device in communication with the healthcare provider identification device.

In an embodiment, shown in FIG. 30A, the healthcare provider identification device 2000 is configured to communicate with an individual subject identification device

3000. The individual subject identification device 3000 can have structure and functionality that is the same as or similar to healthcare provider identification device 2000. For example, the individual subject identification device 3000 can also include a system, such as the system 100 described herein to facilitate the identification of an individual subject (e.g., a patient or other individual) on whom the individual subject identification device 3000 is placed. In an embodiment, individual subject identification device 3000 is configured to generate (e.g., via reporter 108) one or more communication signals associated with an identity of an individual subject or associated with identity sense signals corresponding to one or more physical characteristics of the individual subject. The healthcare provider identification device 2000 can be configured to receive (e.g., via receiver 404 or transceiver 406 of circuitry 106) the one or more communication signals from individual subject identification device 3000. In an embodiment, the healthcare provider identification device 2000 can be configured to generate one or more communication signals (e.g., via reporter 108) corresponding to an authorization of the healthcare provider to perform or participate in a health service action with respect to the individual subject if the identity or identity sense signals generated by individual subject identification device 3000 are at least at a threshold correspondence with reference data (e.g., reference physical characteristics, authorization parameters, or the like). For example, when healthcare provider identification device 2000 is placed on an individual identified as Nurse Joe, Nurse Joe can be authorized to draw blood from an individual on whom the individual subject identification device 3000 is placed when healthcare provider identification device 2000 receives one or more communication signals from the individual subject identification device 3000 identifying the individual as patient Greg. The one or more communication signals can correspond to a lack of authorization of the healthcare provider to perform the health service action with respect to the individual subject responsive to a correspondence between the one or more identity sense signals generated by the individual subject identification device 3000 and the reference data indicative of one or more physical characteristics associated with the identity of the at least one second individual being below a threshold correspondence. For example, when the individual is not identified as patient Greg to the healthcare provider identification device 2000 by the individual subject identification device 3000, healthcare provider identification device 2000 can be configured to provide an alert (e.g., via reporter 108) to Nurse Joe (e.g., via display device 1200), or to an external device or system (e.g., to external device 2300 or information system 2500, or the like), e.g., disallowing the procedure to proceed (e.g., by inhibiting use of an instrument). In an embodiment, the alert can include one or more control signals that inhibit use of the external device 2300 or other equipment/instrument the healthcare provider is attempting to access. For example, when the individual is not identified as patient Greg to the healthcare provider identification device 2000 by the individual subject identification device 3000, healthcare provider identification device 2000 can be configured to provide a control signal (e.g., via reporter 108) to disable the external device 2300 or make it at least partially inaccessible to the healthcare provider. In an embodiment, the alert can include one or more communication signals that cause the information system 2500 to inhibit use of the external device 2300 or other equipment/instrument the healthcare provider is attempting to access. For example, when the individual is not identified as patient Greg to the healthcare provider identification device 2000 by the individual subject identification device 3000, healthcare provider identification device 2000 can be configured to provide a communication signal (e.g., via reporter 108) to information system 2500 that causes the information system 2500 to disable the external device 2300 or make it at least partially inaccessible to the healthcare provider.

Figure 30B:
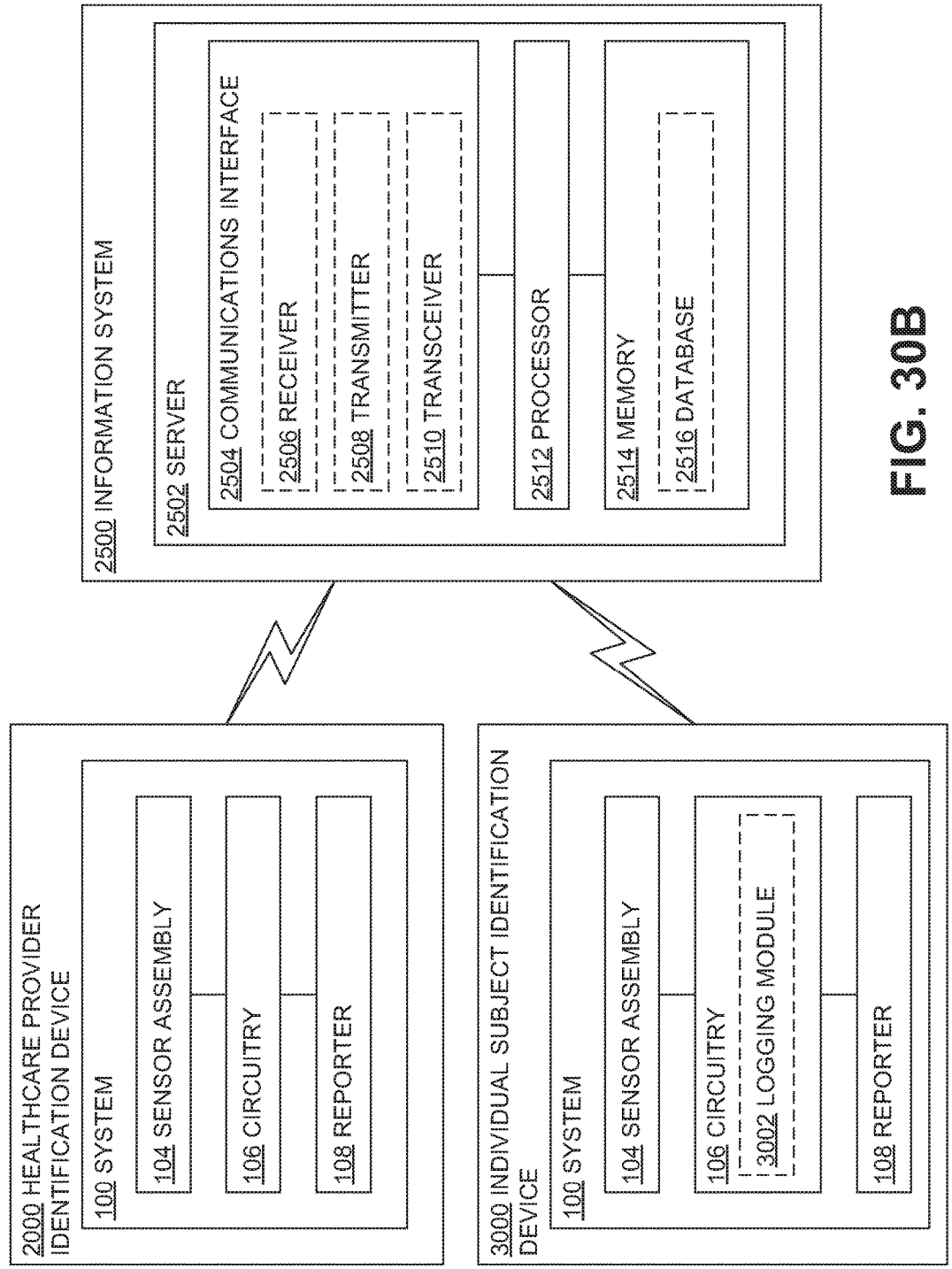
FIG. 30B is a schematic of an embodiment of an information system such as shown in FIG. 25 and a healthcare provider identification device and an individual subject identification device in communication with the information system.

In an embodiment, shown in FIG. 30B, healthcare provider identification device 2000 and individual subject identification device 3000 are configured to communicate with information system 2500. The information system 2500 can be configured to receive communication signals associated with identities of the individuals on whom healthcare provider identification device 2000 and individual subject identification device 3000 are placed, respectively. In an embodiment, the information system 2500 is configured to compare the communication signals with one or more authorization parameters and generate communication signals based on the comparison. For example, the information system 2500 can transmit one or more communication signals to healthcare provider identification device 2000 to alert a healthcare provider on whom the healthcare provider identification device 2000 is placed (e.g., an individual identified by healthcare provider identification device 200 as Dr. Bob) when the individual on whom the individual subject identification device 3000 is placed cannot be identified as an individual that the healthcare provider is authorized to perform a health service action for (e.g., individual on whom individual subject identification device 3000 is placed cannot be identified as patient Greg). In an embodiment, the information system 2500 can transmit an alert to an external device 2300 or other equipment/instrument, e.g., disallowing the procedure to proceed (e.g., by inhibiting use of the external device 2300). In an embodiment, the alert can include one or more control signals that inhibit use of the external device 2300 or other equipment/instrument the healthcare provider is attempting to access. For example, when the healthcare provider is not identified as Dr. Bob or the individual subject is not identified as patient Greg to the information system 2500, the information system 2500 can be configured to provide a control signal to external device 2300 to disable the external device 2300 or make it at least partially inaccessible to the healthcare provider. In another example, if patient Greg is scheduled to have a surgical procedure performed by Dr. Bob, the individual subject identification device 3000 identifies the individual on whom the individual subject identification device 3000 is placed to the information system 2500 as patient Greg, and the healthcare provider identification device 2000 identifies the individual on whom the healthcare provider identification device 2000 is placed to the information system 2500 as Dr. Bob, the information system 2500 can be configured to generate one or more communication signals associated with an authorization of the individual on whom the healthcare provider identification device 2000 is placed (i.e., Dr. Bob) to perform the surgical procedure for the individual on whom the individual subject identification device 3000 is placed (i.e., patient Greg).

In an embodiment, the individual subject identification device 3000 includes a system (or device), such as the system 100 described herein to facilitate the identification of the individual subject. As described herein and shown in FIG. 1, in an embodiment, the system 100 includes deformable substrate 102, sensor assembly 104, circuitry 106, and reporter 108. In an embodiment, the deformable substrate 102 is configured to conform to a contour of a body portion of an individual subject (e.g., the curvature of a limb). For example, as described herein, the deformable substrate 102 can comprise a deformable (e.g., conformable, flexible, stretchable, etc.) material configured to interface with, and conform to, the body portion. The body portion is shown in FIG. 1 as a hand, however the system 100 can be positioned on the skin surface of any body portion, including but not limited to, an arm, an elbow, a wrist, a hand, a finger, a leg, a knee, an ankle, a foot, a toe, a facial region, a neck region, a torso region, or the like. The deformable substrate 102 can be positioned in proximity with the skin surface according to various mechanisms including, but not limited to, affixed to the skin via an adhesive material, held in place by an external pressure, such as pressure provided by a material wrapped around or about a body portion (e.g., a fabric, a garment, a glove, a bandage, etc.), affixed in a textile, fabric, garment, accessory (e.g., a glove, a sock, a finger cot, etc.), or so forth.

As described herein, the sensor assembly 104 is coupled to the deformable substrate 102 and is positioned to generate one or more sense signals associated with a physical characteristic of the individual subject (e.g., a patient) on whom the system 100 is positioned. For example, as shown in FIG. 2, the sensor assembly 104 includes one or more identity sensors 200 configured to generate one or more identity sense signals associated with at least one physical characteristic of the individual subject. The identity sensor 200 can sense the physical characteristic to provide a basis for identification of the individual subject, or to provide an indication that the individual subject cannot be readily identified based on the observed physical characteristics. As described herein, the identity sensor 200 can include, but is not limited to, one or more of an optical sensor 202, an electromagnetic sensor 204, an impedance sensor 206, a capacitive sensor 208, an electrophysiological sensor 210, a plethysmographic sensor 212, a resistive sensor 214, a biosensor 216, or a chemical sensor 218. The identity sensor 200 can generate the one or more identity sense signals based on measurement or sensing of one more physical characteristics of the individual subject, where the one or physical characteristics can include, but are not limited to, skin topography features (e.g., pattern of skin surface, follicle pattern, pore pattern, pigmentation, etc.), vascular properties or layouts (e.g., arterial patterns, properties, or layouts; vein patterns, properties, or layouts; etc.), electric current pattern (e.g., photovoltaic current pattern), or skin resistivity measurement. For example, as shown in FIG. 3, the system 100 can be positioned on a skin surface of a body portion (shown as a top surface of a hand in FIG. 3), where the system 100 can detect via the identity sensor 200 one or more of a follicle pattern 300, a pore pattern 302, a skin pigmentation or distinctive skin mark 304, or a vascular pattern or layout 306. The identity sensor 200 can then generate one or more identity sense signals based on the structure of the particular sensor(s) of the sensor assembly 104 (e.g., optical sensor 202, electromagnetic sensor 204, impedance sensor 206, etc.), where such signals will correspond to the measured or sensed physical characteristics to facilitate in analysis of whether the identity of the individual subject can be determined.

As described herein, the sensor assembly 104 can be structured relative to the deformable substrate 102 such that at least a portion of the sensor assembly 104 is embedded within the deformable substrate 102, affixed to the deformable substrate 102, residing on the deformable substrate 102, printed directly onto the deformable substrate 102, or a combination thereof. For example, at least a portion of an identity sensor 200 can be embedded within the deformable substrate 102, can be affixed to the deformable substrate 102, can reside on the deformable substrate 102, can be directly printed on the deformable substrate 102, or a combination thereof. In an embodiment, the deformable substrate 102 can include one or more of a stretchable/flexible fabric, an elastomeric polymer, a hydrocolloid film, a membrane (e.g., a nanomembrane, such as a silicon nanomembrane), a gas-permeable elastomeric sheet, or other conformable material. In an embodiment, at least one of the sensor assembly 104, the circuitry 106, or the reporter 108 resides on the deformable substrate 102, such as residing on at least a portion of one or more of a stretchable/flexible fabric, an elastomeric polymer, a hydrocolloid film, a membrane (e.g., a nanomembrane, such as a silicon nanomembrane), a gas-permeable elastomeric sheet, or other conformable material. For example, at least a portion of at least one of the sensor assembly 104, the circuitry 106, or the reporter 108 can be printed directly onto at least a portion of the deformable substrate 102. In an embodiment, at least one of the sensor assembly 104, the circuitry 106, or the reporter 108 is embedded within the deformable substrate 102, such as embedded within at least a portion of one or more of a stretchable/flexible fabric, an elastomeric polymer, a hydrocolloid film, a membrane (e.g., a nanomembrane, such as a silicon nanomembrane), a gas-permeable elastomeric sheet, or other conformable material.

In an embodiment, the circuitry 106 is configured to receive one or more identity sense signals (e.g., from the sensor assembly 104) associated with one or more physical characteristics of the individual subject on which system 100 is positioned, and can provide analysis of the one or more identity sense signals. For example, in an embodiment, the circuitry 106 is operably coupled to the sensor assembly 104 such that the circuitry 106 is configured to receive the one or more identity sense signals from the one or more identity sensors 200 of the sensor assembly 104. In an embodiment, shown in FIG. 4, the circuitry 106 includes a comparison module 400 configured to compare the one or more identity sense signals generated by the sensor assembly 104 to reference data indicative of one or more physical characteristics associated with an identity of at least one individual to determine whether the one or more identity signals correspond to the identity of the at least one individual. In an embodiment, the reference data is stored in a computer memory device 402 which can include, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information maintained by the comparison module 400 and which can be accessed by the circuitry 106 or other associated accessing device.

As described herein, the circuitry 106 includes components to process the one or more sense signals from the sensor assembly 104 and to provide instruction to the reporter 108 to generate one or more communication signals associated with the one or more identity sense signals, a comparison of the one or more identity sense signals with the one or more physical characteristics from reference data indicative with an identity of a particular individual, determinations made by the circuitry 106, or other information. For example, the circuitry 106 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In an embodiment, the circuitry 106 includes one or more ASICs having a plurality of predefined logic components. In an embodiment, the circuitry 106 includes one or more FPGAs having a plurality of programmable logic commands. The computer memory device can be integrated with the system 100, can be associated with an external device and accessible by the system 100 through wireless or wired communication protocols, or a combination thereof. For example, the reference data can be stored by the computer memory 702 coupled to the deformable substrate 102 of the system 100, can be accessible by the circuitry 106 via wireless means, or can be available to the circuitry 106 through another method, such as through a remote network, a cloud network, and so forth. In an embodiment, the circuitry 106 includes a receiver 404 or transceiver 406 (e.g., antenna, etc.) to receive the reference data information or other information (e.g., correspondence threshold information, programming information) to facilitate operation or control of the system 100 through wireless or wired communication protocols. For example, the receiver 404 can receive one or more communication signals from an external device associated with but not limited to, control programming, authorization parameters, reference data, or a query (e.g., a query to transmit information from the system 100 to the external device, a query to begin sensing of identity sense signals via the sensor assembly 104, etc.). In embodiments, the circuitry 106 can also include a transmitter 408 or transceiver (e.g., antenna, etc.) to send information amongst components of the system 100 or to components external the system, such as to communicate with an external device or system (e.g., an external device or system described herein, including, but not limited to, external device 800, external device 2300, information system 2500, information system 2800, healthcare identification device 2000, guest device 3200, or a combination thereof). Such communication can include, for example, indications that the circuitry 106 is accessing one or more databases or memory devices storing reference or programming data, computational protocols, system updates, or the like.

The reference data includes data indicative of one or more physical characteristics associated with an identity of at least one individual. For example, the reference data can include, but is not limited to, a skin topography feature associated with an identity of an individual, a skin surface pattern associated with an identity of an individual, a follicle pattern associated with an identity of an individual, a pore pattern associated with an identity of an individual, a pigmentation pattern or characteristic associated with an identity of an individual, a vascular layout associated with an identity of an individual, an electric current pattern associated with an identity of an individual, a photovoltaic current pattern associated with an identity of an individual, a skin resistivity measurement associated with an identity of an individual, or the like. For example, the reference data can include one or more physical characteristics associated with a first person/individual, one or more physical characteristics associated with a second person/individual, one or more physical characteristics associated with a third person/individual, and so on. The circuitry 106 is configured to compare the identity sense signals from the sensor assembly 104 to the reference data, such that when the comparison is at or exceeds a threshold correspondence (e.g., within a predetermined confidence interval), the identity of the person/individual stored by the reference data can be attributed to the individual on which the system 100 is positioned. For example, if the reference data includes physical characteristic information for each of patients Greg, Joe, and Lisa, the circuitry 106 can compare the identity sense signals from the sensor assembly 104 to determine whether the identity sense signals would correspond to the physical characteristic information of Greg, Joe, or Lisa.

As described herein, the reporter 108 of the system 100 is configured to generate one or more communication signals to report information associated with operation of the system 100. In an embodiment, the reporter 108 is operably coupled to the circuitry 106 and is configured to generate one or more communication signals responsive to instruction by the circuitry 106. The communication signals can be associated with the one or more identity sense signals generated by the sensor assembly 104 (e.g., via the one or more identity sensors 200), with a comparison of the one or more identity sense signals with the one or more physical characteristics associated with the identity of the at least one individual (e.g., as provided by the circuitry 106 to determine whether the one or more identity signals correspond to the identity of the at least one individual), or a combination thereof. For example, the reporter 108 can report that the individual on which the system 100 is placed corresponds to a first individual (e.g., it is patient Greg), the reporter 108 can report that the information transmitted is a second individual's physical characteristics (e.g., this information corresponds to the skin topography feature of patient Joe), the reporter 108 can report that the system 100 is unable to determine an identity of the individual (e.g., the physical characteristics measured by the sensor assembly 104 do not correspond to, or do not meet a threshold correspondence to, any of Greg, Joe, or Lisa), or the like.

In embodiments, the reporter 108 is configured to report the one or more communications signals to identify the individual subject for authorization by an external device or system, to request authorization from an external device or system for the individual subject to perform an action, receive a treatment, operate an external device, or the like (e.g., based on identity, identity sense signals, or an associated comparison), or at least partially authorizing the individual subject to perform an action, receive a treatment, operate an external device, or the like. For example, the reporter 108 can report one or more communications signals identifying patient Greg to an external device or system, requesting authorization from the external device or system for patient Greg to perform an action, receive a treatment, operate an external device, or the like, or at least partially authorizing patient Greg to perform an action, receive a treatment, operate an external device, or the like.

In an embodiment, the communication signals are reportable to an external device or system (e.g., an external device or system described herein, including, but not limited to, external device 800, external device 2300, information system 2500, information system 2800, healthcare identification device 2000, guest device 3200, or a combination thereof). For example the external device or system can include, but is not limited to, a computing device, system or network (e.g., a personal computing device, a server, electronic health records system, a billing system, a scheduling system, an inventory management system, a claim processing system, an administrative system, etc.), or an electronic device (e.g., an electronic controller such as on a medical device, surgical device, a therapeutic device, an assistive device, an imaging device, a rehabilitative device, a drug delivery tool, vending machine, display device, or other electronic equipment). In an embodiment, the system 100 can transmit the one or more communication signals to a computing device having at least one of circuitry or programming that collects data from one or more wearable sensors that are part of the system 100 or are otherwise associated with the individual on which the system 100 is positioned, so that the computing device can associate data within the communication signals with the individual. The system 100, via the reporter 108, can transmit identity information to an electronic controller equipped with authorization capabilities for employment in authorizing use of one or more devices, programs, device functionalities, or the like, by the identified individual. For example, the system 100 can transmit information that the individual is identified as patient Greg, whereby the electronic controller can facilitate use of one or more devices, programs, device functionalities by patient Greg, according to his identity.

In an embodiment, shown in FIG. 7, the reporter 108 includes one or more of a transmitter 700, a transceiver 702, or a receiver 704. For example, as described herein, the reporter 108 can include an antenna structure configured to at least one of transmit the one or more communication signals (e.g., via the transmitter 700, the transceiver 702, etc.) or receive one or more communication signals from an external device (e.g., via the transceiver 702, the receiver 704, etc.). The one or more communication signals from the external device can include but are not limited to, control programming, authorization parameters, reference data, or a query (e.g., a query to transmit information from the system 100 to the external device). In an embodiment, the sensor assembly 104 includes one or more of a transceiver (e.g., transceiver 702) or a receiver (e.g., receiver 704) configured receive one or more communication signals from an external device. For example, the one or more communication signals from the external device can include but are not limited to, control programming, authorization parameters, reference data, or a query (e.g., a query for one or more communication signals associated with an identity or identity sense signals, or a query to begin sensing physical characteristics of the individual subject on which the system 100 is positioned).

Figure 31A:
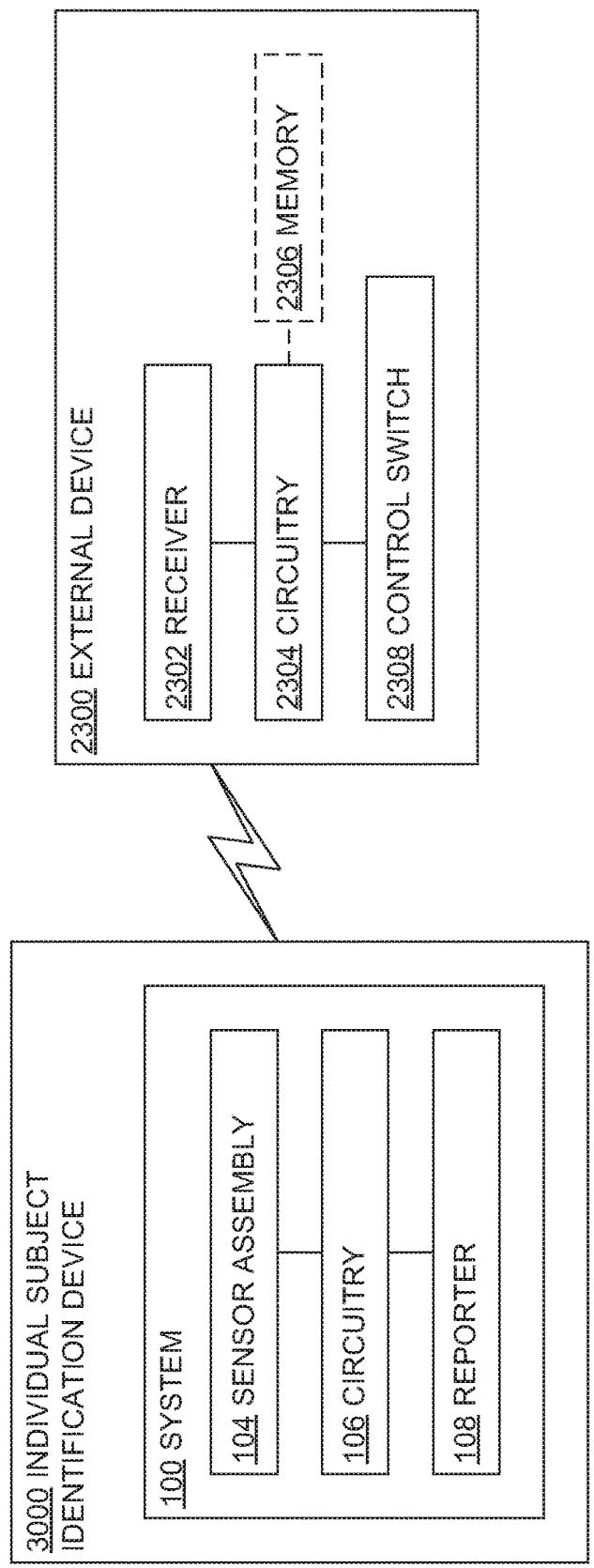
FIG. 31A is a schematic of an embodiment of an individual subject identification device such as shown in FIG. 30A and an external device in communication with the individual subject identification device.

As shown in FIG. 31A, the individual subject identification device 3000 can be configured to communicate with external device 2300. As described herein, the external device 2300 is configured to receive communications from the reporter 108 for analysis by the external device 2300. The external device 2300 can include a receiver 2302 (e.g., receiving antenna, transceiver, etc.) configured to receive the one or more communication signals from the reporter 108. The external device 2300 can also include circuitry 2304 configured to compare the one or more communication signals with one or more authorization parameters associated with one or more users authorized to operate the external device 2300. For example, the external device 2300 can include, or can access, a computer memory device 2306 that maintains data associated with authorization parameters pertinent to operation of the external device 2300. In an embodiment, the one or more authorization parameters include at least one scheduled parameter. The scheduled parameter can be associated with a treatment schedule, a recovery schedule, a rehabilitation schedule, a pre-operative schedule, a post-operative schedule, a discharge schedule, any combination thereof, and so forth. For example, a scheduled parameter can include, but is not limited to, a list of identities of one or more individuals scheduled to undergo a procedure, a list of identities of one or more individuals scheduled to receive a treatment, a list of identities of one or more individuals scheduled to operate an external device, a list of identities of one or more individuals with pre-operative permissions or restrictions, a list of identities of one or more individuals with post-operative permissions or restrictions, a list of identities of one or more individuals with pre-treatment permissions or restrictions, a list of identities of one or more individuals with post-treatment permissions or restrictions, or a combination thereof. In an embodiment, two or more scheduled parameters can affect authorization. For example, an individual identified as patient Greg can be two days post-operation but may also be scheduled for a treatment (e.g., chemotherapy treatment) and can thus have restrictions associated with the treatment that override Greg's post-operative permissions (e.g., post-operation patients are allowed to go outside, pre-chemotherapy patients are not—based on a comparison with the authorization parameters Greg is not allowed to exit through an automatic door). In an embodiment, the one or more authorization parameters can include a list of reference physical characteristics for one or more individuals authorized to operate an external device. For example, if patients without peanut allergies are allowed to operate a vending machine, an individual identified as Greg will not be allowed to operate the vending machine if Greg has a peanut allergy. In an embodiment, the one or more authorization parameters can include scheduled parameters that are affected by time (e.g., different permissions/restrictions after hour 1, hour 2, hour 3, . . . , day 1, day 2, day 3, . . . , week 1, week 2, week 3, and so on). For example, if an individual identified as Greg is one day post-operation, the individual may be authorized to operate a walker device, and when an individual identified as Greg is three days post-operation, the individual may be authorized to operate a crutch or cane device but no longer authorized to operate the walker device. In an embodiment, the external device 2300 can receive the communication signals from the reporter 108 indicating an identity of the individual subject on whom the deformable substrate 102 is positioned, whereby the external device 2300 can compare (e.g., via the circuitry 2304) the identity of the individual with the authorization parameters stored in the memory 2306 to determine whether the identified individual is authorized to operate the external device 2300, to determine which functionalities of the external device 2300 the identified individual is authorized to operate, or the like. In an embodiment where the authorization parameters includes a list of identified devices or systems, such devices or systems can automatically operate the portion of features of the external device 2300, such as without interaction with the individual subject. In an embodiment, the external device 2300 includes a control switch 2308 for turning at least a portion of the external device 2300 on or off, or partially enabling or disabling one or more functionalities of the external device 2300 based on a comparison of the identity or identity sense signals with one or more authorization parameters, or based on whether or not the individual on whom the deformable substrate 102 is positioned is identified to the external device 2300 as having authorization to operate the external device 2300.

As described herein and shown in FIG. 10, in an embodiment, the circuitry 106 can include an identity comparison module 1000 and an authorization comparison module 1002. The identity comparison module 1000 is configured to compare the one or more identity sense signals generated by the sensor assembly 104 to reference data indicative of one or more physical characteristics associated with an identity of at least one individual to determine whether the one or more identity sense signals correspond to the identity of the at least one individual. For example, the identity comparison module 1000 can include structure and functionality similar to, or the same as, the comparison module 400 described herein. The reference data indicative of one or more physical characteristics associated with an identity of at least one individual can be stored in a computer memory device 1004 accessible by the circuitry 106, the identity comparison module 1000, or the authorization comparison module 1002. For example, the computer memory device 1004 can store data associated with a list of identities (e.g., names of individuals) having associated physical characteristics attributable to the particular identity (e.g., a skin topography feature associated with and unique to a first identity, a skin topography feature associated with and unique to a second identity, and the so forth). The authorization comparison module 1002 is configured to compare at least one of the one or more identity sense signals or the identity of the at least one individual with one or more authorization parameters. In an embodiment, the authorization comparison module 1002 is configured to compare at least one of one or more identity sense signals associated with an individual subject on which the system 100 is placed or the identity of the individual subject with one or more authorization parameters. In an embodiment, the one or more authorization parameters include at least one scheduled parameter. The scheduled parameter can be associated with a treatment schedule, a recovery schedule, a rehabilitation schedule, a pre-operative schedule, a post-operative schedule, a discharge schedule, any combination thereof, and so forth. For example, a scheduled parameter can include, but is not limited to, a list of identities of one or more individuals scheduled to undergo a procedure, a list of identities of one or more individuals scheduled to receive a treatment, a list of identities of one or more individuals scheduled to operate an external device, a list of identities of one or more individuals with pre-operative permissions or restrictions, a list of identities of one or more individuals with post-operative permissions or restrictions, a list of identities of one or more individuals with pre-treatment permissions or restrictions, a list of identities of one or more individuals with post-treatment permissions or restrictions, or a combination thereof.

In an embodiment, the reporter 108 is configured to generate the one or more communication signals responsive to instruction by the circuitry 106, where the one or more communication signals are associated with a comparison of at least one of the one or more identity sense signals with the one or more authorization parameters or the identity of the at least one individual with the one or more authorization parameters. For example, instances where the one or more communication signals are based on a comparison of one or more identity sense signals with the one or more authorization parameters, the authorization comparison module 1002 can directly compare the one or more identity sense signals with authorization parameters stored in the memory 1004. The authorization parameters can include a list of physical characteristics of authorized individuals, such that when the identity sense signals match the physical characteristics of authorized individuals stored in memory, the individual subject can be authorized. For example, authorization can include, but is not limited to, the individual being authorized to utilize the system 100 or to use an external device (e.g., where the individual subject substantially matches one identity of the list of individuals authorized to operate the external device), or the system 100 can function fully (e.g., can transmit information) or a portion of the functionalities of the system 100 to which the authorized individual is permitted to utilized are enabled. When the one or more communication signals are based on a comparison of the identity of the at least one individual with the one or more authorization parameters, the identity comparison module 1000 can first identify the individual based on the one or more identity sense signals, whereby the authorization comparison module 1002 can determine whether the identified authorized individual is (e.g., by comparing the identity to reference data having a list of authorized individuals or identities). In an embodiment, when the one or more authorization parameters corresponds to a single authorized user, the identity comparison module 1000 and the authorization comparison module 1002 can be incorporated as a single module for automatic authentication after identification.

In an embodiment, shown in FIG. 11, the circuitry 106 includes a comparison module 1100 configured to compare the one or more identity sense signals generated by the sensor assembly 104 to reference data indicative of one or more physical characteristics associated with a physical state of the individual to determine whether the individual subject is authorized to operate an external device. For example, the memory 1004 can store reference data associated with physical states including but not limited to, a vital status (e.g., physiological reference data indicative of a living status or a deceased status, physiological data associated with a distress or stress status, or the like) or a functional status (e.g., a physical status, a mental status, or the like). In an embodiment, the comparison module compares sense signals from other sensors of the system (e.g., one or more of the physiological sensor 900, the proximity sensor 902, the contact sensor 904, the pressure sensor 906, or the temperature sensor 908) to determine the vital status or the functional status of the individual. The reference data indicative of one or more physical characteristics associated with a functional status can include but are not limited to, chemical or biological indicators of inebriation or intoxication (e.g., by drugs or alcohol), the presence or absence of a substance (e.g., a toxin, a poison, a prescription medication), a blood oxygenation level, a movement, pattern of movement, or absence of movement (e.g., as indicators of a state of consciousness or of compromised fine motor skills), or so forth. The vital status or the functional status can serve as an indicator as to whether an identified individual is in a state suitable for operation of the external device. While the individual subject may be identified and authorized to use an external device (e.g., external device 2300), the current status of the individual may preclude total or partial operation of the external device. For example, the sensors of the system 100 may detect that the individual subject has an elevated blood pressure making it unsafe for the individual subject to consume coffee, where the individual subject is otherwise authorized to receive coffee from a vending machine (e.g., patient Greg is on a list of individuals authorized to have caffeine and hot liquids). In another example, the individual subject may be authorized to operate a walker device, but the sensors of the system 100 may detect that the individual subject is experiencing orthostatic hypotension (low blood pressure upon standing), making it unsafe for the individual subject to walk at that particular time, so authorization for use is prevented. In an embodiment, the system 100 is configured to determine a status of the individual subject based on a schedule parameter (e.g., schedule of procedures), logged activity state of the individual subject (e.g., logged procedures, logged food, fluid, or drug consumption, logged mobility or operation of external devices, etc., which may be stored by logging module 3002), timing information (e.g., check in time, sleep/rest time, activity time, etc.), or the like. For example, the system 100 can determine that the patient been X-rayed in the past two hours, and accordingly, prevent authorization of further X-ray treatments until two hours have passed. In another example, a logged activity state of the patient can include how many treatments or treatment exposures the patient has had (e.g., X-ray treatments, total radiation exposures, total rads for the patient, etc.), where the system 100 can authorize or prevent authorization of another treatment, patient activity, patient consumption, patient visits, etc., based on the number of X-ray treatments or total radiation exposures (e.g., the patient has received two treatments (e.g., radiation treatments) in 24 hours, so she cannot have a third treatment until 12 hours have passed). In another example, the system 100 can determine that the patient is allowed to use equipment based on whether or not the patient used the equipment in the last 24 hours, the settings on the equipment when last used by the patient, and so forth. In another example, a logged activity state of the patient can include information that the patient was prepped for procedure at 08:00, so the patient needs to have the procedure by 10:00; after 10:00 the system 100 may determine that the healthcare provider is no longer authorized to initiate the procedure. In an embodiment, the circuitry 106 is configured to prevent authorization of the individual subject to operate at least a portion of the external device responsive to a correspondence between the one or more identity sense signals and the reference data indicative of the one or more physical characteristics associated with the functional status of the individual being above a functional threshold correspondence. For example, the functional threshold correspondence can be related to a safety threshold of a physical characteristic for operation of the external device (e.g., a blood alcohol content, a medication level, etc.). In an embodiment, the circuitry 106 prevents authorization of the individual subject by not instructing the reporter 108 to generate or transmit the one or more communication signals. In an embodiment, the circuitry 106 can permit partial authorization of operation of the external device, such that only a subset of functionalities of the external device is available to the individual subject for operation. For example, if an individual subject is identified and authorized to use a smartphone, and the individual subject is determined to have a diminished functional status as a result of one or more medications, the circuitry 106 can authorize the individual to use internet browsing functionalities but prevent messaging functionalities.

As described herein and shown in FIG. 12, in an embodiment, the reporter 108 includes a display device 1200 configured to provide a visual indication associated with an output of the reporter 108. For example, the display device 1200 can include one or more light-emitting elements 1202 (e.g., light-emitting diodes, polymer light-emitting diodes (PLEDs), lasers, or other light source(s)) configured to provide a predetermined pattern of light corresponding to a comparison between at least one of the one or more identity sense signals with the one or more authorization parameters or the identity of the at least one individual with the one or more authorization parameters. The predetermined pattern of light can include patterns associated with light intensity or brightness, color, shapes, or other characteristics discernable between distinct patterns. In an embodiment, the predetermined pattern includes a first pattern associated with a correspondence between at least one of the one or more identity sense signals with the one or more authorization parameters or the identity of the at least one individual with the one or more authorization parameters being below a threshold correspondence (e.g., the physical characteristics measured by the sensor assembly 104 do not correspond to an authorized individual), and the predetermined pattern includes a second pattern associated with a correspondence between at least one of the one or more identity sense signals with the one or more authorization parameters or the identity of the at least one individual with the one or more authorization parameters being at least at the threshold correspondence (e.g., the physical characteristics measured by the sensor assembly 104 correspond to an authorized individual). For example, the reporter 108 can display via the display device a first pattern (e.g., a first intensity, a first color, a first shape, etc.) if the individual subject is not authorized to operate an external device, and can display a distinct second pattern (a second intensity, a second color, a second shape, etc.) if the individual subject is authorized to operate an external device. The system 100 can also include one or more photodetectors, such as one or more organic photodetectors (OPDs), to detect light from the display device 1200 and/or the sensor assembly 104, such as light reflected by or refracted from a body portion. For example, the system 100 can include an organic photodetector comprising an active layer of poly(3-hexylthiophene) (P3HT): (6,6)-phenyl-C61-butyric acid methyl ester (PCBM). In an embodiment, the display device 1200 includes one or more sound-emitting elements 1204 (e.g., speaker, tone-source, or other sound source(s)) configured to provide a predetermined pattern of sound corresponding to a comparison between at least one of the one or more identity sense signals with the one or more authorization parameters or the identity of the at least one individual with the one or more authorization parameters. The predetermined pattern of sound can include patterns associated with sound intensity, audible and inaudible phases, or other characteristics discernable between distinct patterns. In an embodiment, the predetermined pattern includes a first pattern associated with a correspondence between at least one of the one or more identity sense signals with the one or more authorization parameters or the identity of the at least one individual with the one or more authorization parameters being below a threshold correspondence (e.g., the physical characteristics measured by the sensor assembly 104 do not correspond to an authorized individual), and the predetermined pattern includes a second pattern associated with a correspondence between at least one of the one or more identity sense signals with the one or more authorization parameters or the identity of the at least one individual with the one or more authorization parameters being at least at the threshold correspondence (e.g., the physical characteristics measured by the sensor assembly 104 correspond to an authorized individual). For example, the reporter 108 can display via the display device a first pattern (e.g., a first intensity, a first audible/inaudible pattern, etc.) if the individual subject is not authorized to operate an external device, and can display a distinct second pattern (a second intensity, a second audible/inaudible pattern, etc.) if the individual subject is authorized to operate an external device.

In an embodiment, the display device 1200 includes a projection display 1206 configured to provide a visual indication associated with an output of the reporter 108. For example, the projection display 1206 can be configured to provide a projected image (e.g., projected onto a skin surface, onto a clothing item or garment, onto a wall or support surface, onto a screen, drape, etc.) corresponding to a comparison between at least one of the one or more identity sense signals with the one or more authorization parameters or the identity of the at least one individual with the one or more authorization parameters.

In an embodiment, the circuitry 106 is configured to determine whether the deformable substrate 102 has been removed from the skin surface of the individual subject. For example, the system 100 can include, as a part of the sensor assembly 104, distinct from the sensor assembly 104, or a combination thereof, one or more of a strain gauge or a proximity sensor configured to sense whether the deformable substrate 102 has been removed from the skin surface of the individual subject. For example, the system 100 can include a computer memory device storing reference data associated with strain or distance measurements corresponding to removal of the deformable substrate 102 from a skin surface. The circuitry 106 can compare the output from the strain gauge or proximity sensor to such reference data to determine whether the deformable substrate 102 has been removed. In an embodiment, the circuitry 106 is configured to determine whether the deformable substrate 102 has been applied to a skin surface that differs from the skin surface of the individual subject. For example, the system 100 can store in a computer memory device the one or more identity sense signals obtained by the sensor assembly 104 at a first time, whereby the circuitry 106 can compare one or more identity sense signals obtained by the sensor assembly 104 at a second time to the stored identity sense signals obtained by the sensor assembly 104 at the first time to determine whether the signals substantially differ. If the signals are directed to a skin property, a substantial difference between signals obtained at differing times can indicate that the skin surface differs between the first time and the second, which can indicate that the system 100 was transferred between different individuals between the first time and the second time.

The reporter 108 can generate the one or more communication signals responsive to a variety of scenarios involving one or more of identification or authorization. For example, in an embodiment, the one or more communication signals generated by the reporter 108 correspond to a lack of authorization of the individual subject to operate an external device responsive to a correspondence between the one or more identity sense signals and the reference data indicative of one or more physical characteristics associated with the identity of the at least one individual being below a threshold correspondence. For example, when the circuitry 106 (e.g., via the identity comparison module 1000) is unable to identify the individual subject on which the system 100 is positioned, the reporter 108 can report via the communication signals that the individual subject is not authorized to operate the external device on the basis that such individual is not recognizable. In an embodiment, when the circuitry 106 (e.g., via the identity comparison module 1000) is unable to identify the individual subject on which the system 100 is positioned, the circuitry 106 prevents generation of the communication signals by the reporter 108 (e.g., no instruction from the circuitry 106 to the reporter 108 regarding generation of the one or more communication signals). In an embodiment, the one or more communication signals generated by the reporter 108 correspond to authorization of the individual subject to operate an external device responsive to both of (i) a correspondence between the one or more identity sense signals and the reference data indicative of one or more physical characteristics associated with the identity of the at least one individual being at least at a threshold correspondence and (ii) a correspondence between at least one of the one or more identity sense signals or the identity of the at least one individual with one or more authorization parameters being at least at a threshold correspondence. For example, when the circuitry 106 is able to identify the individual subject on which the system 100 is positioned (e.g., via the identity comparison module 1000) and the circuitry 106 is able to authorize the individual subject on which the system 100 is positioned (e.g., via the authorization comparison module 1002), the reporter 108 can report via the communication signals that the individual subject is authorized to operate an external device, or participate in any other activity requiring authorization of the individual subject.

In an embodiment, the reporter 108 is configured to provide a static output of communication signals. In an embodiment, the reporter 108 is configured to continuously generate the one or more communication signals. In an embodiment, the reporter 108 is configured to provide a dynamic output of communication signals. In an embodiment, the reporter 108 is configured to generate the one or more communication signals responsive to a query from an external device or system (e.g., an external device or system described herein, including, but not limited to, external device 800, external device 2300, information system 2500, information system 2800, healthcare identification device 2000, guest device 3200, or a combination thereof). In an embodiment, the reporter 108 is configured to generate the one or more communication signals responsive to a proximity between the reporter 108 and an external device or system (e.g., an external device or system described herein, including, but not limited to, external device 800, external device 2300, information system 2500, information system 2800, healthcare identification device 2000, guest device 3200, or a combination thereof). For example, the system 100 can include a proximity sensor (e.g., proximity sensor 902) configured to generate sense signals indicative of proximity between the reporter 108 and an external device or system (e.g., an external device or system described herein, including, but not limited to, external device 800, external device 2300, information system 2500, information system 2800, healthcare identification device 2000, guest device 3200, or a combination thereof). The circuitry 106 can compare the sense signals from the proximity sensor to reference data (e.g., a threshold proximity) to determine whether the reporter 108 and the external device or system are close enough to begin transmission of communication signals from the reporter 108 to the external device or system, and instruct the reporter 108 to generate the one or more communication signals when it is determined that the reporter 108 and the external device or system are within a threshold proximity.

As described herein and shown in FIG. 30B, the individual subject identification device 3000 can be configured to communicate with information system 2500. The information system 2500 can be configured to receive (e.g., via communications interface 2504) one or more communication signals from the reporter 108. The information system 2500 can also include circuitry (e.g., processor 2512) configured to compare the one or more communication signals with one or more authorization parameters. For example, the database 2516 can maintain data associated with authorization parameters pertinent to operation of external devices, accessing information (e.g., patient health records, billing information, inventory data, etc.), and so forth. In an embodiment, the information system 2500 can receive the communication signals from the reporter 108 indicating an identity of the individual subject on whom the deformable substrate 102 is positioned, whereby the information system 2500 can compare (e.g., via processor 2512) the identity with authorization parameters stored in the memory 2514 to determine whether the individual subject is authorized to receive a treatment, operate an external device, or access information via the information system 2500, or perform any other activity requiring authorization of the individual subject.

In an embodiment, the information system 2500 can generate (e.g., via communications interface 2504) one or more communication signals associated with whether the individual subject is authorized to receive a treatment, operate an external device, or access information via the information system 2500, or perform any other activity requiring authorization of the healthcare provider. For example, the information system 2500 can transmit (e.g., via communications interface 2504) one or more communication signals to the individual subject identification device 3000 or to an external device or system (e.g., external device 800, external device 2300, healthcare provider identification device 2000, a second information system 2800, or the like). In an embodiment, the information system 2500 can transmit (e.g., via communications interface 2504) the one or more authorization parameters to the individual subject identification device 3000 or to an external device or system (e.g., external device 800, external device 2300, healthcare provider identification device 2000, or a second information system 2800, or the like), whereby the device or system receiving the one or more authorization parameters can perform a comparison between the one or more authorization parameters and the identity or identity sense signals associated with the individual subject on which the system 100 is placed.

In an embodiment, the circuitry 106 of the system 100 includes a logging module 3002 configured to store at least one activity state of the individual subject in a memory device of the system 100 (e.g., in memory 402 or memory 1004 described herein, or the like). For example, the logging module 3002 can be configured to store at least one activity state of the individual subject including information corresponding to receiving a treatment, operating an external device, a location, a time, a date, any combination of thereof, and so forth. In embodiments, the logging module 3002 can be configured to store at least one activity state of the individual subject including, but not limited to, information corresponding to a procedure performed upon the individual subject, information corresponding to an external device operated by the individual subject, information corresponding to supplies (e.g., medical supplies) exhausted by the individual subject, information corresponding to food or beverage consumption by the individual subject, information corresponding to a treatment received by the individual subject, information corresponding to an activity (e.g., sleeping, walking, watching TV, etc.), information corresponding to medication dosage, timing, etc., information corresponding to a healthcare provider having performed a service for the individual subject, or any combination thereof. In an embodiment, the reporter 108 is configured to generate one or more communication signals associated with a logged activity state of the individual subject. The reporter 108 can be configured to communicate one or more communication signals associated with a logged activity state of the healthcare provider to the information system 2500. For example, the reporter 108 can transmit one or more communication signals to the information system 2500 indicating that an individual identified as patient Greg underwent a scheduled surgical procedure. Responsive to the information system 2500 indicating that an individual identified as patient Greg underwent a scheduled surgical procedure, the information system 2500 can update one or more database entries (e.g., updates to billing information to account for the procedure, updates to inventory information (e.g., updates based on supplies exhausted for the procedure), updates to patient information (e.g., updates to electronic health records) for the individual subject, updates to scheduling information (e.g., generating a post-operative schedule) for the individual subject, and the like).

Figure 31B:
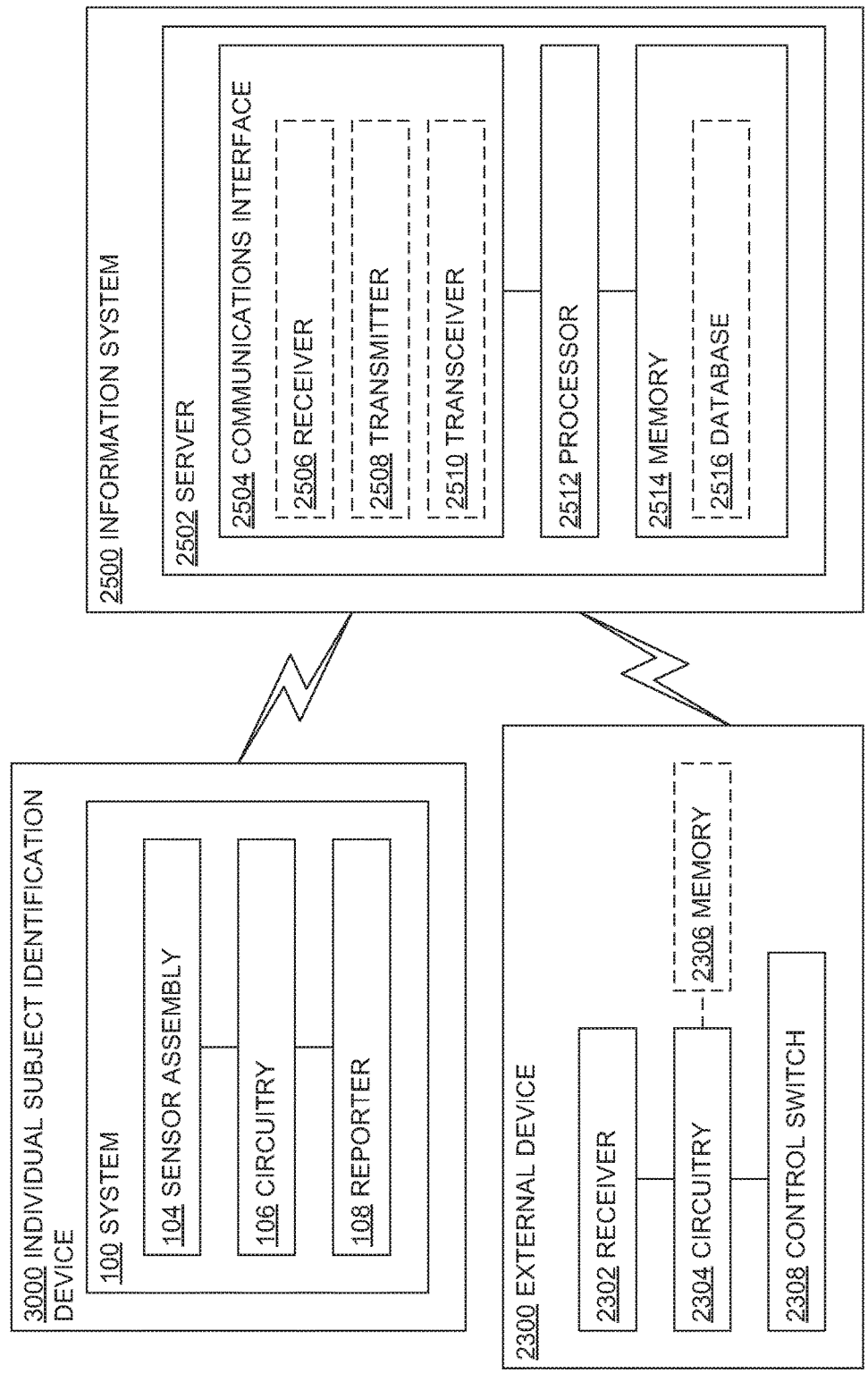
FIG. 31B is a schematic of an embodiment of an information system such as shown in FIG. 25 and an individual subject identification device and an external device in communication with the information system.

As shown in FIG. 31B, the information system 2500 can be in communication with the individual subject identification device 3000 and the external device 2300. In an embodiment, the information system 2500 is configured to facilitate a network connection between the individual subject identification device 3000 and the external device 2300. In an embodiment, the information system 2500 is configured to provide one or more communication signals for controlling functionality of the external device 2300 based on the one or more communication signals received from the individual subject identification device 3000. For example, the individual subject identification device 3000 can transmit one or more communication signals associated with an identity or identity sense signals of the individual subject to the information system 2500, whereby the information system 2500 can perform a comparison with one or more authorization parameters. The information system 2500 can send one or more communication signals to the external device 2300 that enable the individual subject to fully or partially operate the external device 2300 based on the comparison. For example, the information system 2500 can send one or more communication signals that place the external device 2300 into an operational mode based on receiving one or more communication signals from the individual subject identification device 3000 indicating that an individual on which the individual subject identification device 3000 is placed can be identified as patient Greg, where a list of individuals authorized to operate the external device 2300 includes Greg.

The reporter 108 can be configured to transmit one or more communication signals associated with an identity of the individual on whom the individual subject identification device 3000 is placed in a variety of scenarios. In an embodiment, the reporter 108 is configured to transmit the one or more communication signals to the information system 2500 to identify an individual subject to the information system 2500. For example, the reporter 108 can transmit one or more communication signals that identify an individual to the information system 2500 as patient Greg, whereby the information system 2500 can associate data entries with patient Greg or provide access to information associated with patient Greg to the individual. In an embodiment, the reporter 108 is configured to transmit the one or more communication signals to the information system 2500 to validate an information system entry associated with the individual subject. For example, the reporter 108 can transmit one or more communication signals to the information system 2500 to authenticate the entry as having been entered by or for the identified individual. In an embodiment, the reporter 108 is configured to transmit the one or more communication signals to the information system 2500 in response to a query from the information system 2500. For example, the information system 2500 can query the individual subject identification device 3000 to determine if the individual on whom the individual subject identification device 3000 is placed is an individual authorized to operate an external device. In embodiments, the information system 2500 can query the individual subject identification device 3000 before authorizing an action or activity, a service for the individual, use of an external device, access to information, or periodically (e.g., to make sure that an individual on which the individual subject identification device 3000 is placed can still be identified as patient Greg).

The individual subject identification device 3000 can also be configured to receive communication signals from the information system 2500. In an embodiment, the circuitry 106 is configured to receive (e.g., via receiver 404 or transceiver 406) one or more authorization parameters from the information system 2500. For example, the information system 2500 can program the individual subject identification device 3000 by providing authorization parameters for one or more individuals for whom the individual subject identification device 3000 is operable. For example, the individual subject identification device 3000 can be configured to receive authorization parameters associated with a list of individuals (e.g., patients Greg, Joe, and Lisa) from the information system 2500. The circuitry 106 can be configured to store the one or more authorization parameters received from the information system 2500 in a memory (e.g., memory 402) of the system 100.

The individual subject identification device 3000 can be configured as a single-use device, a multiple-use device, a disposable device, a recyclable device, a reconfigurable device, or the like. In an embodiment, the individual subject identification device 3000 is configured as a single-use device. For example, the circuitry 106 can be configured to authorize a single action or provide a single comparison between reference data and identity sense signals associated with the individual on whom the deformable substrate 102 is placed. In an embodiment, an adhesive (e.g., adhesive 1300) for attaching the individual subject identification device 3000 to a skin surface of a body portion of an individual subject may be configured for a single-use application, whereby the adhesive is no longer capable of attaching the individual subject identification device 3000 to a skin surface after the individual subject identification device 3000 has been adhered to a skin surface and then removed. In an example, an individual subject may receive a new individual subject identification device 3000 before each procedure or other scheduled action. In an embodiment, the circuitry 106 is configured to authorize one or more actions for a single individual subject. For example, the circuitry 106 can be configured to authorize an individual identified as patient Greg to undergo one procedure, receive one treatment, operate one external device, or the like. In an example, an individual subject may receive a new individual subject identification device 3000 before the individual subject is authorized to perform an action requiring identification and authorization. In an embodiment, the circuitry 106 is configured to authorize a plurality of actions for the individual subject. For example, the circuitry 106 can be configured to authorize an individual identified as patient Greg to undergo one or more procedures, receive one or more treatments, or operate one or more external devices. In an embodiment, the circuitry 106 is configured to authorize one or more health service actions for a predefined period of time. For example, the circuitry 106 can be configured to authorize an individual identified as patient Greg to undergo one or more procedures, receive one or more treatments, or operate one or more external devices within a predefined period of time (e.g., within 1 hour, 4 hours, 12 hours, 1 day, 1 week, etc.). In an example, an individual subject may receive a new individual subject identification device 3000 each day or each morning, afternoon, evening, night, or the like. In an embodiment, the circuitry 106 is configured to authorize one or more actions based upon a schedule. For example, the circuitry 106 can be configured with authorization parameters based upon a predetermined schedule for an individual subject on whom the individual subject identification device 3000 is to be placed. For example, the circuitry 106 can be configured with authorization parameters based upon a treatment schedule, a recovery schedule, a rehabilitation schedule, a pre-operative schedule, a post-operative schedule, a discharge schedule, any combination thereof, and so forth.

In an embodiment, the individual subject identification device 3000 is configured to transmit (e.g., via reporter 108) one or more communication signals to the information system 2500 to identify the individual subject and report a location of the individual subject. The information system 2500 can then direct visitors to the individual subject. In an embodiment, the information system 2500 can transmit one or more communication signals to another information system 2800 to impart at least a portion of the information. For example, the individual subject identification device 3000 can identify patient Greg and provide a room number associated with patient Greg to a hospital administrative system, where the hospital administrative system can then communicate the information to a scheduling system to update or receive schedule information associated with Greg. In an example, when a visitor comes to visit patient Greg, the hospital administrative system can log the visitor in and associate visitor with patient Greg. The hospital administrative system can then direct visitor to patient Greg. In some instances, the hospital administrative system can deny authorization to the visitor based on information from a scheduling system regarding patient Greg (e.g., Greg is post-chemotherapy treatment and cannot see visitors for two hours). In an embodiment, the information system 2500 can transmit one or more communication signals associated with patient status (e.g., patient is out of surgery), patient location, visitor permissions/restrictions, and so forth to a guest device, such as a mobile device (e.g., smartphone, tablet, etc.) or the guest identification device 3200 described herein.

Figure 32A:
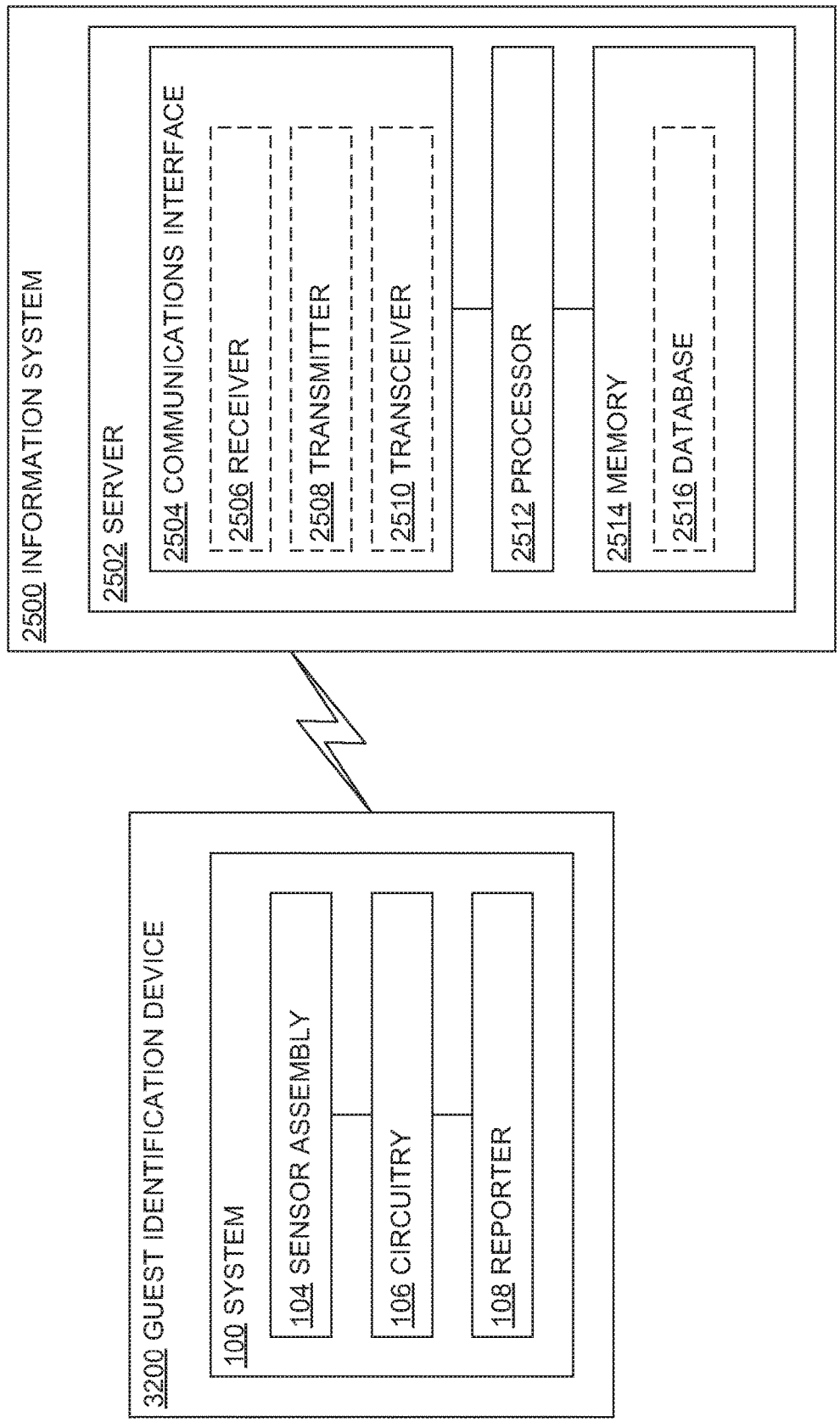
FIG. 32A is a schematic of an embodiment of an information system such as shown in FIG. 25 and a guest identification device in communication with the information system.
Figure 32B:
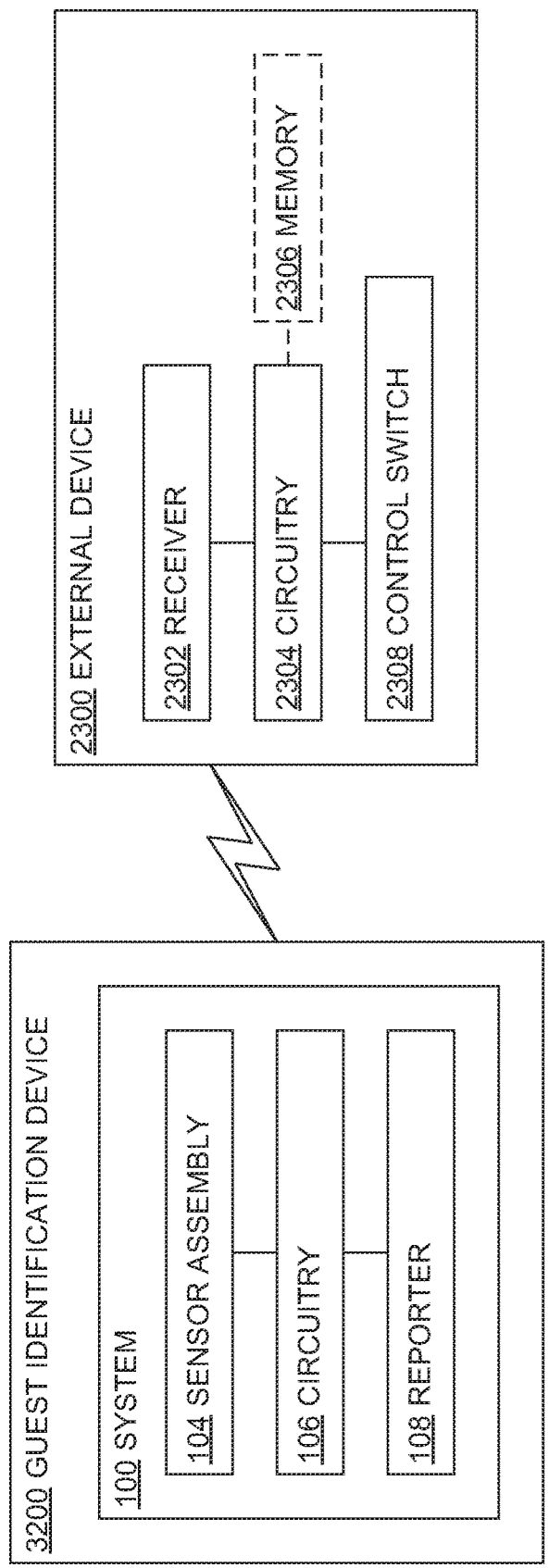
FIG. 32B is a schematic of an embodiment of a guest identification device such as shown in FIG. 32A and an external device in communication with the guest identification device.

In embodiments, shown in FIGS. 32A and 32B, a guest identification device 3200 can be configured to communicate with an external system or device (e.g., an external device or system described herein, including, but not limited to, external device 800, external device 2300, information system 2500, information system 2800, healthcare identification device 2000, healthcare identification device 2900, individual subject identification device 3000, or a combination thereof). The guest identification device 3200 can have structure and functionality that is the same as or similar to healthcare provider identification device 2000 or the individual subject identification device 3000. For example, the guest identification device 3200 can also include a system, such as the system 100 described herein to facilitate the identification of an individual (e.g., a visitor) on whom the guest identification device 3200 is placed. In an embodiment, guest identification device 3200 is configured to generate (e.g., via reporter 108) one or more communication signals associated with an identity of an individual or associated with identity sense signals corresponding to one or more physical characteristics of the individual. In an embodiment, shown in FIG. 32A, the guest identification device 3200 is configured to communicate with information system 2500. The information system 2500 can be configured to receive one or more communication signals associated with an identity of an individual on which the guest identification device 3200 is placed. In an embodiment, the information system 2500 is configured to compare the communication signals with one or more authorization parameters and generate communication signals based on the comparison. For example, the information system 2500 can generate one or more communication signals authorizing a visitor to enter a critical care unit when the visitor is identified as an individual included in a list of close relatives. As shown in FIG. 32B, the guest identification device 3200 can be configured to communicate with external device 2300. In an embodiment, at least one of the guest identification device 3200, the information system 2500, or the external device 2300 can compare an identity or identity sense signals associated with the individual on whom the guest identification device 3200 is placed to one or more authorization parameters to determine whether the individual is authorized to operate the external device 2300. For example, the individual on whom the guest identification device 3200 is placed can be authorized to operate an adjustable hospital bed for a patient lying in the hospital bed when the individual is identified as nephew Billy (a nephew of the patient).

Figure 33:
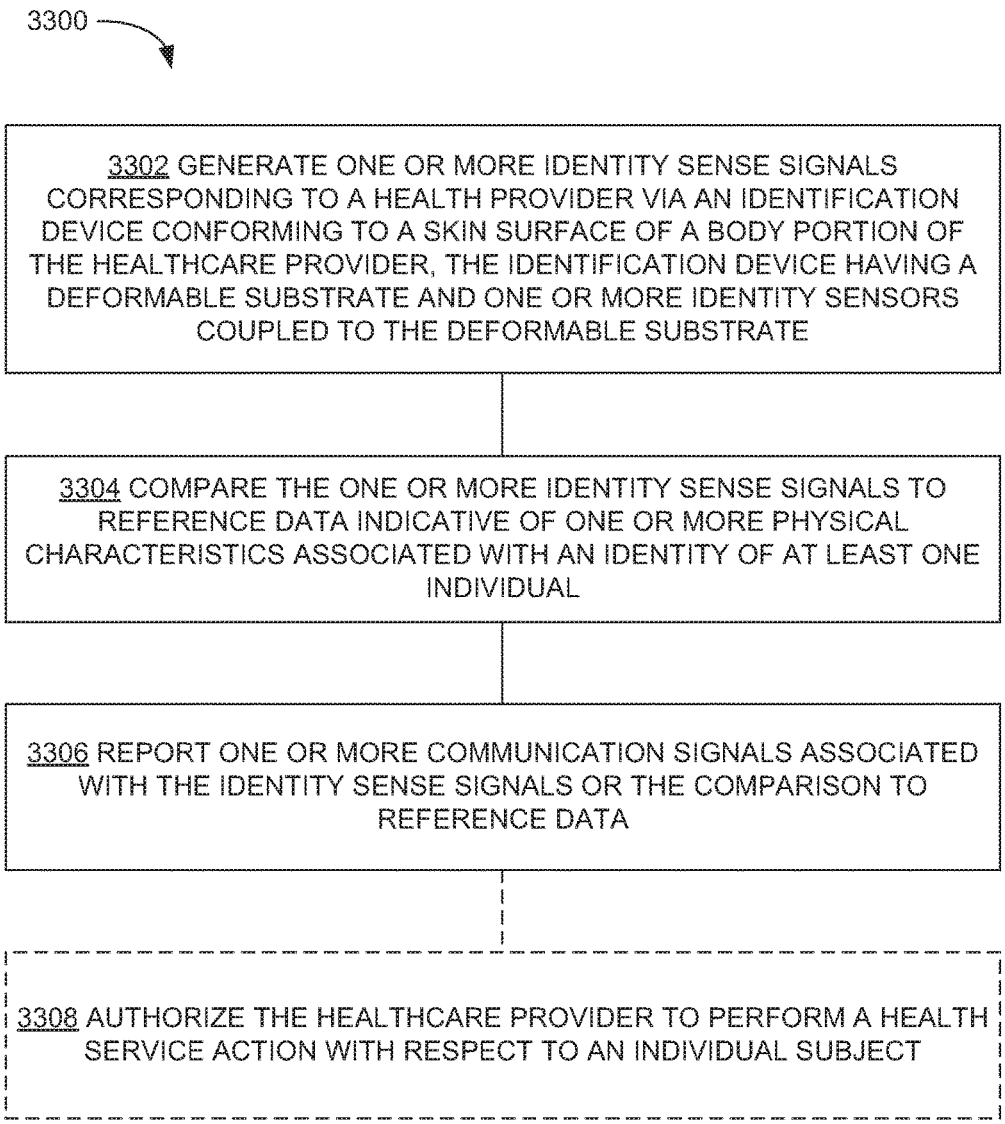
FIG. 33 is a flowchart of a method of identifying a healthcare provider using conformable electronics positioned on the healthcare provider.

FIG. 33 illustrates a method 3300 for identifying a healthcare provider using conformable electronics positioned on the healthcare provider. Method 3300 shows generating one or more identity sense signals in block 3302, where the sense signals correspond to a healthcare provider and are generated by an identification device having a deformable substrate and at least one sensor coupled to the deformable substrate. For example, the sensor assembly 104 (e.g., one or more identity sensors 200) can generate one or more identity sense signals associated with a healthcare provider on which the healthcare identification device 2000 (including system 100) is positioned. Method 3300 also includes comparing the one or more identity sense signals to reference data indicative of one or more physical characteristics associated with an identity of at least one individual in block 3304. For example, the circuitry 106 can compare (e.g., via comparison module 400, via comparison module 1000, etc.) the identity sense signals to reference data stored in memory (e.g., memory 402), where the reference data includes physical characteristics linked or associated with an identity of a known individual. Where the identity sense signals meet or exceed a threshold correspondence when compared to the reference data, the identity linked or associated with the physical characteristics stored in memory can be correlated to the healthcare provider on which the healthcare identification device 2000 (including system 100) is positioned (i.e., the healthcare provider can be presumed to have the known identity based on a successful correspondence). Where the identity sense signals do not meet a threshold correspondence when compared to the reference data, the identity linked or associated with the physical characteristics stored in memory cannot be correlated to the healthcare provider on which the healthcare identification device 2000 (including system 100) is positioned (i.e., the healthcare provider is not presumed to have the known identity based on the unsuccessful correspondence). Method 3300 also includes reporting one or more communication signals related to the identity sense signals or the comparison of the identity sense signals to the reference data in block 3206. For example, the reporter 108 can generate the one or more communication signals responsive to instruction by the circuitry 106, where such communication signals can relate to the identity sense signals or to the comparison by the circuitry 106 of the identity sense signals with the reference data. For example, the communication signals can indicate a successful correspondence between the identity signals and the reference data (e.g., provide the established identity of the healthcare provider on which the healthcare identification device 2000 (including system 100) is positioned), can indicate an unsuccessful correspondence between the identity sense signals and the reference data (e.g., provide that the identity of the healthcare provider on which the healthcare identification device 2000 (including system 100) is positioned cannot be established with a certain threshold correspondence), or the like. In an embodiment, method 3300 includes reporting one or more communication signals related to the identity sense signals or the comparison of the identity sense signals to the reference data in block 3306, prior to authorizing the healthcare provider to perform a health service action with respect to an individual subject in block 3308. For example, an identification or lack of ability to identify the healthcare provider can be reported (e.g., via reporter 108) prior to or in conjunction with an authorization or lack of authorization of the healthcare provider to operate an external device, perform a scheduled procedure, provide a treatment, or the like.

FIG. 34 illustrates a method 3400 for identifying an individual subject using conformable electronics positioned on a healthcare provider. Method 3400 shows generating one or more identity sense signals in block 3402, where the sense signals correspond to an individual subject and are generated by an identification device having a deformable substrate and at least one sensor coupled to the deformable substrate, where the deformable substrate is positioned on a healthcare provider. For example, the sensor assembly 104 (e.g., one or more identity sensors 200 or one or more identity sensors 2100) can generate one or more identity sense signals associated with an individual subject proximate to a healthcare provider on which the healthcare identification device 2000 (including system 100) is positioned. Method 3400 also includes comparing the one or more identity sense signals to reference data indicative of one or more physical characteristics associated with an identity of at least one individual in block 3404. For example, the circuitry 106 can compare (e.g., via comparison module 400, via comparison module 1000, etc.) the identity sense signals to reference data stored in memory (e.g., memory 402), where the reference data includes physical characteristics linked or associated with an identity of a known individual. Where the identity sense signals meet or exceed a threshold correspondence when compared to the reference data, the identity linked or associated with the physical characteristics stored in memory can be correlated to the individual subject (i.e., the individual subject can be presumed to have the known identity based on a successful correspondence). Where the identity sense signals do not meet a threshold correspondence when compared to the reference data, the identity linked or associated with the physical characteristics stored in memory cannot be correlated to the individual subject (i.e., the individual subject is not presumed to have the known identity based on the unsuccessful correspondence). Method 3400 also includes reporting one or more communication signals related to the identity sense signals or the comparison of the identity sense signals to the reference data in block 3206. For example, the reporter 108 can generate the one or more communication signals responsive to instruction by the circuitry 106, where such communication signals can relate to the identity sense signals or to the comparison by the circuitry 106 of the identity sense signals with the reference data. For example, the communication signals can indicate a successful correspondence between the identity signals and the reference data (e.g., provide the established identity of the individual subject), can indicate an unsuccessful correspondence between the identity sense signals and the reference data (e.g., provide that the identity of the individual subject cannot be established with a certain threshold correspondence), or the like. In an embodiment, method 3400 includes reporting one or more communication signals related to the identity sense signals or the comparison of the identity sense signals to the reference data in block 3406, prior to authorizing the healthcare provider to perform a health service action with respect to the individual subject in block 3408. For example, an identification or lack of ability to identify the individual subject can be reported (e.g., via reporter 108) prior to or in conjunction with an authorization or lack of authorization of the healthcare provider to operate an external device, perform a scheduled procedure, provide a treatment, or the like.

FIG. 35 illustrates a method 3500 for identifying and authorizing an individual using conformable electronics positioned on the individual. Method 3500 shows generating one or more identity sense signals in block 3502, where the sense signals correspond to an individual subject and are generated by an identification device having a deformable substrate and at least one sensor coupled to the deformable substrate. For example, the sensor assembly 104 (e.g., one or more identity sensors 200) can generate one or more identity sense signals associated with an individual subject on which the individual subject identification device 3000 (including system 100) is positioned. Method 3500 also includes comparing the one or more identity sense signals to reference data indicative of one or more physical characteristics associated with an identity of at least one individual in block 3504. For example, the circuitry 106 can compare (e.g., via comparison module 400, via identity comparison module 1000) the identity sense signals to reference data stored in memory (e.g., memory 402), where the reference data includes physical characteristics linked or associated with an identity of a known individual. Where the identity sense signals meet or exceed a threshold correspondence when compared to the reference data, the identity linked or associated with the physical characteristics stored in memory can be correlated to the individual subject on which the individual subject identification device 3000 (including system 100) is positioned (i.e., the individual subject can be presumed to have the known identity based on a successful correspondence). Where the identity sense signals do not meet a threshold correspondence when compared to the reference data, the identity linked or associated with the physical characteristics stored in memory cannot be correlated to the individual subject on which the individual subject identification device 3000 (including system 100) is positioned (i.e., the individual subject is not presumed to have the known identity based on the unsuccessful correspondence). Method 3500 also includes comparing the one or more identity sense signals or a determined identity with one or more authorization parameters in block 3506. For example, the circuitry 106 can compare (e.g., via authorization comparison module 1002) the one or more identity sense signals with one or more authorization parameters including at least one scheduled parameter to determine whether the identity sense signals correspond to an individual that is authorized to operate an associated external device (such as when the reference data includes a list of physical characteristics associated with individuals authorized to operate at least a portion of the functionalities of the external device). The circuitry 106 can compare (e.g., via authorization comparison module 1002) an identity of the individual subject (e.g., when the identity sense signals sufficiently correspond to the physical characteristics provided in the reference data in order to identify the individual subject) to a list of individuals authorized to operate the external device to determine whether the identified individual subject can operate at least a portion of the functionalities of the external device. For example, the list of individuals authorized to operate the external device can include, but is not limited to, a list of identities of one or more individuals scheduled to undergo a procedure, a list of identities of one or more individuals scheduled to receive a treatment, a list of identities of one or more individuals scheduled to operate an external device, a list of identities of one or more individuals with pre-operative permissions or restrictions, a list of identities of one or more individuals with post-operative permissions or restrictions, a list of identities of one or more individuals with pre-treatment permissions or restrictions, a list of identities of one or more individuals with post-treatment permissions or restrictions, or a combination thereof. Method 3500 also includes reporting to an associated external device one or more communication signals related to the comparison with authorization parameters in block 3508. For example, the reporter 108 can generate the one or more communication signals responsive to instruction by the circuitry 106 to report to the external device, where such communication signals can relate to whether the individual subject is authorized to operate the external device, such as by being unable to identify the individual (e.g., no authorization), by identifying the individual but the identified individual is not on the authorized list (e.g., no authorization), by successfully corresponding the identity sense signals with physical characteristics of authorized individuals (e.g., authorization), by identifying the individual and having the identified individual being on the authorized list (e.g., authorization), or the like.

Certain embodiments are described herein as including logic or a number of components, modules, or mechanisms. Modules may constitute software modules (e.g., code stored or otherwise embodied on a machine-readable medium or in a transmission medium), hardware modules, or any suitable combination thereof. A "hardware module" is a tangible (e.g., non-transitory) unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field programmable gate array (FPGA) or an ASIC. A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

Accordingly, the phrase "hardware module" should be understood to encompass a tangible entity, and such a tangible entity may be physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where a hardware module comprises a general-purpose processor configured by software to become a special-purpose processor, the general-purpose processor may be configured as respectively different special-purpose processors (e.g., comprising different hardware modules) at different times. Software (e.g., a software module) may accordingly configure one or more processors, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over appropriate circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications.

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, the various embodiments described herein can be implemented, individually and/or collectively, by various types of electro-mechanical systems having a wide range of electrical components such as hardware, software, firmware, and/or virtually any combination thereof and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Examples of electro-mechanical systems include but are not limited to a variety of consumer electronics systems, medical devices, as well as other systems such as motorized transport systems, factory automation systems, security systems, and/or communication/computing systems. Electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

With respect to the use of substantially any plural and/or singular terms herein, the plural can be translated to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

This disclosure has been made with reference to various example embodiments. However, those skilled in the art will recognize that changes and modifications may be made to the embodiments without departing from the scope of the present disclosure. For example, various operational steps, as well as components for carrying out operational steps, may be implemented in alternate ways depending upon the particular application or in consideration of any number of cost functions associated with the operation of the system; e.g., one or more of the steps may be deleted, modified, or combined with other steps.

Additionally, as will be appreciated by one of ordinary skill in the art, principles of the present disclosure, including components, may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create a means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof are intended to cover a non-exclusive inclusion, such that a process, a method, an article, or an apparatus that comprises a list of elements does not include only those elements but may include other elements not expressly listed or inherent to such process, method, system, article, or apparatus.

In embodiments, the system is integrated in such a manner that the system operates as a unique system configured specifically for function of one or more of the systems described herein (e.g., system 100) used to identify and/or authorize individual, such as to operate external devices (e.g., external device 800), and any associated computing devices of the system operate as specific use computers for purposes of the claimed system, and not general use computers. In embodiments, at least one associated computing device of the system operates as a specific use computer for purposes of the claimed system, and not a general use computer. In embodiments, at least one of the associated computing devices of the system is hardwired with a specific ROM to instruct the at least one computing device. In embodiments, one of skill in the art recognizes that the systems described herein (e.g., system 100) and associated systems/devices effect an improvement at least in the technological field(s) of identification and/or authorization.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A device, comprising:
 a deformable substrate configured to conform to a skin surface of a body portion of a healthcare provider;
 a sensor assembly coupled to the deformable substrate, the sensor assembly including one or more identity sensors configured to generate one or more identity sense signals associated with at least one physical characteristic of an individual subject other than the healthcare provider;
 circuitry operably coupled to the sensor assembly and configured to receive the one or more identity sense signals associated with the at least one physical characteristic of the individual subject, the circuitry including
  an identity comparison module configured to compare the one or more identity sense signals generated by the sensor assembly to reference data indicative of one or more physical characteristics associated with an identity of at least one individual to determine whether the one or more identity sense signals correspond to the identity of the at least one individual, and
  an authorization module configured to compare at least one of the one or more identity sense signals or the identity of the at least one individual with one or more authorization parameters, the circuitry configured to authorize the healthcare provider to perform a health service action with respect to the individual subject when a correspondence between at least one of the one or more identity sense signals or the identity of the at least one individual with the one or more authorization parameters is at least at a threshold correspondence; and a reporter operably coupled to the circuitry and configured to generate one or more communication signals responsive to instruction by the circuitry prior to or in conjunction with authorization of the healthcare provider to perform the health service action with respect to the individual subject, the one or more communication signals associated with authorization of the healthcare provider to perform the health service action with respect to the individual subject.

2. The device of claim 1, wherein the one or more communication signals correspond to a comparison of the one or more identity sense signals generated by the sensor assembly to the reference data indicative of one or more physical characteristics associated with the identity of at least one individual.

3. The device of claim 1, wherein the one or more identity sensors are configured to generate one or more second identity sense signals associated with at least one physical characteristic of the healthcare provider.

4. The device of claim 3, further including a comparison module configured to compare the one or more second identity sense signals to reference data indicative of one or more physical characteristics associated with a physical state of the healthcare provider to determine whether the healthcare provider is authorized to operate an external device.

5. The device of claim 1, wherein the one or more authorization parameters include a list of identities of one or more individuals authorized to undergo a scheduled health service procedure.

6. The device of claim 1, wherein the one or more authorization parameters include at least one authorization parameter associated with at least one of a treatment schedule, a recovery schedule, a rehabilitation schedule, a preoperative schedule, or a post-operative schedule.

7. The device of claim 1, wherein the health service action includes at least one of operating an external device, performing a scheduled procedure, or accessing information associated with the individual subject.

8. The device of claim 1, wherein the health service action includes operating an external device including at least one of a medical device, a surgical device, a therapeutic device, an assistive device, an imaging device, a rehabilitative device, or a drug delivery tool.

9. The device of claim 1, wherein the circuitry is further configured to determine a status of the healthcare provider based on at least one of a schedule parameter associated with the healthcare provider, a logged activity state of the healthcare provider, or timing information associated with the healthcare provider.

10. The device of claim 9, wherein the circuitry is configured to prevent authorization of the healthcare provider to perform the health service action with respect to the individual subject based on the status of the healthcare provider.

11. The device of claim 1, wherein the reporter is configured to transmit the one or more communication signals to an information system.

12. The device of claim 11, wherein the information system includes at least one of an electronic health records system, a billing system, a scheduling system, an inventory management system, a claim processing system, or an administrative system.

13. The device of claim 11, wherein the reporter is configured to transmit the one or more communication signals to the information system to identify the individual subject to the information system.

14. The device of claim 11, wherein the reporter is configured to transmit the one or more communication signals to the information system to validate an information system entry associated with the individual subject.

15. A method, comprising:

generating one or more identity sense signals corresponding to an individual subject via an identification device positioned on a body portion of a healthcare provider and having one or more identity sensors, the one or more identity sense signals associated with at least one physical characteristic of the individual subject;

comparing via circuitry the one or more identity sense signals to reference data indicative of one or more physical characteristics associated with an identity of at least one individual to determine whether the one or more identity sense signals correspond to the identity of the at least one individual;

comparing via circuitry at least one of the one or more identity sense signals or the identity of the at least one individual with one or more authorization parameters;

authorizing the healthcare provider to perform a health service action with respect to the individual subject when a correspondence between at least one of the one or more identity sense signals or the identity of the at least one individual with the one or more authorization parameters is at least at a threshold correspondence; and reporting to an external device one or more communication signals associated with authorization of the healthcare provider to perform the health service action with respect to the individual subject.

16. The method of claim 15, further including:

generating one or more second identity sense signals associated with at least one physical characteristic of the healthcare provider.

17. The method of claim 16, further including:

comparing the one or more second identity sense signals to reference data indicative of one or more physical characteristics associated with a physical state of the healthcare provider to determine whether the healthcare provider is authorized to operate the external device.

18. The method of claim 16, further including:

determining a status of the healthcare provider based on at least one of a schedule parameter associated with the healthcare provider, a logged activity state of the healthcare provider, or timing information associated with the healthcare provider.

19. The method of claim 18, further including:

preventing authorization of the healthcare provider to perform the health service action with respect to the individual subject based on the status of the healthcare provider.

20. The method of claim 18, further including:

transmitting the one or more communication signals to an information system.

* * * * *